(12) United States Patent
Xie et al.

(10) Patent No.: US 8,134,003 B2
(45) Date of Patent: Mar. 13, 2012

(54) INDAZOLES, BENZOTHIAZOLES, AND BENZOISOTHIAZOLES, AND PREPARATION AND USES THEREOF

(75) Inventors: Wenge Xie, Mahwah, NJ (US); Brian Herbert, Stockholm, NJ (US); Truc Nguyen, New York, NY (US); Carla Gauss, New York, NY (US); Ashok Tehim, Ridgewood, NJ (US)

(73) Assignee: Memory Pharmaceuticals Corporation, Montvale, NJ (US)

( * ) Notice: Subject to any disclaimer, the term of this patent is extended or adjusted under 35 U.S.C. 154(b) by 0 days.

(21) Appl. No.: 13/103,512

(22) Filed: May 9, 2011

(65) Prior Publication Data

US 2011/0212957 A1    Sep. 1, 2011

Related U.S. Application Data

(63) Continuation of application No. 12/430,944, filed on Apr. 28, 2009, now Pat. No. 7,943,773, which is a continuation of application No. 12/032,068, filed on Feb. 15, 2008, now abandoned, which is a continuation of application No. 10/669,645, filed on Sep. 25, 2003, now Pat. No. 7,429,664.

(60) Provisional application No. 60/413,151, filed on Sep. 25, 2002, provisional application No. 60/448,469, filed on Feb. 21, 2003.

(51) Int. Cl.
   *C07D 211/02* (2006.01)
(52) U.S. Cl. .......... 546/133; 546/135; 544/127
(58) Field of Classification Search ............ 546/112
   See application file for complete search history.

(56) References Cited

U.S. PATENT DOCUMENTS

| | | |
|---|---|---|
| 4,605,652 A | 8/1986 | Welstead et al. |
| 4,775,668 A | 10/1988 | Jefson |
| 4,789,673 A | 12/1988 | Donatsch et al. |
| 4,798,829 A | 1/1989 | King et al. |
| 4,845,092 A | 7/1989 | Sanger et al. |
| 4,886,808 A | 12/1989 | King |
| 4,895,943 A | 1/1990 | Friedmann |
| 4,910,193 A | 3/1990 | Buchheit |
| 4,910,207 A | 3/1990 | Donatsch et al. |
| 4,937,247 A | 6/1990 | King |
| 4,942,160 A | 7/1990 | Sanger et al. |
| 4,975,436 A | 12/1990 | Tyers |
| 4,985,424 A | 1/1991 | van Wijngaarden et al. |
| 5,017,582 A | 5/1991 | Donatsch et al. |
| 5,034,398 A | 7/1991 | King |
| 5,063,231 A | 11/1991 | Sanger et al. |
| 5,098,889 A | 3/1992 | Costall et al. |
| 5,098,909 A | 3/1992 | Williams |
| 5,192,770 A | 3/1993 | Clark et al. |
| 5,204,356 A | 4/1993 | Tyers |
| 5,223,625 A | 6/1993 | Van Wijngaarden et al. |
| 5,272,154 A | 12/1993 | Dixon et al. |
| 5,273,972 A | 12/1993 | Jagdmann et al. |
| 5,446,050 A | 8/1995 | Rosen |
| 5,543,426 A | 8/1996 | Dixon et al. |
| 5,561,149 A | 10/1996 | Azria et al. |
| 5,641,802 A | 6/1997 | Arcamone et al. |
| 5,679,673 A | 10/1997 | Bowen et al. |
| 5,714,946 A | 2/1998 | Gottshall et al. |
| 5,773,436 A | 6/1998 | Muller et al. |
| 5,985,866 A | 11/1999 | Muller et al. |
| 6,492,385 B2 | 12/2002 | Myers et al. |
| 6,500,840 B2 | 12/2002 | Myers et al. |
| 6,565,013 B1 | 5/2003 | Buergler et al. |
| 6,599,916 B2 | 7/2003 | Myers et al. |
| 6,624,173 B1 | 9/2003 | Crooks et al. |
| 6,780,861 B2 | 8/2004 | Nozulak |
| 6,828,330 B2 | 12/2004 | Walker et al. |
| 6,849,620 B2 | 2/2005 | Walker et al. |
| 6,911,543 B2 | 6/2005 | Walker et al. |
| 7,001,900 B2 | 2/2006 | Jacobsen et al. |
| 2002/0086871 A1 | 7/2002 | O'Neill |
| 2002/0119972 A1 | 8/2002 | Leftheris et al. |
| 2003/0073707 A1 | 4/2003 | Walker et al. |
| 2003/0236270 A1 | 12/2003 | Jacobsen et al. |
| 2004/0002513 A1 | 1/2004 | Mazurov et al. |
| 2004/0132790 A1 | 7/2004 | Xie et al. |
| 2004/0138286 A1 | 7/2004 | Imazaki et al. |
| 2004/0224977 A1 | 11/2004 | Walker et al. |
| 2005/0182062 A1 | 8/2005 | Galli et al. |
| 2005/0209236 A1 | 9/2005 | Hendrix |
| 2006/0014750 A1 | 1/2006 | O'Donnell et al. |
| 2006/0019984 A1 | 1/2006 | Groppi et al. |
| 2006/0160877 A1 | 7/2006 | Luithle et al. |
| 2007/0078147 A1 | 4/2007 | Schumacher et al. |

FOREIGN PATENT DOCUMENTS

CA    2 361 437    8/2000

(Continued)

OTHER PUBLICATIONS

Evans et al., "Probing the 5-HTz$_3$ Receptor Site Using Novel Indole-3-Glyoxylic Acid Derivatives", Med. Chem. Res. (1993), 3:386-406.

(Continued)

*Primary Examiner* — Andrew D Kosar
*Assistant Examiner* — Raymond Covington
(74) *Attorney, Agent, or Firm* — Millen, White, Zelano & Branigan, P.C.

(57) ABSTRACT

The present invention relates generally to the field of ligands for nicotinic acetylcholine receptors (nAChR), activation of nAChRs, and the treatment of disease conditions associated with defective or malfunctioning nicotinic acetylcholine receptors, especially of the brain. Further, this invention relates to novel compounds (indazoles and benzothiazoles), which act as ligands for the α7 nAChR subtype, methods of preparing such compounds, compositions containing such compounds, and methods of use thereof.

18 Claims, No Drawings

FOREIGN PATENT DOCUMENTS

| | | |
|---|---|---|
| DE | 101 56 719 | 5/2003 |
| DE | 103 05 922 | 3/2004 |
| EP | 0 013 138 | 7/1980 |
| EP | 0 190 920 | 8/1986 |
| EP | 0 200 444 | 11/1986 |
| EP | 0 214 772 | 3/1987 |
| EP | 0 261 964 | 3/1988 |
| EP | 0 279 512 | 8/1988 |
| EP | 0 377 238 | 7/1990 |
| EP | 0 498 466 | 8/1992 |
| EP | 1 079 828 | 3/2001 |
| EP | 1 217 001 | 6/2002 |
| EP | 1 219 622 | 7/2002 |
| EP | 1 235 826 | 9/2002 |
| FR | 2 548 666 | 1/1985 |
| GB | 2 125 398 | 3/1984 |
| GB | 2 145 416 | 3/1985 |
| JP | 2002-30084 | 1/2002 |
| JP | 2003 503625 | 1/2003 |
| WO | WO 84/00166 | 1/1984 |
| WO | WO 85/01048 | 3/1985 |
| WO | WO 90 14347 | 11/1990 |
| WO | WO 91/09593 | 7/1991 |
| WO | WO 92/12149 | 7/1992 |
| WO | WO 93 08185 | 4/1993 |
| WO | WO-94 14805 | 7/1994 |
| WO | WO 97 30998 | 8/1997 |
| WO | WO 00 45846 | 8/2000 |
| WO | WO 00 58311 | 10/2000 |
| WO | WO 01 58869 | 8/2001 |
| WO | WO 01 90109 | 11/2001 |
| WO | WO 01 92260 | 12/2001 |
| WO | WO 02/17358 | 2/2002 |
| WO | WO 02 36114 | 5/2002 |
| WO | WO 02/085901 | 10/2002 |
| WO | WO 02/096911 | 12/2002 |
| WO | WO 02/100833 | 12/2002 |
| WO | WO 02 100857 | 12/2002 |
| WO | WO 02 100858 | 12/2002 |
| WO | WO 03/022856 | 3/2003 |
| WO | WO 03 029252 | 4/2003 |
| WO | WO 03 037896 | 5/2003 |
| WO | WO 03/042210 | 5/2003 |
| WO | WO 03 051874 | 6/2003 |
| WO | WO 03 070731 | 8/2003 |
| WO | WO 03/072578 | 9/2003 |
| WO | WO 03/078431 | 9/2003 |
| WO | WO 03 080606 | 10/2003 |
| WO | WO 03/094830 | 11/2003 |
| WO | WO 03/101987 | 11/2003 |
| WO | WO 2004 014864 | 2/2004 |
| WO | WO 2004 014922 | 2/2004 |
| WO | WO 2004/016616 | 2/2004 |
| WO | WO 2004/016617 | 2/2004 |
| WO | WO-2004 029050 | 4/2004 |
| WO | WO 2004 033456 | 4/2004 |
| WO | WO-2004 052348 | 6/2004 |
| WO | WO-2004 052461 | 6/2004 |
| WO | WO 2005 012299 | 2/2005 |

OTHER PUBLICATIONS

Flammia, "Lobeline: Structure-Affinity Investigation of Nicotinic Acetylcholinergic Receptor Binding", J. Med. Chem. (1999), 42:3726-2731.

Azuma et al. "Metabolism and Disposition of GTS-21, A Novel Drug for Alzheimer's Disease", Xenobiotica (1999), vol. 29, No. 7, pp. 747-762.

Stevens et al., "Selective $\alpha_7$-nicotinic agonists normalize inhibition of auditory response in DBA mice", Psychopharmacology (1998), 136:320-327.

Azuma et al., "The effect of repeat administration of GTS-21 on mixed-function oxidase activities in rat", Elsevier Science Ireland Ltd., Toxicology Letters 110 (1999) pp. 137-144.

Decker, et al., "Neuronal Nicotinic Acetylcholine Receptors: Novel Targets for CNS Therapeutics", pp. 1-14, (2001).

Holladay et al., "Neuronal Nicotinic Acetylcholine Receptors as Targets for Drug Discovery", Journal of Medicinal Chemistry, vol. 40, No. 26, (1997), pp. 4169-4194.

Japan Patent Abstract No. 2002-030084 dated Jan. 29, 2002 (machine translation).

Astles et al., Current Drug Targets—CNS Neurological Disorders, 2002, 1, pp. 337-348.

Mazurov et al., Biorg. & Med. Chem. Lett., 2005, No. 15, pp. 2073-2077.

Nuhrich et al., Eur. J. Med. Chem., 1996, No. 31, pp. 957-964.

Bermudez et al., J. Med. Chem. 1990, 33, 1924-1929.

Australian Search Report and Written Opinion for Application No. 2006 06539-5 mailed Oct. 3, 2008.

European Search Report for EP 05 75 5169 dated Apr. 3, 2008.

International Search Report for PCT/US2005/010120 dated Sep. 1, 2005.

INDAZOLES, BENZOTHIAZOLES, AND BENZOISOTHIAZOLES, AND PREPARATION AND USES THEREOF

This application is a continuation of Ser. No. 12/430,944, filed Apr. 28, 2009, now U.S. Pat. No. 7,943,773, which is a continuation of Ser. No. 12/032,068, filed Feb. 15, 2008 now abandoned, which is a continuation of Ser. No. 10/669,645, filed Sep. 25, 2003, now U.S. Pat. No. 7,429,664; and this application claims the benefit of U.S. Provisional application Ser. No. 60/413,151, filed Sep. 25, 2002, and U.S. Provisional application Ser. No. 60/448,469, filed Feb. 21, 2003, the entire disclosures of which are hereby incorporated by reference.

FIELD OF THE INVENTION

The present invention relates generally to the field of ligands for nicotinic acetylcholine receptors (nAChR), activation of nAChRs, and the treatment of disease conditions associated with defective or malfunctioning nicotinic acetylcholine receptors, especially of the brain. Further, this invention relates to novel compounds, which act as ligands for the α7 nAChR subtype, methods of preparing such compounds, compositions comprising such compounds, and methods of use thereof.

BACKGROUND OF THE INVENTION

There are two types of receptors for the neurotransmitter, acetylcholine: muscarinic receptors and nicotinic receptors, based on the selectivity of action of muscarine and nicotine, respectively. Muscarinic receptors are G-protein coupled receptors. Nicotinic receptors are members of the ligand-gated ion channel family. When activated, the conductance of ions across the nicotinic ion channels increases.

Nicotinic alpha-7 receptor protein forms a homo-pentameric channel in vitro that is highly permeable to a variety of cations (e.g., $Ca^{++}$). Each nicotinic alpha-7 receptor has four transmembrane domains, named M1, M2, M3, and M4. The M2 domain has been suggested to form the wall lining the channel. Sequence alignment shows that nicotinic alpha-7 is highly conserved during evolution. The M2 domain that lines the channel is identical in protein sequence from chicken to human. For discussions of the alpha-7 receptor, see, e.g., Revab et al. (1991), *Nature,* 353, 846-849; Galzi et al. (1992), *Nature* 359, 500-505; Fucile et al. (2000), *PNAS* 97(7), 3643-3648; Briggs et al. (1999), *Eur. J. Pharmacol.* 366 (2-3), 301-308; and Gopalakrishnan et al. (1995), *Eur. J. Pharmacol.* 290(3), 237-246.

The nicotinic alpha-7 receptor channel is expressed in various brain regions and is believed to be involved in many important biological processes in the central nervous system (CNS), including learning and memory. Nicotinic alpha-7 receptors are localized on both presynaptic and postsynaptic terminals and have been suggested to be involved in modulating synaptic transmission. It is therefore of interest to develop novel compounds, which act as ligands for the α7 nAChR subtype, for the treatment of disease conditions associated with defective or malfunctioning nicotinic acetylcholine receptors.

SUMMARY OF THE INVENTION

This invention relates to novel compounds, which act as ligands for the α7 nAChR subtype, methods of preparing such compounds, compositions comprising such compounds, and methods of use thereof.

DETAILED DESCRIPTION OF THE INVENTION

The present invention includes compounds of Formulas I, II, III, or IV:

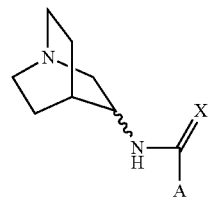

(I)

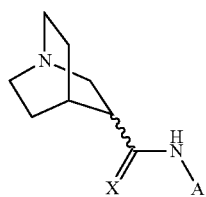

(II)

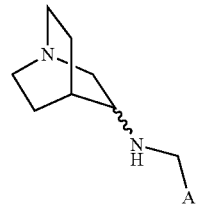

(III)

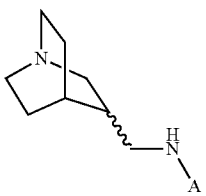

(IV)

wherein
A is

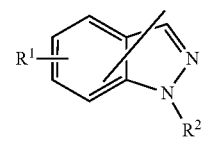

(a)

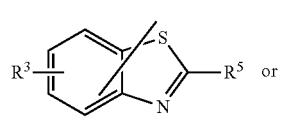

(b)

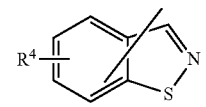

(c)

X is O or S;
$R^1$ is H, F, Cl, Br, I, OH, CN, nitro, $NH_2$, alkyl having 1 to 4 carbon atoms, fluorinated alkyl having 1 to 4 carbon atoms (e.g., $CF_3$), cycloalkyl having 3 to 7 carbon atoms, cycloalkylalkyl having 4 to 7 carbon atoms, alkoxy having 1 to 4 carbon atoms (e.g., $OCH_3$), cycloalkoxy having 3 to 7 carbon atoms, cycloalkylalkoxy having 4 to 7 carbon atoms, alkylthio having 1 to 4 carbon atoms (e.g., $SCH_3$), fluorinated alkoxy having 1 to 4 carbon atoms (e.g., $OCF_3$, $OCHF_2$), hydoxyalkyl having 1 to 4 carbon atoms, hydroxyalkoxy having 2 to 4 carbon atoms, monoalkylamino having 1 to 4 carbon atoms, dialkylamino wherein each alkyl group independently has 1 to 4 carbon atoms, Ar or Het;

$R^{2'}$ is H, alkyl having 1 to 4 carbon atoms, cycloalkyl having 3 to 7 carbon atoms, or cycloalkylalkyl having 4 to 7 carbon atoms;

$R^3$ is H, F, Cl, Br, I, OH, CN, nitro, $NH_2$, alkyl having 1 to 4 carbon atoms, fluorinated alkyl having 1 to 4 carbon atoms (e.g., $CF_3$), cycloalkyl having 3 to 7 carbon atoms, cycloalkylalkyl having 4 to 7 carbon atoms, alkoxy having 1 to 4 carbon atoms (e.g., $OCH_3$), cycloalkoxy having 3 to 7 carbon atoms, cycloalkylalkoxy having 4 to 7 carbon atoms, alkylthio having 1 to 4 carbon atoms (e.g., $SCH_3$), fluorinated alkoxy having 1 to 4 carbon atoms (e.g., $OCF_3$, $OCHF_2$), hydoxyalkyl having 1 to 4 carbon atoms, hydroxyalkoxy having 2 to 4 carbon atoms, monoalkylamino having 1 to 4 carbon atoms, dialkylamino wherein each alkyl group independently has 1 to 4 carbon atoms, Ar or Het;

$R^4$ is H, F, Cl, Br, I, OH, CN, nitro, $NH_2$, alkyl having 1 to 4 carbon atoms, fluorinated alkyl having 1 to 4 carbon atoms (e.g., $CF_3$), cycloalkyl having 3 to 7 carbon atoms, cycloalkylalkyl having 4 to 7 carbon atoms, alkoxy having 1 to 4 carbon atoms (e.g., $OCH_3$), cycloalkoxy having 3 to 7 carbon atoms, cycloalkylalkoxy having 4 to 7 carbon atoms, alkylthio having 1 to 4 carbon atoms (e.g., $SCH_3$), fluorinated alkoxy having 1 to 4 carbon atoms (e.g., $OCF_3$, $OCHF_2$), hydoxyalkyl having 1 to 4 carbon atoms, hydroxyalkoxy having 2 to 4 carbon atoms, monoalkylamino having 1 to 4 carbon atoms, dialkylamino wherein each alkyl group independently has 1 to 4 carbon atoms, Ar or Het;

$R^5$ is H, F, Cl, Br, I, OH, CN, nitro, $NH_2$, alkyl having 1 to 4 carbon atoms, fluorinated alkyl having 1 to 4 carbon atoms (e.g., $CF_3$), cycloalkyl having 3 to 7 carbon atoms, cycloalkylalkyl having 4 to 7 carbon atoms, alkoxy having 1 to 4 carbon atoms (e.g., $OCH_3$), cycloalkoxy having 3 to 7 carbon atoms, cycloalkylalkoxy having 4 to 7 carbon atoms, alkylthio having 1 to 4 carbon atoms (e.g., $SCH_3$), fluorinated alkoxy having 1 to 4 carbon atoms (e.g., $OCF_3$, $OCHF_2$), hydoxyalkyl having 1 to 4 carbon atoms, hydroxyalkoxy having 2 to 4 carbon atoms, monoalkylamino having 1 to 4 carbon atoms, dialkylamino wherein each alkyl group independently has 1 to 4 carbon atoms, Ar or Het;

Ar is an aryl group containing 6 to 10 carbon atoms which is unsubstituted or substituted one or more times by alkyl having 1 to 8 C atoms, alkoxy having 1 to 8 C atoms, halogen (F, Cl, Br, or I, preferably F or Cl), dialkylamino wherein the alkyl portions each have 1 to 8 C atoms, amino, cyano, hydroxyl, nitro, halogenated alkyl having 1 to 8 C atoms, halogenated alkoxy having 1 to 8 C atoms, hydroxyalkyl having 1 to 8 C atoms, hydroxyalkoxy having 2 to 8 C atoms, alkenyloxy having 3 to 8 C atoms, alkylthio having 1 to 8 C atoms, alkylsulphinyl having 1 to 8 C atoms, alkylsulphonyl having 1 to 8 C atoms, monoalkylamino having 1 to 8 C atoms, cycloalkylamino wherein the cycloalkyl group has 3 to 7 C atoms and is optionally substituted, aryloxy wherein the aryl portion contains 6 to 10 carbon atoms (e.g., phenyl, naphthyl, biphenyl) and is optionally substituted, arylthio wherein the aryl portion contains 6 to 10 carbon atoms (e.g., phenyl, naphthyl, biphenyl) and is optionally substituted, cycloalkyloxy wherein the cycloalkyl group has 3 to 7 C atoms and is optionally substituted, sulfo, sulfonylamino, acylamido (e.g., acetamido), acyloxy (e.g., acetoxy) or combinations thereof; and Het is a heterocyclic group, which is fully saturated, partially saturated or fully unsaturated, having 5 to 10 ring atoms in which at least 1 ring atom is a N, O or S atom, which is unsubstituted or substituted one or more times by halogen (F, Cl, Br, or I, preferably F or Cl), aryl having 6 to 10 carbon atoms (e.g., phenyl, naphthyl, biphenyl) and is optionally substituted, alkyl having 1 to 8 C atoms, alkoxy having 1 to 8 C atoms, cyano, trifluoromethyl, nitro, oxo, amino, monoalkylamino having 1 to 8 C atoms, dialkylamino wherein each alkyl group has 1 to 8 C atoms, or combinations thereof; and pharmaceutically acceptable salts thereof.

In Formula I, when A is an indazolyl group of subformula (a), it is preferably attached to the remainder of the compound via its 3, 4 or 7 position. When A is a benzothiazolyl group of subformula (b), it is preferably attached to the remainder of the compound via its 4 or 7 position. When A is a benzoisothiazolyl group of subformula (c), it is preferably attached to the remainder of the compound via its 3, 4 or 7 position.

Similarly, in Formula II, when A is an indazolyl group of subformula (a), it is preferably attached to the remainder of the compound via its 3, 4 or 7 position. When A is a benzothiazolyl group of subformula (b), it is preferably attached to the remainder of the compound via its 4 or 7 position. When A is a benzoisothiazolyl group of subformula (c), it is preferably attached to the remainder of the compound via its 3, 4 or 7 position.

Also, in Formula III, when A is an indazolyl group of subformula (a), it is preferably attached to the remainder of the compound via its 3, 4 or 7 position. When A is a benzothiazolyl group of subformula (b), it is preferably attached to the remainder of the compound via its 4 or 7 position. When A is a benzoisothiazolyl group of subformula (c), it is preferably attached to the remainder of the compound via its 3, 4 or 7 position.

Further, in Formula IV, when A is an indazolyl group of subformula (a), it is preferably attached to the remainder of the compound via its 3, 4 or 7 position. When A is a benzothiazolyl group of subformula (b), it is preferably attached to the remainder of the compound via its 4 or 7 position. When A is a benzoisothiazolyl group of subformula (c), it is preferably attached to the remainder of the compound via its 3, 4 or 7 position.

The present invention includes compounds of Formulas I', II', III', or IV':

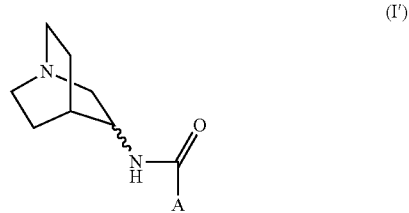

(I')

-continued

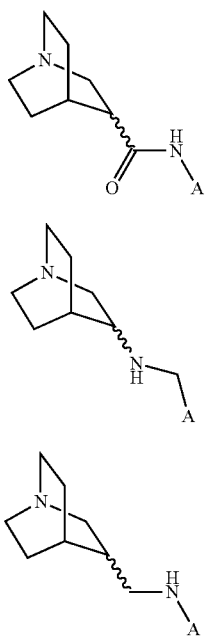

wherein
A is

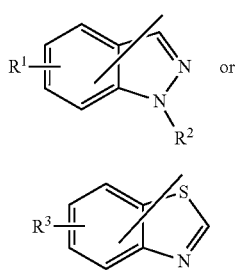

R¹ is H, F, Cl, Br, I, OH, CN, nitro, NH₂, alkyl having 1 to 4 carbon atoms, fluorinated alkyl having 1 to 4 carbon atoms (e.g., CF₃), cycloalkyl having 3 to 7 carbon atoms, cycloalkylalkyl having 4 to 7 carbon atoms, alkoxy having 1 to 4 carbon atoms (e.g., OCH₃), cycloalkoxy having 3 to 7 carbon atoms, alkylthio having 1 to 4 carbon atoms (e.g., SCH₃), fluorinated alkoxy having 1 to 4 carbon atoms (e.g., OCF₃, OCHF₂), hydoxyalkyl having 1 to 4 carbon atoms, hydroxyalkoxy having 2 to 4 carbon atoms, monoalkylamino having 1 to 4 carbon atoms, dialkylamino wherein each alkyl group independently has 1 to 4 carbon atoms, Ar or Het;

R² is H, alkyl having 1 to 4 carbon atoms, cycloalkyl having 3 to 7 carbon atoms, or cycloalkylalkyl having 4 to 7 carbon atoms;

R³ is H, F, Cl, Br, I, OH, CN, nitro, NH₂, alkyl having 1 to 4 carbon atoms, fluorinated alkyl having 1 to 4 carbon atoms (e.g., CF₃), cycloalkyl having 3 to 7 carbon atoms, cycloalkylalkyl having 4 to 7 carbon atoms, alkoxy having 1 to 4 carbon atoms (e.g., OCH₃), cycloalkoxy having 3 to 7 carbon atoms, alkylthio having 1 to 4 carbon atoms (e.g., SCH₃), fluorinated alkoxy having 1 to 4 carbon atoms (e.g., OCF₃, OCHF₂), hydoxyalkyl having 1 to 4 carbon atoms, hydroxyalkoxy having 2 to 4 carbon atoms, monoalkylamino having 1 to 4 carbon atoms, dialkylamino wherein each alkyl group independently has 1 to 4 carbon atoms, Ar or Het;

Ar is an aryl group containing 6 to 10 carbon atoms which is unsubstituted or substituted one or more times by alkyl having 1 to 8 C atoms, alkoxy having 1 to 8 C atoms, halogen (F, Cl, Br, or I, preferably F or Cl), dialkylamino wherein the alkyl portions each have 1 to 8 C atoms, amino, cyano, hydroxyl, nitro, halogenated alkyl having 1 to 8 C atoms, halogenated alkoxy having 1 to 8 C atoms, hydroxyalkyl having 1 to 8 C atoms, hydroxyalkoxy having 2 to 8 C atoms, alkenyloxy having 3 to 8 C atoms, alkylthio having 1 to 8 C atoms, alkylsulphinyl having 1 to 8 C atoms, alkylsulphonyl having 1 to 8 C atoms, monoalkylamino having 1 to 8 C atoms, cycloalkylamino wherein the cycloalkyl group has 3 to 7 C atoms and is optionally substituted, aryloxy wherein the aryl portion contains 6 to 10 carbon atoms (e.g., phenyl, naphthyl, biphenyl) and is optionally substituted, arylthio wherein the aryl portion contains 6 to 10 carbon atoms (e.g., phenyl, naphthyl, biphenyl) and is optionally substituted, cycloalkyloxy wherein the cycloalkyl group has 3 to 7 C atoms and is optionally substituted, sulfo, sulfonylamino, acylamido (e.g., acetamido), acyloxy (e.g., acetoxy) or combinations thereof; and Het is a heterocyclic group, which is fully saturated, partially saturated or fully unsaturated, having 5 to 10 ring atoms in which at least 1 ring atom is a N, O or S atom, which is unsubstituted or substituted one or more times by halogen (F, Cl, Br, or I, preferably F or Cl), aryl having 6 to 10 carbon atoms (e.g., phenyl, naphthyl, biphenyl) and is optionally substituted, alkyl having 1 to 8 C atoms, alkoxy having 1 to 8 C atoms, cyano, trifluoromethyl, nitro, oxo, amino, monoalkylamino having 1 to 8 C atoms, dialkylamino wherein each alkyl group has 1 to 8 C atoms, or combinations thereof; and pharmaceutically acceptable salts thereof.

In Formula I', when A is an indazolyl group of subformula (a), it is preferably attached to the remainder of the compound via its 3, 4 or 7 position. When A is a benzothiazolyl group of subformula (b), it is preferably attached to the remainder of the compound via its 4 or 7 position.

Similarly, in Formula II', when A is an indazolyl group of subformula (a), it is preferably attached to the remainder of the compound via its 3, 4 or 7 position. When A is a benzothiazolyl group of subformula (b), it is preferably attached to the remainder of the compound via its 4 or 7 position.

Also, in Formula III', when A is an indazolyl group of subformula (a), it is preferably attached to the remainder of the compound via its 3, 4 or 7 position. When A is a benzothiazolyl group of subformula (b), it is preferably attached to the remainder of the compound via its 4 or 7 position.

Further, in Formula IV', when A is an indazolyl group of subformula (a), it is preferably attached to the remainder of the compound via its 3, 4 or 7 position. When A is a benzothiazolyl group of subformula (b), it is preferably attached to the remainder of the compound via its 4 or 7 position.

In Formulas I-IV and I'-IV', the indazolyl, benzothiazolyl and benzoisothiazolyl groups of A can be attached to the remainder of the structure via any suitable attachment point. The following subformulas illustrate some of the preferred attachments between the indazole and benzothiazole groups and the remainder of the structure.

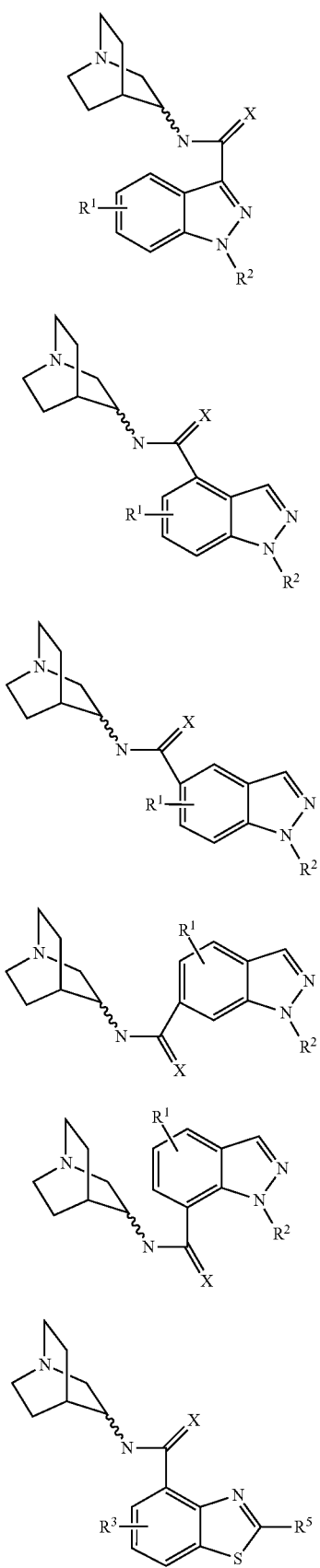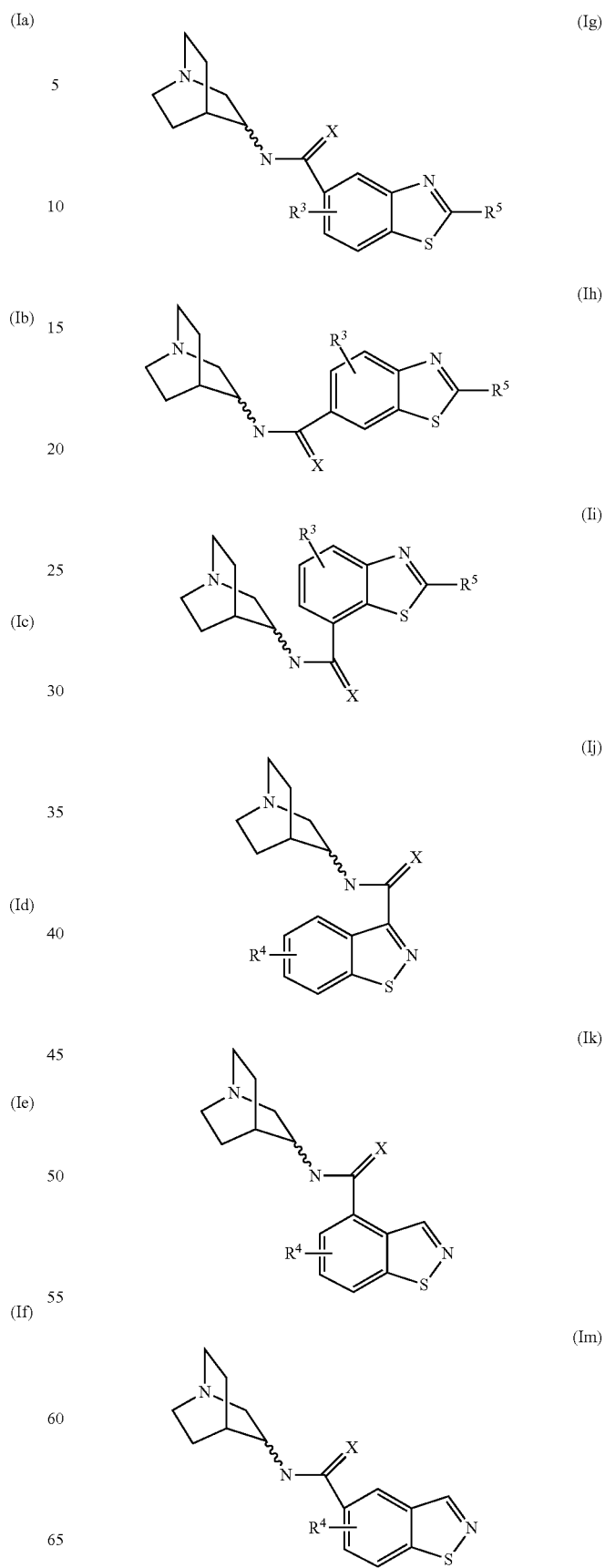

(In)
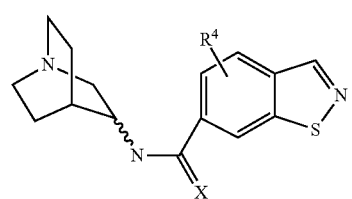
(Io)
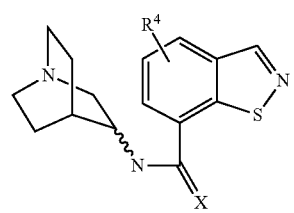
(I'a)
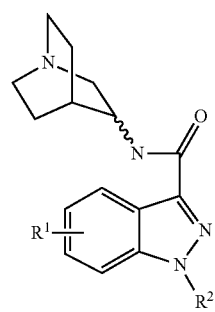
(I'b)
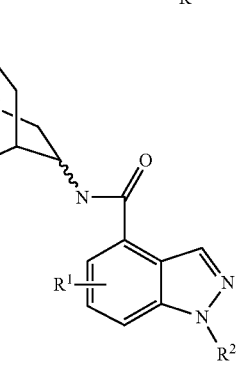
(I'c)
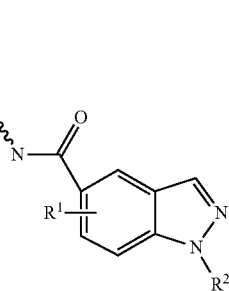
(I'd)
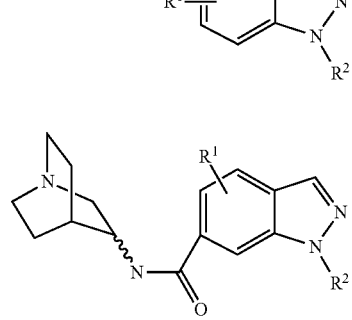
(I'e)
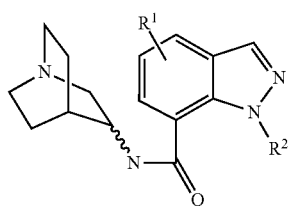
(I'f)
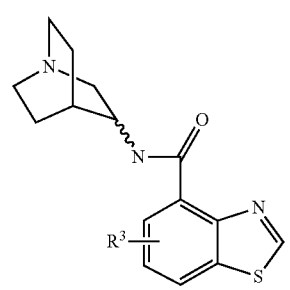
(I'g)
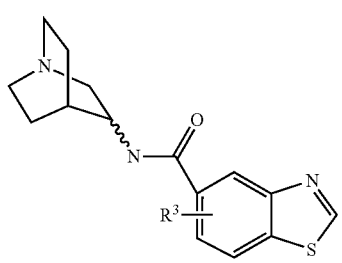
(I'h)
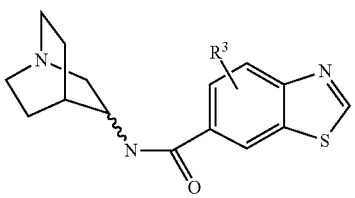
(I'i)
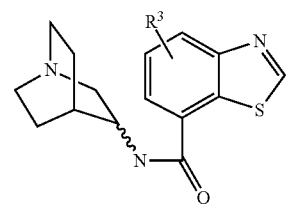
The following subformulas further illustrate some of the preferred attachments between the indazolyl, benzothiazolyl and benzoisothiazolyl groups and the remainder of the structure.

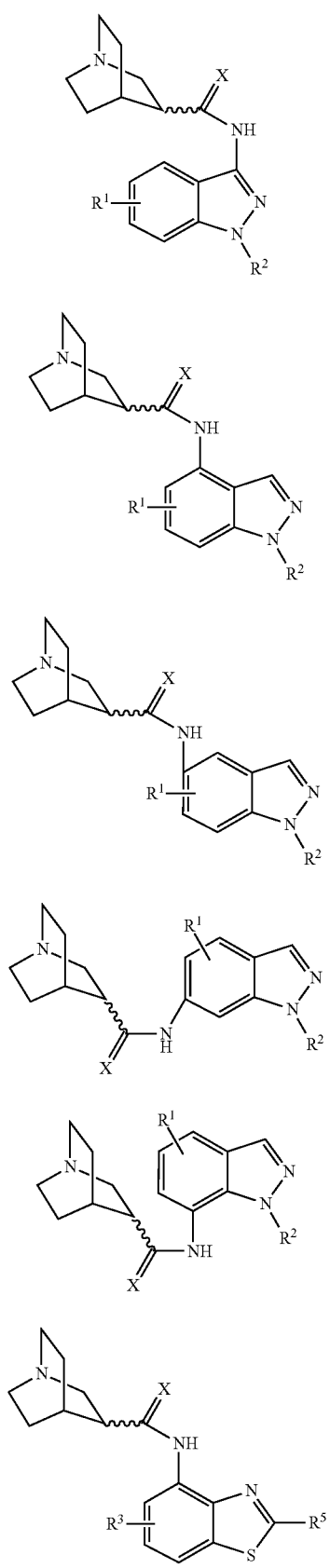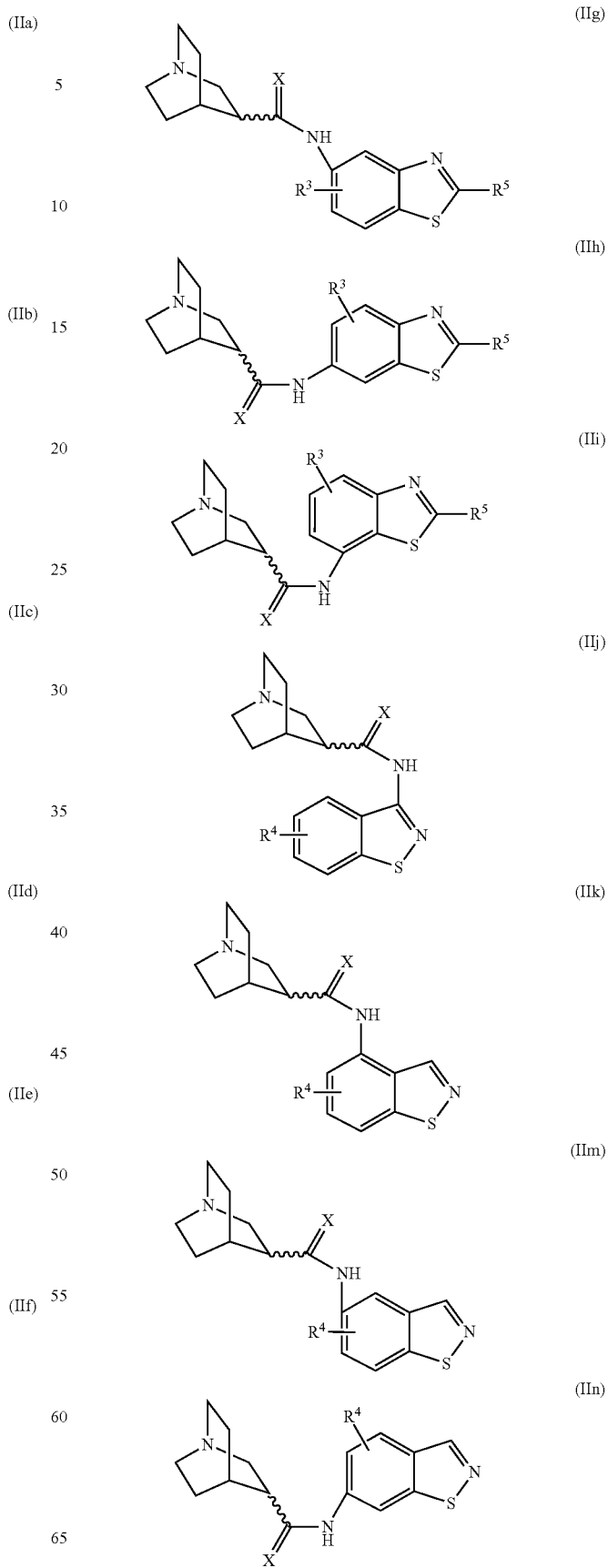

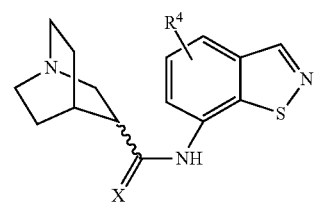
(IIo)
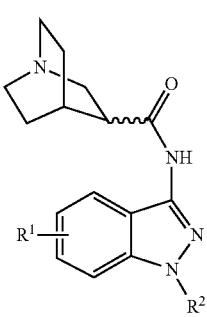
(II'a)
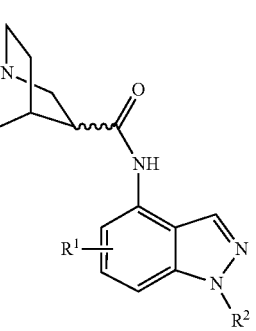
(II'b)
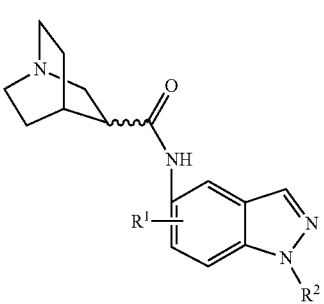
(II'c)
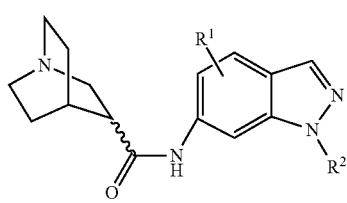
(II'd)
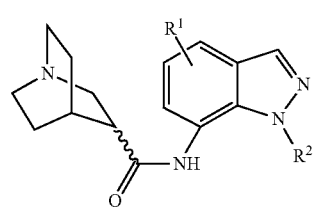
(II'e)
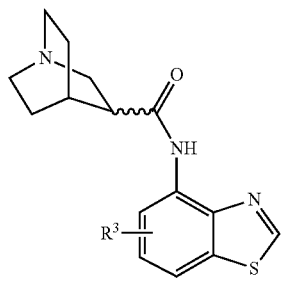
(II'f)
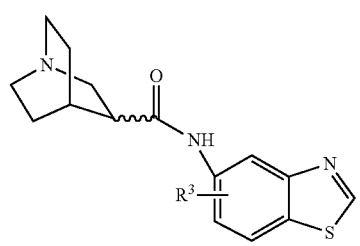
(II'g)
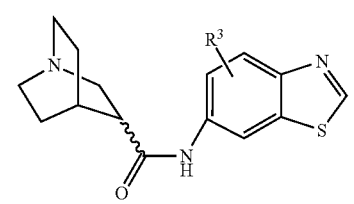
(II'h)
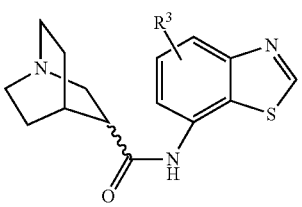
(II'i)
The following subformulas further illustrate some of the preferred attachments between the indazolyl, benzothiazolyl and benzoisothiazolyl groups and the remainder of the structure.
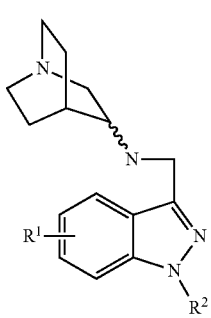
(IIIa)

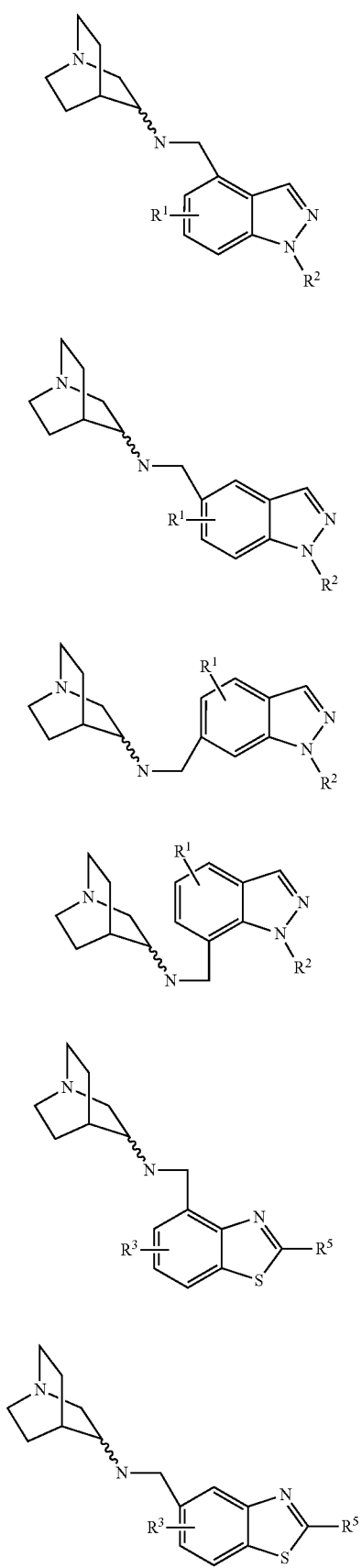
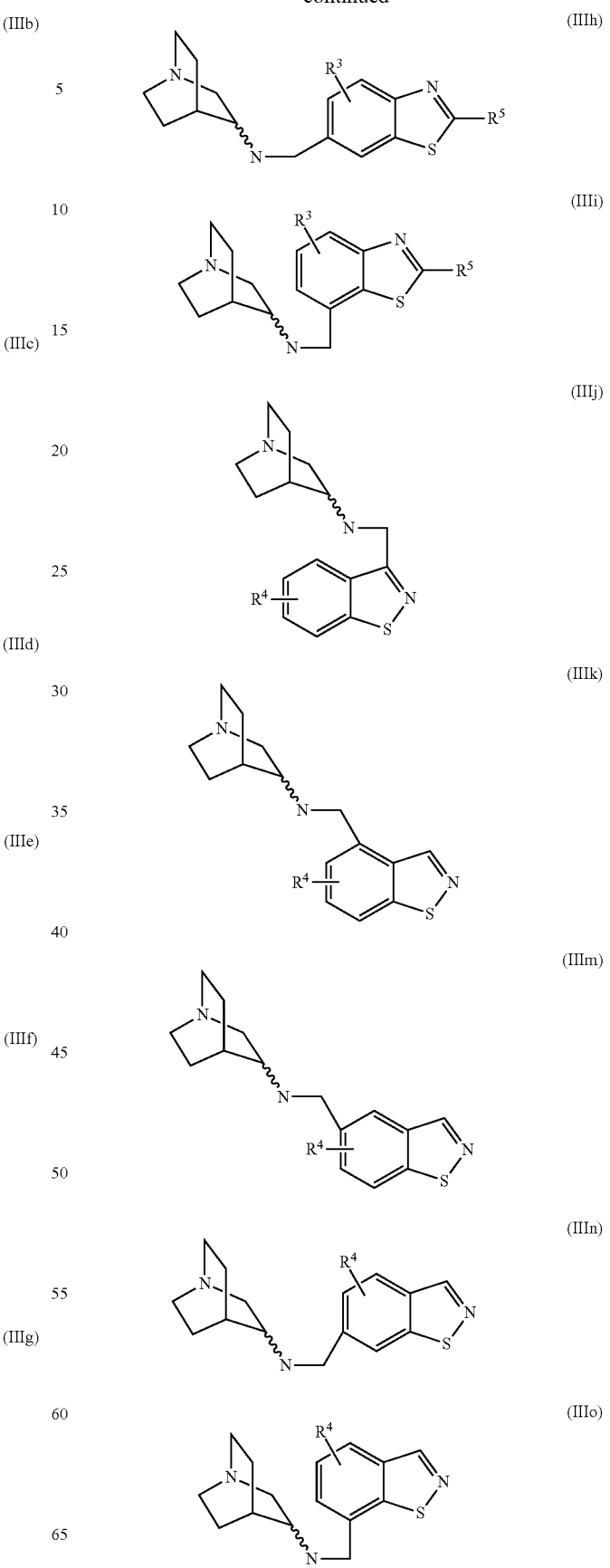

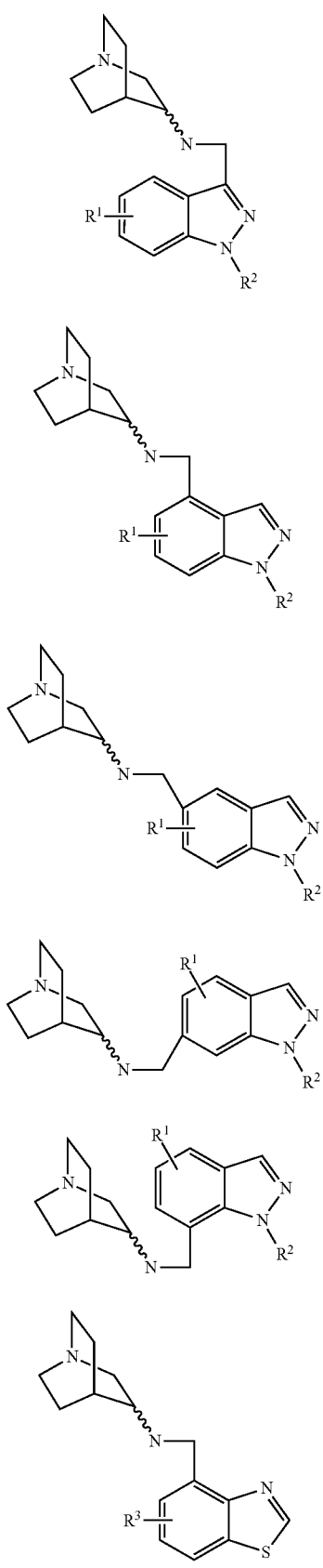
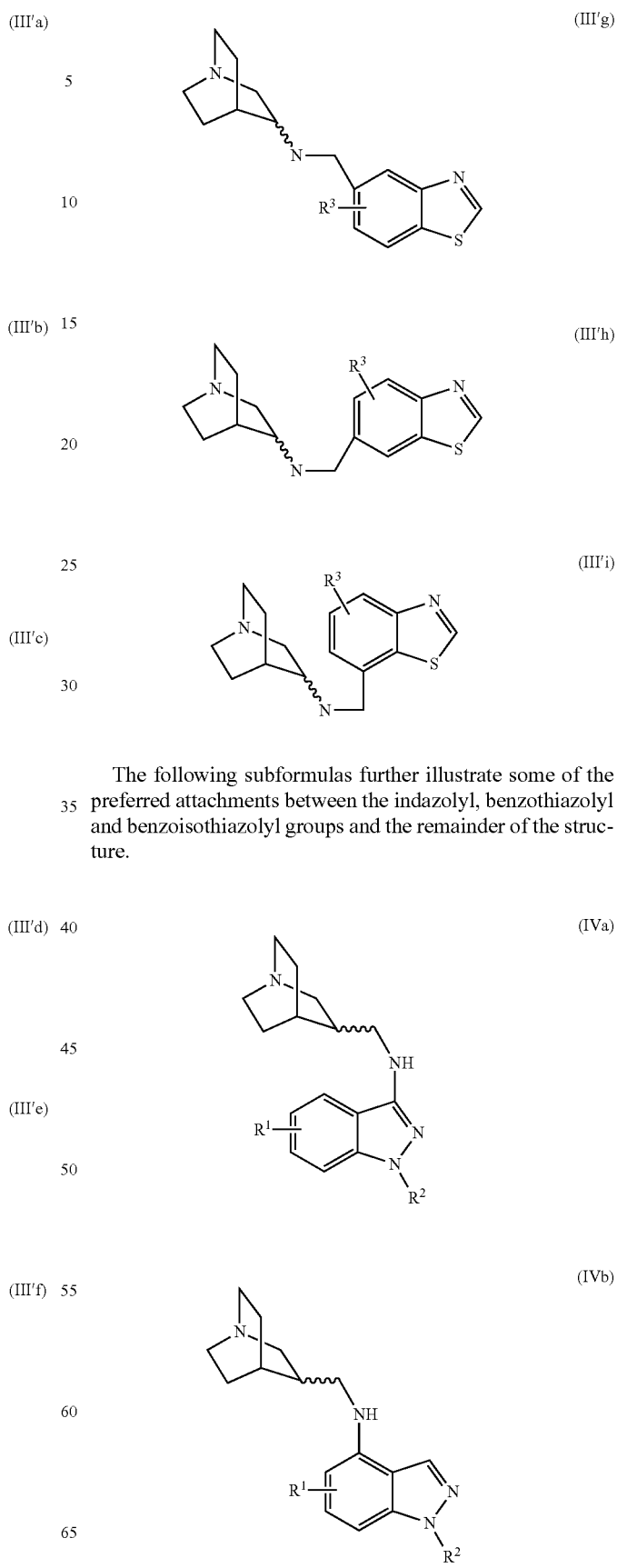
The following subformulas further illustrate some of the preferred attachments between the indazolyl, benzothiazolyl and benzoisothiazolyl groups and the remainder of the structure.

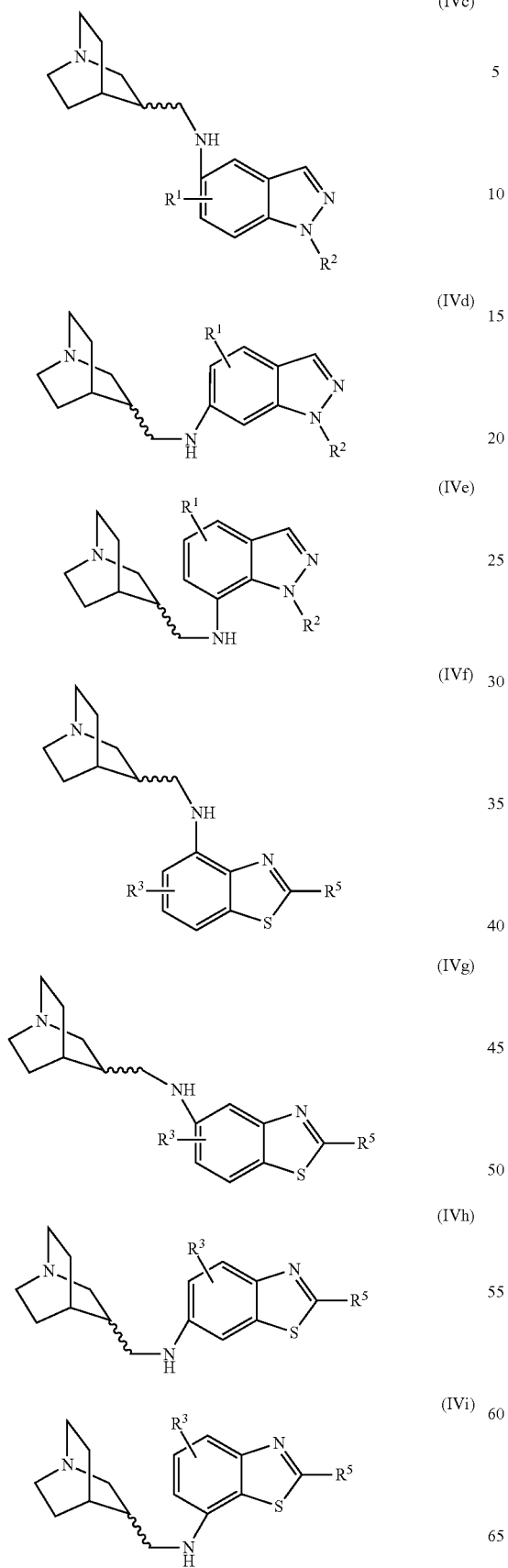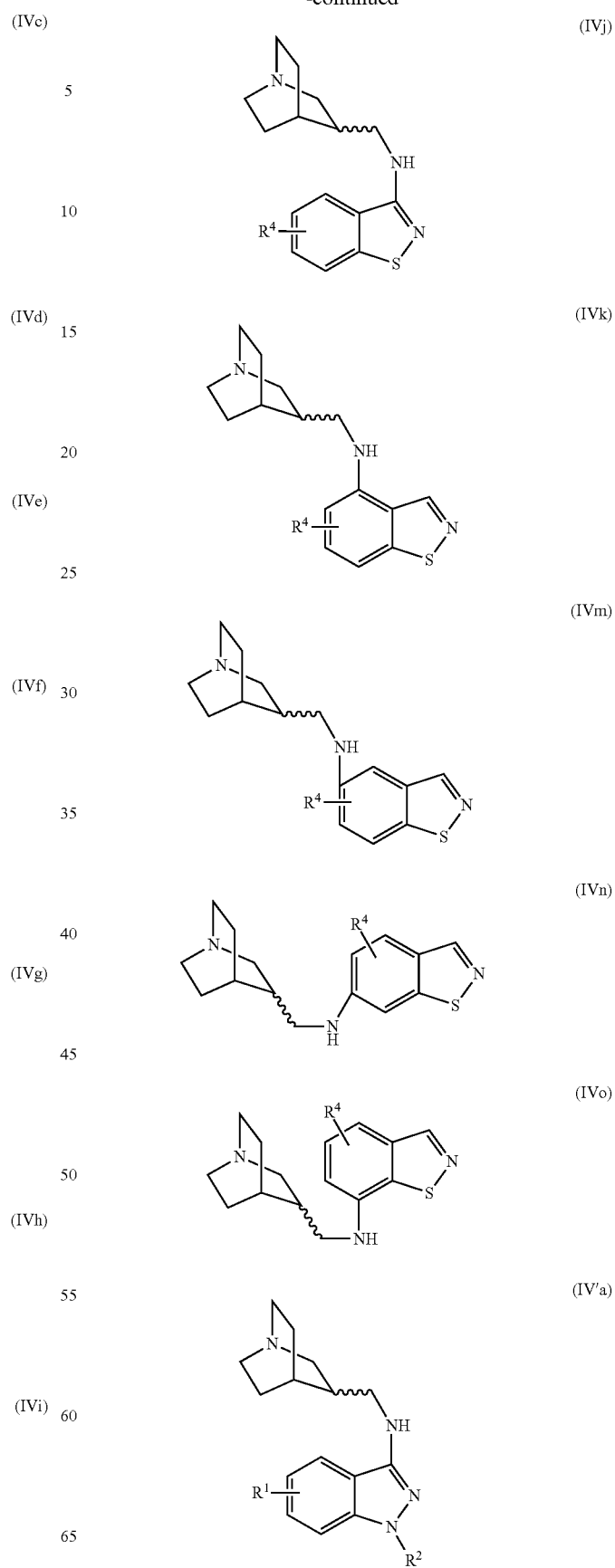

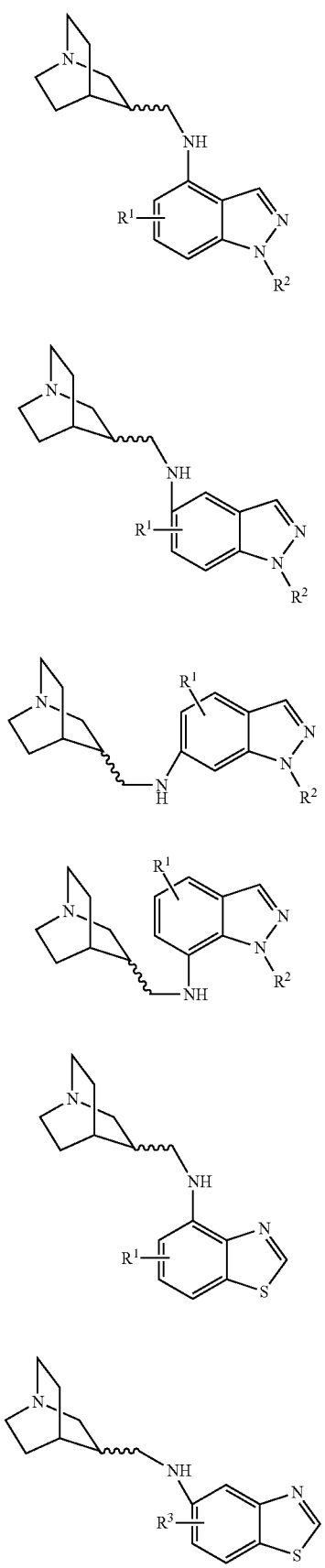
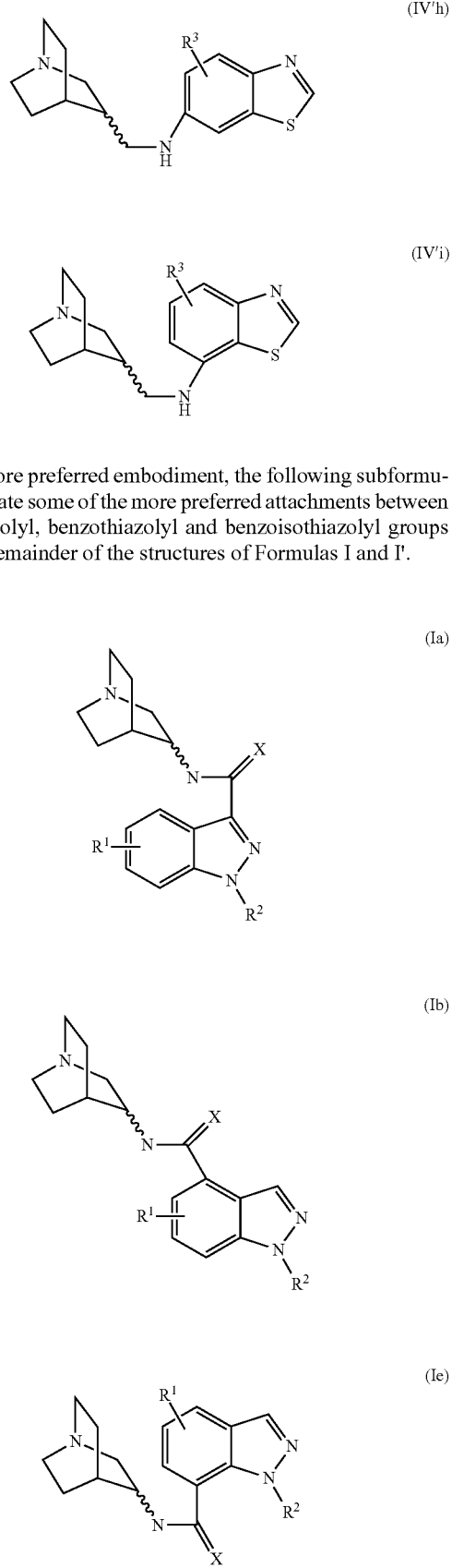
In a more preferred embodiment, the following subformulas illustrate some of the more preferred attachments between the indazolyl, benzothiazolyl and benzoisothiazolyl groups and the remainder of the structures of Formulas I and I'.

-continued (If) 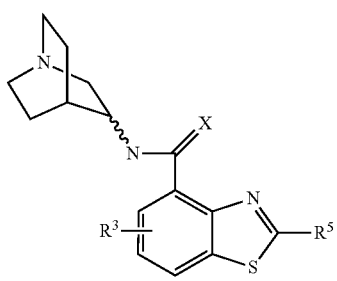

(Ii) 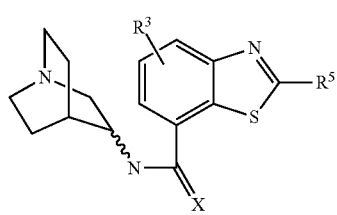

(Ij) 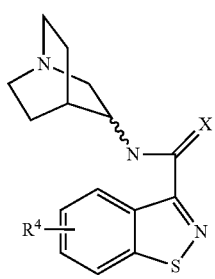

(Ik) 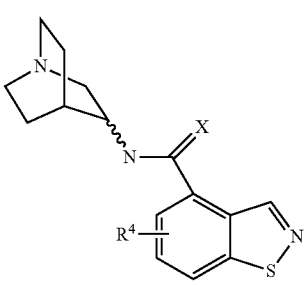

(Io) 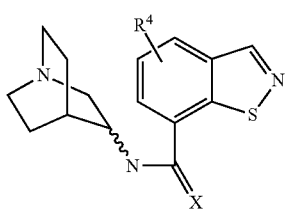

(I'a) 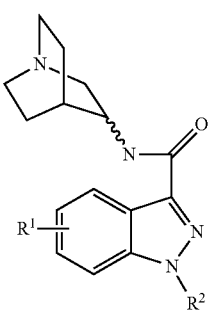

(I'b) 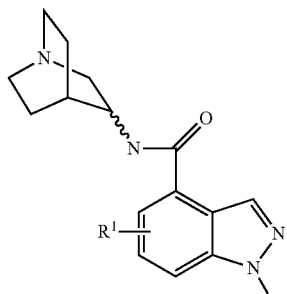

(I'e) 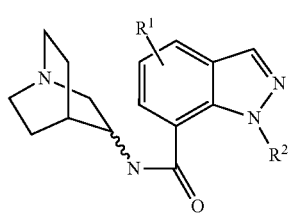

(I'f) 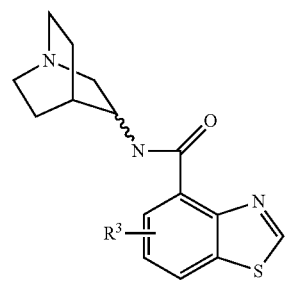

(I'i) 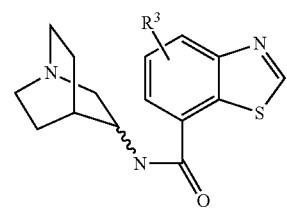

In accordance with a method aspect of the invention, there is provided a method of treating a patient (e.g., a mammal such as a human) suffering from a disease state (e.g., memory impairment) comprising administering to the patient a compound according to Formulas I-IV or I'-IV'. Preferably, the disease state involves decreased nicotinic acetylcholine receptor activity.

In accordance with a method aspect of the invention there is provided a method for the treatment or prophylaxis of a disease or condition resulting from dysfunction of nicotinic acetylcholine receptor transmission in a mammal, a human, comprising administering an effective amount of a compound according to Formulas I-IV or I'-IV'.

In accordance with a method aspect of the invention there is provided a method for the treatment or prophylaxis of a disease or condition resulting from defective or malfunctioning nicotinic acetylcholine receptors, particularly α7nACh receptors, in a mammal, a human, comprising administering an effective amount of a compound according to Formulas I-IV or I'-IV'.

In accordance with a method aspect of the invention there is provided a method for the treatment or prophylaxis of a disease or condition resulting from suppressed nicotinic acetylcholine receptor transmission in a mammal, e.g., a human, comprising administering an amount of a compound according to Formulas I-IV or I'-IV' effective to activate α7nACh receptors.

In accordance with another method aspect of the invention there is provided a method for the treatment or prophylaxis of a psychotic disorder, a cognition impairment (e.g., memory impairment), or neurodegenerative disease in a mammal, e.g., a human, comprising administering an effective amount of a compound according to Formulas I-IV or I'-IV'.

In accordance with another method aspect of the invention there is provided a method for the treatment or prophylaxis of a disease or condition resulting from loss of cholinergic synapses in a mammal, e.g., a human, comprising administering an effective amount of a compound according to Formulas I-IV or I'-IV'.

In accordance with another method aspect of the invention there is provided a method for the treatment or prophylaxis of a neurodegenerative disorder by activation of α7nACh receptors in a mammal, e.g., a human, comprising administering an effective amount of a compound according to Formulas I-IV or I'-IV'.

In accordance with another method aspect of the invention there is provided a method for protecting neurons in a mammal, e.g., a human, from neurotoxicity induced by activation of α7nACh receptors comprising administering an effective amount of a compound according to Formulas I-IV or I'-IV'.

In accordance with another method aspect of the invention there is provided a method for the treatment or prophylaxis of a neurodegenerative disorder by inhibiting the binding of Aβ peptides to α7nACh receptors in a mammal, e.g., a human, comprising administering an effective amount of a compound according to Formulas I-IV or I'-IV'.

In accordance with another method aspect of the invention there is provided a method for protecting neurons in a mammal, e.g., a human, from neurotoxicity induced by Aβ peptides comprising administering an effective amount of a compound according to Formulas I-IV or I'-IV'.

In accordance with another method aspect of the invention there is provided a method for alleviating inhibition of cholinergic function induced by Aβ peptides, in a mammal, e.g., a human, comprising administering an effective amount of a compound according to Formulas I-IV or I'-IV'.

The compounds of the present invention are nicotinic alpha-7 ligands, preferably agonists, especially partial agonists, for the alpha-7 nicotinic acetylcholine receptor. Assays for determining nicotinic acetylcholine activity are known within the art. See, e.g., Davies, A. R., et al., *Characterisation of the binding of [3H]methyllycaconitine: a new radioligand for labelling alpha 7-type neuronal nicotinic acetylcholine receptors*. Neuropharmacology, 1999. 38(5): p. 679-90. As agonists for α-7 nAChRs, the compounds are useful in the prophylaxis and treatment of a variety of diseases and conditions associated with the central nervous system. Nicotinic acetylcholine receptors are ligand-gastrol ion-channel receptors that are composed of five subunit proteins which form a central ion-conducting pore. Presently, there are eleven known neuronal nAChR subunits (α2-α9 and β2-β4). There are also five further subunits expressed in the peripheral nervous system (α1, β1, γ, δ, ε).

The nAChR receptor subtypes can be homopentameric or heteropentameric. The subtype which has received considerable attention is the homopentameric α7 receptor subtype formed from five α7 subunits. The α7nAChRs exhibit a high affinity for nicotine (agonist) and for α-bungarotoxin (antagonist). Studies have shown the α7-nAChR agonists can be useful in the treatment of psychotic diseases, neurodegenerative diseases, and cognitive impairments, among other things. While nicotine is a known agonist, there is a need for the development of other α7-nAChR agonists, especially selective agonists, that are less toxic or exhibit fewer side effects than nicotine.

The compound anabaseine, i.e., 2-(3-pyridyl)-3,4,5,6-tetrahydropyridine is a naturally occurring toxin in certain marine worms (nemertine worms) and ants. See, e.g., Kern et al., Toxicon, 9:23, 1971. Anabaseine is a potent activator of mammalian nicotinic receptors. See, e.g., Kem, Amer. Zoologist, 25, 99, 1985. Certain anabaseine analogs such as anabasine and DMAB (3-[4-(dimethylamino)benzylidene]-3,4,5,6-tetrahydro-2',3'-bipyridine) are also known nicotinic receptor agonists. See, e.g., U.S. Pat. No. 5,602,257 and WO 92/15306. One particular anabaseine analog, (E-3-[2,4-dimethoxy-benzylidene]-anabeseine, also known as GTS-21 and DMXB (see, e.g., U.S. Pat. No. 5,741,802), is a selective partial α7-nAChR agonist that has been studied extensively. For example, abnormal sensory inhibition is a sensory processing deficit in schizophrenics and GTS-21 has been found to increase sensory inhibition through interaction with α7-nAChRs. See, e.g., Stevens et al., Psychopharmacology, 136: 320-27 (1998).

Another compound which is known to be a selective α7-nAChR agonist is Tropisetron, i.e., 1αH, 5αH-tropan-3α-yl indole-3-carboxylate. See J. E. Macor et al., *The 5-HT3-Antagonist Tropisetron (ICS 205-930) is a Potent and Selective A7 Nicotinic Receptor Partial Agonist*. Bioorg. Med. Chem. Lett. 2001, 319-321).

Alkyl throughout means a straight-chain or branched-chain aliphatic hydrocarbon radical having preferably 1 to 4 carbon atoms. Suitable alkyl groups include methyl, ethyl, propyl, isopropyl, butyl, sec-butyl, and tert-butyl.

Alkoxy means alkyl-O— groups in which the alkyl portion preferably has 1 to 4 carbon atoms. Suitable alkoxy groups include methoxy, ethoxy, propoxy, isopropoxy, isobutoxy, and sec-butoxy.

Alkylthio means alkyl-S— groups in which the alkyl portion preferably has 1 to 4 carbon atoms. Suitable alkylthio groups include methylthio and ethylthio.

Cycloalkyl means a cyclic, bicyclic or tricyclic saturated hydrocarbon radical having 3 to 7 carbon atoms. Suitable cycloalkyl groups include cyclopropyl, cyclobutyl, cyclopentyl, and cyclohexyl. Other suitable cycloalkyl groups include spiropentyl, bicyclo[2.1.0]pentyl, and bicyclo[3.1.0]hexyl.

Cycloalkoxy means cycloalkyl-O— groups in which the cycloalkyl portion preferably is a cyclic, bicyclic or tricyclic saturated hydrocarbon radical having 3 to 7 carbon atoms.

Cycloalkylalkyl groups contain 4 to 7 carbon atoms; for example, cyclopropylmethyl, cyclopropylethyl, cyclobutylmethyl, and cyclopentylmethyl.

Cycloalkylalkoxy groups contain 4 to 7 carbon atoms, for example, cyclopropylmethyloxy, cyclopropylethyloxy, cyclobutylmethyloxy, and cyclopentylmethyloxy.

The cycloalkyl and cycloalkylalkyl groups can be substituted by $C_{1-4}$-alkyl, $C_{1-4}$-alkoxy, hydroxyl, amino, monoalkylamino having 1 to 4 carbon atoms, and/or dialkylamino in which each alkyl group has 1 to 4 carbon atoms.

Aryl, as a group or substituent per se or as part of a group or substituent, refers to an aromatic carbocyclic radical containing 6 to 10 carbon atoms, unless indicated otherwise. Suitable aryl groups include phenyl, napthyl and biphenyl. Substituted aryl groups include the above-described aryl groups which are substituted one or more times by halogen, alkyl, hydroxy, alkoxy, nitro, methylenedioxy, ethylenedioxy, amino, alkylamino, dialkylamino, hydroxyalkyl, hydroxyalkoxy, carboxy, cyano, acyl, alkoxycarbonyl, alkylthio, alkylsulphinyl, alkylsulphonyl, phenoxy, and acyloxy (e.g., acetoxy).

Heterocyclic groups refer to saturated, partially saturated and fully unsaturated heterocyclic groups having one, two or three rings and a total number of 5 to 10 ring atoms wherein at least one of the ring atoms is an N, O or S atom. Preferably, the heterocyclic group contains 1 to 3 hetero-ring atoms selected from N, O and S. Suitable saturated and partially saturated heterocyclic groups include, but are not limited to tetrahydrofuranyl, tetrahydrothienyl, pyrrolidinyl, piperidinyl, piperazinyl, morpholinyl, isoxazolinyl and the like. Suitable heteroaryl groups include but are not limited to furyl, thienyl, pyrrolyl, pyrazolyl, imidazolyl, pyridyl, pyrimidinyl, indolyl, quinolinyl, isoquinolinyl, naphthyridinyl and the like. Other examples of suitable heterocyclic groups, are 2-quinolinyl, 1,3-benzodioxyl, 2-thienyl, 2-benzofuranyl, 2-benzothiophenyl, 3-thienyl, 2,3-dihydro-5-benzofuranyl, 4-indoyl, 4-pyridyl, 3-quinolinyl, 4-quinolinyl, 1,4-benzodioxan-6-yl, 3-indoyl, 2-pyrrolyl, 3,4-1,2-benzopyran-6-yl, 5-indolyl, 1,5-benzoxepin-8-yl, 3-pyridyl, 6-coumarinyl, 5-benzofuranyl, 2-isoimidazol-4-yl, 3-pyrazolyl, and 3-carbazolyl.

Substituted heterocyclic groups refer to the heterocyclic groups described above, which are substituted in one or more places by, for example, halogen, aryl, alkyl, alkoxy, cyano, trifluoromethyl, nitro, oxo, amino, alkylamino, and dialkylamino.

Radicals which are substituted one or more times preferably have 1 to 3 substituents, especially 1 or 2 substituents of the exemplified substituents. Halogenated radicals such as halogenated alkyls are preferably fluorinated and include perhalo radicals such as trifluoromethyl.

In the compounds of Formulas I-IV and I'-IV', $R^1$ is preferably H, F, Cl, Br, methyl, methoxy, or amino, $R^2$ is preferably H or methyl, and $R^3$ is preferably H, F, Cl, Br, methyl, methoxy, or amino.

Also, in the compounds of Formulas I-IV and I'-IV', $R^1$ is preferably H, F, Cl, Br, 2-thiophenyl, 3-thiophenyl, 3-furyl, or phenyl, $R^2$ is preferably H, methyl 2-thiophenyl, 3-thiophenyl, 3-furyl, or phenyl, and $R^3$ is preferably H, F, Cl, Br, 2-thiophenyl, 3-thiophenyl, 3-furyl, or phenyl.

Also, in the compounds of Formulas I-IV, $R^4$ is preferably H, F, Cl, Br, 2-thiophenyl, 3-thiophenyl, 3-furyl, phenyl, or methoxy.

Also, in the compounds of Formulas I-IV, $R^5$ is preferably H.

According to a compound aspect of the invention, the compound of formulas I-IV is selected from:

N-(1-Azabicyclo[2.2.2]oct-3-yl)benzo[d]isothiazole-3-carboxamide,
N-(1-Azabicyclo[2.2.2]oct-3-yl)benzo[d]isothiazole-3-carboxamide hydrochloride,
N-((3R)-1-Azabicyclo[2.2.2]oct-3-yl)benzo[d]isothiazole-3-carboxamide,
N-((3R)-1-Azabicyclo[2.2.2]oct-3-yl)benzo[d]isothiazole-3-carboxamide hydrochloride,
N-((3S)-1-Azabicyclo[2.2.2]oct-3-yl)benzo[d]isothiazole-3-carboxamide,
N-((3S)-1-Azabicyclo[2.2.2]oct-3-yl)benzo[d]isothiazole-3-carboxamide hydrochloride,
N-(1-Azabicyclo[2.2.2]oct-3-yl)-1H-indazole-3-carboxamide,
N-(-1-Azabicyclo[2.2.2]oct-3-yl)-1H-indazole-3-carboxamide hydrochloride,
N-((3R)-1-Azabicyclo[2.2.2]oct-3-yl)-1H-indazole-3-carboxamide,
N-((3R)-1-Azabicyclo[2.2.2]oct-3-yl)-1H-indazole-3-carboxamide hydrochloride,
N-((3S)-1-Azabicyclo[2.2.2]oct-3-yl)-1H-indazole-3-carboxamide,
N-((3S)-1-Azabicyclo[2.2.2]oct-3-yl)-1H-indazole-3-carboxamide hydrochloride,
1-Methyl-1H-Indazole-3-carboxamide, N-1-aza-bicyclo[2,2,2]oct-3-yl,
(R) 1-Methyl-1H-Indazole-3-carboxamide, N-1-aza-bicyclo[2,2,2]oct-3-yl,
(S) 1-Methyl-1H-Indazole-3-carboxamide, N-1-aza-bicyclo[2,2,2]oct-3-yl,
N-(1-Azabicyclo[2.2.2]oct-3-yl)-5-(bromo)benzo[d]isothiazole-3-carboxamide,
N-(1-Azabicyclo[2.2.2]oct-3-yl)-5-(methoxy)benzo[d]isothiazole-3-carboxamide hydroformate,
N-(1-Azabicyclo[2.2.2]oct-3-yl)-5-(bromo)-1H-indazole-3-carboxamide,
N-(1-Azabicyclo[2.2.2]oct-3-yl)-5-(cyclopropyl)-1H-indazole-3-carboxamide hydroformate,
N-(1-Azabicyclo[2.2.2]oct-3-yl)-5-(furan-3-yl)-1H-indazole-3-carboxamide hydroformate,
N-(1-Azabicyclo[2.2.2]oct-3-yl)-5-(phenyl)-1H-indazole-3-carboxamide hydroformate,
N-(1-Azabicyclo[2.2.2]oct-3-yl)-5-(thiophen-2-yl)-1H-indazole-3-carboxamide,
N-(1-Azabicyclo[2.2.2]oct-3-yl)-5-(thiophen-2-yl)-1H-indazole-3-carboxamide hydroformate,
N-(1-Azabicyclo[2.2.2]oct-3-yl)-5-(thiophen-3-yl)-1H-indazole-3-carboxamide hydroformate,
N-((3R)-1-Azabicyclo[2.2.2]oct-3-yl)-5-(bromo)benzo[d]isothiazole-3-carboxamide,
N-((3R)-1-Azabicyclo[2.2.2]oct-3-yl)-5-(methoxy)benzo[d]isothiazole-3-carboxamide hydroformate,
N-((3R)-1-Azabicyclo[2.2.2]oct-3-yl)-5-(bromo)-1H-indazole-3-carboxamide,
N-((3R)-1-Azabicyclo[2.2.2]oct-3-yl)-5-(cyclopropyl)-1H-indazole-3-carboxamide hydroformate,
N-((3R)-1-Azabicyclo[2.2.2]oct-3-yl)-5-(furan-3-yl)-1H-indazole-3-carboxamide hydroformate,
N-((3R)-1-Azabicyclo[2.2.2]oct-3-yl)-5-(phenyl)-1H-indazole-3-carboxamide hydroformate,
N-((3R)-1-Azabicyclo[2.2.2]oct-3-yl)-5-(thiophen-2-yl)-1H-indazole-3-carboxamide,
N-((3R)-1-Azabicyclo[2.2.2]oct-3-yl)-5-(thiophen-2-yl)-1H-indazole-3-carboxamide hydroformate,
N-((3R)-1-Azabicyclo[2.2.2]oct-3-yl)-5-(thiophen-3-yl)-1H-indazole-3-carboxamide hydroformate,
N-((3S)-1-Azabicyclo[2.2.2]oct-3-yl)-5-(bromo)benzo[d]isothiazole-3-carboxamide,
N-((3S)-1-Azabicyclo[2.2.2]oct-3-yl)-5-methoxybenzo[d]isothiazole-3-carboxamide hydroformate,
N-((3S)-1-Azabicyclo[2.2.2]oct-3-yl)-5-(bromo)-1H-indazole-3-carboxamide,
N-((3S)-1-Azabicyclo[2.2.2]oct-3-yl)-5-(furan-3-yl)-1H-indazole-3-carboxamide hydroformate,
N-((3S)-1-Azabicyclo[2.2.2]oct-3-yl)-5-(phenyl)-1H-indazole-3-carboxamide hydroformate,
N-((3S)-1-Azabicyclo[2.2.2]oct-3-yl)-5-(thiophen-2-yl)-1H-indazole-3-carboxamide hydroformate,
N-((3S)-1-Azabicyclo[2.2.2]oct-3-yl)-5-(thiophen-3-yl)-1H-indazole-3-carboxamide hydroformate,
N-(1-Azabicyclo[2.2.2]oct-3-yl)-6-bromobenzo[d]isothiazole-3-carboxamide,
N-(1-Azabicyclo[2.2.2]oct-3-yl)-6-cyclopropylbenzo[d]isothiazole-3-carboxamide, N-(1-Azabicyclo[2.2.2]oct-3-yl)-6-(2-fluorophenyl)benzo[d]isothiazole-3-carboxamide,
N-(1-Azabicyclo[2.2.2]oct-3-yl)-6-(2-fluorophenyl)benzo[d]isothiazole-3-carboxamide hydroformate,
N-((1-Azabicyclo[2.2.2]oct-3-yl)-6-(3-fluorophenyl)benzo[d]isothiazole-3-carboxamide,
N-(1-Azabicyclo[2.2.2]oct-3-yl)-6-(3-fluorophenyl)benzo[d]isothiazole-3-carboxamide hydroformate,
N-((1-Azabicyclo[2.2.2]oct-3-yl)-6-(4-fluorophenyl)benzo[d]isothiazole-3-carboxamide,
N-(1-Azabicyclo[2.2.2]oct-3-yl)-6-(4-fluorophenyl)benzo[d]isothiazole-3-carboxamide hydroformate,
N-((1-Azabicyclo[2.2.2]oct-3-yl)-6-(3-furan-3-yl)benzo[d]isothiazole-3-carboxamide,
N-(1-Azabicyclo[2.2.2]oct-3-yl)-6-(3-furan-3-yl)benzo[d]isothiazole-3-carboxamide hydroformate,
N-(1-Azabicyclo[2.2.2]oct-3-yl)-6-methoxybenzo[d]isothiazole-3-carboxamide,
N-(1-Azabicyclo[2.2.2]oct-3-yl)-6-(morpholin-4-yl)benzo[d]isothiazole-3-carboxamide hydroformate,
N-(1-Azabicyclo[2.2.2]oct-3-yl)-6-phenylbenzo[d]isothiazole-3-carboxamide,
N-(1-Azabicyclo[2.2.2]oct-3-yl)-6-phenylbenzo[d]isothiazole-3-carboxamide hydroformate,
N-(1-Azabicyclo[2.2.2]oct-3-yl)-6-(pyridin-3-yl)benzo[d]isothiazole-3-carboxamide,
N-(1-Azabicyclo[2.2.2]oct-3-yl)-6-(pyridin-3-yl)benzo[d]isothiazole-3-carboxamide hydroformate,
N-(1-Azabicyclo[2.2.2]oct-3-yl)-6-(pyridin-4-yl)benzo[d]isothiazole-3-carboxamide,
N-(1-Azabicyclo[2.2.2]oct-3-yl)-6-(pyridin-4-yl)benzo[d]isothiazole-3-carboxamide hydroformate,
N-(1-Azabicyclo[2.2.2]oct-3-yl)-6-(thiophen-2-yl)benzo[d]isothiazole-3-carboxamide,
N-(1-Azabicyclo[2.2.2]oct-3-yl)-6-(thiophen-3-yl)benzo[d]isothiazole-3-carboxamide,
N-(1-Azabicyclo[2.2.2]oct-3-yl)-6-(bromo)-1H-indazole-3-carboxamide,
N-(1-Azabicyclo[2.2.2]oct-3-yl)-6-(furan-3-yl)-1H-indazole-3-carboxamide hydroformate,
N-((1-Azabicyclo[2.2.2]oct-3-yl)-6-(phenyl)-1H-indazole-3-carboxamide hydroformate,
N-(1-Azabicyclo[2.2.2]oct-3-yl)-6-(thiophen-2-yl)-1H-indazole-3-carboxamide hydroformate,
N-(1-Azabicyclo[2.2.2]oct-3-yl)-6-(thiophen-3-yl)-1H-indazole-3-carboxamide hydroformate,
N-((3R)-1-Azabicyclo[2.2.2]oct-3-yl)-6-bromobenzo[d]isothiazole-3-carboxamide,
N-((3R)-1-Azabicyclo[2.2.2]oct-3-yl)-6-cyclopropylbenzo[d]isothiazole-3-carboxamide,
N-((3R)-1-Azabicyclo[2.2.2]oct-3-yl)-6-(2-fluorophenyl)benzo[d]isothiazole-3-carboxamide,
N-((3R)-1-Azabicyclo[2.2.2]oct-3-yl)-6-(2-fluorophenyl)benzo[d]isothiazole-3-carboxamide hydroformate,
N-((3R)-1-Azabicyclo[2.2.2]oct-3-yl)-6-(3-fluorophenyl)benzo[d]isothiazole-3-carboxamide,
N-((3R)-1-Azabicyclo[2.2.2]oct-3-yl)-6-(3-fluorophenyl)benzo[d]isothiazole-3-carboxamide hydroformate,
N-((3R)-1-Azabicyclo[2.2.2]oct-3-yl)-6-(4-fluorophenyl)benzo[d]isothiazole-3-carboxamide,
N-((3R)-1-Azabicyclo[2.2.2]oct-3-yl)-6-(4-fluorophenyl)benzo[d]isothiazole-3-carboxamide hydroformate,
N-((3R)-1-Azabicyclo[2.2.2]oct-3-yl)-6-(3-furan-3-yl)benzo[d]isothiazole-3-carboxamide,
N-((3R)-1-Azabicyclo[2.2.2]oct-3-yl)-6-(3-furan-3-yl)benzo[d]isothiazole-3-carboxamide,
N-((3R)-1-Azabicyclo[2.2.2]oct-3-yl)-6-methoxybenzo[d]isothiazole-3-carboxamide,
N-((3R)-1-Azabicyclo[2.2.2]oct-3-yl)-6-(morpholin-4-yl)benzo[d]isothiazole-3-carboxamide hydroformate,
N-((3R)-1-Azabicyclo[2.2.2]oct-3-yl)-6-phenylbenzo[d]isothiazole-3-carboxamide,
N-((3R)-1-Azabicyclo[2.2.2]oct-3-yl)-6-phenylbenzo[d]isothiazole-3-carboxamide hydroformate,
N-((3R)-1-Azabicyclo[2.2.2]oct-3-yl)-6-(pyridin-3-yl)benzo[d]isothiazole-3-carboxamide,
N-((3R)-1-Azabicyclo[2.2.2]oct-3-yl)-6-(pyridin-3-yl)benzo[d]isothiazole-3-carboxamide hydroformate,
N-((3R)-1-Azabicyclo[2.2.2]oct-3-yl)-6-(pyridin-4-yl)benzo[d]isothiazole-3-carboxamide,
N-((3R)-1-Azabicyclo[2.2.2]oct-3-yl)-6-(pyridin-4-yl)benzo[d]isothiazole-3-carboxamide hydroformate,
N-((3R)-1-Azabicyclo[2.2.2]oct-3-yl)-6-(thiophen-2-yl)benzo[d]isothiazole-3-carboxamide,
N-((3R)-1-Azabicyclo[2.2.2]oct-3-yl)-6-(thiophen-3-yl)benzo[d]isothiazole-3-carboxamide,
N-((3R)-1-Azabicyclo[2.2.2]oct-3-yl)-6-(bromo)-1H-indazole-3-carboxamide,
N-((3R)-1-Azabicyclo[2.2.2]oct-3-yl)-6-(furan-3-yl)-1H-indazole-3-carboxamide hydroformate,
N-((3R)-1-Azabicyclo[2.2.2]oct-3-yl)-6-(phenyl)-1H-indazole-3-carboxamide hydroformate,
N-((3R)-1-Azabicyclo[2.2.2]oct-3-yl)-6-(thiophen-2-yl)-1H-indazole-3-carboxamide hydroformate,
N-((3R)-1-Azabicyclo[2.2.2]oct-3-yl)-6-(thiophen-3-yl)-1H-indazole-3-carboxamide hydroformate,
N-((3S)-1-Azabicyclo[2.2.2]oct-3-yl)-6-bromobenzo[d]isothiazole-3-carboxamide,
N-((3S)-1-Azabicyclo[2.2.2]oct-3-yl)-6-cyclopropylbenzo[d]isothiazole-3-carboxamide,
N-((3S)-1-Azabicyclo[2.2.2]oct-3-yl)-6-(2-fluorophenyl)benzo[d]isothiazole-3-carboxamide hydroformate,
N-((3S)-1-Azabicyclo[2.2.2]oct-3-yl)-6-(3-fluorophenyl)benzo[d]isothiazole-3-carboxamide hydroformate,
N-((3S)-1-Azabicyclo[2.2.2]oct-3-yl)-6-(4-fluorophenyl)benzo[d]isothiazole-3-carboxamide hydroformate,
N-((3S)-1-Azabicyclo[2.2.2]oct-3-yl)-6-(furan-3-yl)benzo[d]isothiazole-3-carboxamide,
N-((3S)-1-Azabicyclo[2.2.2]oct-3-yl)-6-methoxybenzo[d]isothiazole-3-carboxamide,
N-((3S)-1-Azabicyclo[2.2.2]oct-3-yl)-6-(morpholin-4-yl)benzo[d]isothiazole-3-carboxamide hydroformate,
N-((3S)-1-Azabicyclo[2.2.2]oct-3-yl)-6-phenylbenzo[d]isothiazole-3-carboxamide hydroformate,
N-((3S)-1-Azabicyclo[2.2.2]oct-3-yl)-6-(pyridin-3-yl)benzo[d]isothiazole-3-carboxamide hydroformate,
N-((3S)-1-Azabicyclo[2.2.2]oct-3-yl)-6-(pyridin-4-yl)benzo[d]isothiazole-3-carboxamide hydroformate,
N-((3S)-1-Azabicyclo[2.2.2]oct-3-yl)-6-(thiophen-2-yl)benzo[d]isothiazole-3-carboxamide hydroformate,
N-((3S)-1-Azabicyclo[2.2.2]oct-3-yl)-6-(thiophen-3-yl)benzo[d]isothiazole-3-carboxamide,
N-((3S)-1-Azabicyclo[2.2.2]oct-3-yl)-6-(bromo)-1H-indazole-3-carboxamide,
N-((3S)-1-Azabicyclo[2.2.2]oct-3-yl)-6-(furan-3-yl)-1H-indazole-3-carboxamide hydroformate,
N-((3S)-1-Azabicyclo[2.2.2]oct-3-yl)-6-(phenyl)-1H-indazole-3-carboxamide hydroformate,
N-((3S)-1-Azabicyclo[2.2.2]oct-3-yl)-6-(thiophen-2-yl)-1H-indazole-3-carboxamide hydroformate,
N-((3S)-1-Azabicyclo[2.2.2]oct-3-yl)-6-(thiophen-3-yl)-1H-indazole-3-carboxamide hydroformate, N-(1-Azabicyclo[2.2.2]oct-3-yl)-7-methoxybenzo[d]isothiazole-3-carboxamide,
N-((3R)-1-Azabicyclo[2.2.2]oct-3-yl)-7-methoxybenzo[d]isothiazole-3-carboxamide,
N-((3S)-1-Azabicyclo[2.2.2]oct-3-yl)-7-methoxybenzo[d]isothiazole-3-carboxamide,
N-(1-Azabicyclo[2,2,2]oct-3-yl)-N-(1H-indazol-3-ylmethyl)amine,
N-((3R)-1-Azabicyclo[2,2,2]oct-3-yl)-N-(1H-indazol-3-ylmethyl)amine,
N-((3S)-1-Aza-bicyclo[2,2,2]oct-3-yl)-N-(1H-indazol-3-ylmethyl)amine,
N-(1-Aza-bicyclo[2.2.2]oct-3-yl)benzothiazole-4-carboxamide dihydrochloride,
N-((3R)-1-Aza-bicyclo[2.2.2]oct-3-yl)benzothiazole-4-carboxamide dihydrochloride,
N-((3S)-1-Aza-bicyclo[2.2.2]oct-3-yl)benzothiazole-4-carboxamide dihydrochloride,
N-(1-Azabicyclo[2.2.2]oct-3-yl)-1H-indazole-4-carboxamide,
N-((3R)-1-Azabicyclo[2.2.2]oct-3-yl)-1H-indazole-4-carboxamide,
N-((3S)-1-Azabicyclo[2.2.2]oct-3-yl)-1H-indazole-4-carboxamide,
N-(1H-Indazol-4-yl)-1-azabicyclo[2,2,2]oct-3-ylcarboxamide,
N-(1-Azabicyclo[2,2,2]oct-3-yl)-N-(1H-indazol-4-ylmethyl)amine,
N-(1-Azabicyclo[2,2,2]oct-3-yl)benzothiazole-5-carboxamide,
N-(1-Azabicyclo[2,2,2]oct-3-yl)benzothiazole-5-carboxamide hydrochloride,
N-((3R)-1-Azabicyclo[2,2,2]oct-3-yl)benzothiazole-5-carboxamide,
N-((3R)-1-Azabicyclo[2,2,2]oct-3-yl)benzothiazole-5-carboxamide hydrochloride,
N-((3S)-1-Azabicyclo[2,2,2]oct-3-yl)benzothiazole-5-carboxamide,
N-((3S)-1-Azabicyclo[2,2,2]oct-3-yl)benzothiazole-5-carboxamide hydrochloride,
N-(1-Azabicyclo[2.2.2]oct-3-yl)-1H-indazole-5-carboxamide,
N-((3R)-1-Azabicyclo[2.2.2]oct-3-yl)-1H-indazole-5-carboxamide,
N-((3S)-1-Azabicyclo[2.2.2]oct-3-yl)-1H-indazole-5-carboxamide,
N-(1H-Indazol-5-yl)-1-aza-bicyclo[2.2.2]oct-3-ylcarboxamide,
N-(1-Azabicyclo[2,2,2]oct-3-yl)benzothiazole-6-carboxamide,
N-(1-Azabicyclo[2,2,2]oct-3-yl)benzothiazole-6-carboxamide hydrochloride,
N-((3R)-1-Azabicyclo[2,2,2]oct-3-yl)benzothiazole-6-carboxamide,
N-((3R)-1-Azabicyclo[2,2,2]oct-3-yl)benzothiazole-6-carboxamide hydrochloride,
N-((3S)-1-Azabicyclo[2,2,2]oct-3-yl)benzothiazole-6-carboxamide hydrochloride,
N-((3S)-1-Aza-bicyclo[2.2.2]oct-3-yl)benzothiazole-6-carboxamide,
N-((3R)-1-Azabicyclo[2,2,2]oct-3-yl)-2-pyrrol-1-ylbenzothiazole-6-carboxamide hydroformate,
N-(Benzothiazol-6-yl)-1-Azabicyclo[2,2,2]oct-3-ylcarboxamide,
N-(1-Azabicyclo[2.2.2]oct-3-yl)-1H-indazole-6-carboxamide,
N-((3R)-1-Azabicyclo[2.2.2]oct-3-yl)-1H-indazole-6-carboxamide,
N-((3S)-1-Azabicyclo[2.2.2]oct-3-yl)-1H-indazole-6-carboxamide,
N-((3R)-1-Azabicyclo[2.2.2]oct-3-yl)-3-(thiophen-3-yl)-1H-indazole-6-carboxamide hydroformate,
N-(1H-Indazol-6-yl)-1-Azabicyclo[2,2,2]oct-3-ylcarboxamide,
N-(1-Azabicyclo[2,2,2]oct-3-yl)benzothiazole-7-carboxamide hydrochloride,
N-((3R)-1-Azabicyclo[2,2,2]oct-3-yl)benzothiazole-7-carboxamide hydrochloride,
N-((3S)-1-Azabicyclo[2,2,2]oct-3-yl)benzothiazole-7-carboxamide hydrochloride,
N-(1-Azabicyclo[2.2.2]oct-3-yl)-1H-indazole-7-carboxamide,
N-(1-Azabicyclo[2.2.2]oct-3-yl)-1H-indazole-7-carboxamide hydrochloride,
N-((3R)-1-Azabicyclo[2.2.2]oct-3-yl)-1H-indazole-7-carboxamide,
N-((3R)-1-Azabicyclo[2.2.2]oct-3-yl)-1H-indazole-7-carboxamide hydrochloride,
N-((3S)-1-Azabicyclo[2.2.2]oct-3-yl)-1H-indazole-7-carboxamide,
N-((3S)-1-Azabicyclo[2.2.2]oct-3-yl)-1H-indazole-7-carboxamide hydrochloride,
Benzothiazole-4-carboxamide, N-1-aza-bicyclo[2,2,2]oct-3-yl,
(R) Benzothiazole-4-carboxamide, N-1-aza-bicyclo[2,2,2]oct-3-yl,
(S) Benzothiazole-4-carboxamide, N-1-aza-bicyclo[2,2,2]oct-3-yl,
1-Aza-bicyclo[2,2,2]oct-3-ylcarboxamide, N-1H-indazol-3-yl,
(S) 1-Aza-bicyclo[2,2,2]oct-3-ylcarboxamide, N-1H-indazol-3-yl,
(R) 1-Aza-bicyclo[2,2,2]oct-3-ylcarboxamide, N-1H-indazol-3-yl,
1-Aza-bicyclo[2,2,2]oct-3-ylcarboxamide,
(S) 1-Aza-bicyclo[2,2,2]oct-3-ylcarboxamide, N-1H-indazol-4-yl,
(R) 1-Aza-bicyclo[2,2,2]oct-3-ylcarboxamide, N-1H-indazol-4-yl,
1-Aza-bicyclo[2,2,2]oct-3-ylcarboxamide, N-1H-indazol-5-yl,
(S) 1-Aza-bicyclo[2,2,2]oct-3-ylcarboxamide, N-1H-indazol-5-yl,
(R) 1-Aza-bicyclo[2,2,2]oct-3-ylcarboxamide, N-1H-indazol-5-yl,
1-Aza-bicyclo[2,2,2]oct-3-ylcarboxamide, N-1H-indazol-6-yl,
(S) 1-Aza-bicyclo[2,2,2]oct-3-ylcarboxamide, N-1H-indazol-6-yl,
(R) 1-Aza-bicyclo[2,2,2]oct-3-ylcarboxamide, N-1H-indazol-6-yl,
1-Aza-bicyclo[2,2,2]oct-3-ylcarboxamide, N-1H-indazol-7-yl,
(S) 1-Aza-bicyclo[2,2,2]oct-3-ylcarboxamide, N-1H-indazol-7-yl,
(R) 1-Aza-bicyclo[2,2,2]oct-3-ylcarboxamide, N-1H-indazol-7-yl,
1-Aza-bicyclo[2,2,2]oct-3-ylcarboxamide, benzothiazol-4-yl,
(S) 1-Aza-bicyclo[2,2,2]oct-3-ylcarboxamide, benzothiazol-4-yl,
(R) 1-Aza-bicyclo[2,2,2]oct-3-ylcarboxamide, benzothiazol-4-yl, 1-Aza-bicyclo[2,2,2]-3-ylcarboxamide, benzothiazol-5-yl,
(S) 1-Aza-bicyclo[2,2,2]oct-3-ylcarboxamide, benzothiazol-5-yl,
(R) 1-Aza-bicyclo[2,2,2]oct-3-ylcarboxamide, benzothiazol-5-yl,
1-Aza-bicyclo[2,2,2]oct-3-ylcarboxamide, benzothiazol-6-yl,
(S) 1-Aza-bicyclo[2,2,2]oct-3-ylcarboxamide, benzothiazol-6-yl,
(R) 1-Aza-bicyclo[2,2,2]oct-3-ylcarboxamide, benzothiazol-6-yl,
1-Aza-bicyclo[2,2,2]oct-3-ylcarboxamide, benzothiazol-7-yl,
(S) 1-Aza-bicyclo[2,2,2]oct-3-ylcarboxamide, benzothiazol-7-yl,
(R) 1-Aza-bicyclo[2,2,2]oct-3-ylcarboxamide, benzothiazol-7-yl,
(1-Aza-bicyclo[2,2,2]oct-3-yl)-(1H-indazol-3-ylmethyl)-amine,
(S) (1-Aza-bicyclo[2,2,2]oct-3-yl)-(1H-indazol-3-ylmethyl)-amine,
(R) (1-Aza-bicyclo[2,2,2]oct-3-yl)-(1H-indazol-3-ylmethyl)-amine,
(1-Aza-bicyclo[2,2,2]oct-3-yl)-(1H-indazol-4-ylmethyl)-amine,
(S) (1-Aza-bicyclo[2,2,2]oct-3-yl)-(1H-indazol-4-ylmethyl)-amine,
(R) (1-Aza-bicyclo[2,2,2]oct-3-yl)-(1H-indazol-4-ylmethyl)-amine,
(1-Aza-bicyclo[2,2,2]oct-3-yl)-(1H-indazol-5-ylmethyl)-amine,
(S) (1-Aza-bicyclo[2,2,2]oct-3-yl)-(1H-indazol-5-ylmethyl)-amine,
(R) (1-Aza-bicyclo[2,2,2]oct-3-yl)-(1H-indazol-5-ylmethyl)-amine,
(1-Aza-bicyclo[2,2,2]oct-3-yl)-(1H-indazol-6-ylmethyl)-amine,
(S) (1-Aza-bicyclo[2,2,2]oct-3-yl)-(1H-indazol-6-ylmethyl)-amine,
(R) (1-Aza-bicyclo[2,2,2]oct-3-yl)-(1H-indazol-6-ylmethyl)-amine,
(1-Aza-bicyclo[2,2,2]oct-3-yl)-(1H-indazol-7-ylmethyl)-amine,
(S) (1-Aza-bicyclo[2,2,2]oct-3-yl)-(1H-indazol-7-ylmethyl)-amine,
(R) (1-Aza-bicyclo[2,2,2]oct-3-yl)-(1H-indazol-7-ylmethyl)-amine,
(1-Aza-bicyclo[2,2,2]oct-3-yl)-(benzothiazol-4-ylmethyl)-amine,
(S) (1-Aza-bicyclo[2,2,2]oct-3-yl)-(benzothiazol-4-ylmethyl)-amine,
(R) (1-Aza-bicyclo[2,2,2]oct-3-yl)-(benzothiazol-4-ylmethyl)-amine,
(1-Aza-bicyclo[2,2,2]oct-3-yl)-(benzothiazol-5-ylmethyl)-amine,
(S) (1-Aza-bicyclo[2,2,2]oct-3-yl)-(benzothiazol-5-ylmethyl)-amine,
(R) (1-Aza-bicyclo[2,2,2]oct-3-yl)-(benzothiazol-5-ylmethyl)-amine,
(1-Aza-bicyclo[2,2,2]oct-3-yl)-(benzothiazol-6-ylmethyl)-amine,
(S) (1-Aza-bicyclo[2,2,2]oct-3-yl)-(benzothiazol-6-ylmethyl)-amine,
(R) (1-Aza-bicyclo[2,2,2]oct-3-yl)-(benzothiazol-6-ylmethyl)-amine,
(1-Aza-bicyclo[2,2,2]oct-3-yl)-(benzothiazol-7-ylmethyl)-amine,
(S) (1-Aza-bicyclo[2,2,2]oct-3-yl)-(benzothiazol-7-ylmethyl)-amine,
(R) (1-Aza-bicyclo[2,2,2]oct-3-yl)-(benzothiazol-7-ylmethyl)-amine,
(1-Aza-bicyclo[2,2,2]oct-3-ylmethyl)-(1H-indazol-3-yl)-amine,
(S) (1-Aza-bicyclo[2,2,2]oct-3-ylmethyl)-(1H-indazol-3-yl)-amine,
(R) (1-Aza-bicyclo[2,2,2]oct-3-ylmethyl)-(1H-indazol-3-yl)-amine,
(1-Aza-bicyclo[2,2,2]oct-3-ylmethyl)-(1H-indazol-4-yl)-amine,
(S) (1-Aza-bicyclo[2,2,2]oct-3-ylmethyl)-(1H-indazol-4-yl)-amine,
(R) (1-Aza-bicyclo[2,2,2]oct-3-ylmethyl)-(1H-indazol-4-yl)-amine,
(1-Aza-bicyclo[2,2,2]oct-3-ylmethyl)-(1H-indazol-5-yl)-amine,
(S) (1-Aza-bicyclo[2,2,2]oct-3-ylmethyl)-(1H-indazol-5-yl)-amine,
(R) (1-Aza-bicyclo[2,2,2]oct-3-ylmethyl)-(1H-indazol-5-yl)-amine,
(1-Aza-bicyclo[2,2,2]oct-3-ylmethyl)-(1H-indazol-6-yl)-amine,
(S) (1-Aza-bicyclo[2,2,2]oct-3-ylmethyl)-(1H-indazol-6-yl)-amine,
(R) (1-Aza-bicyclo[2,2,2]oct-3-ylmethyl)-(1H-indazol-6-yl)-amine,
(1-Aza-bicyclo[2,2,2]oct-3-ylmethyl)-(1H-indazol-7-yl)-amine,
(S) (1-Aza-bicyclo[2,2,2]oct-3-ylmethyl)-(1H-indazol-7-yl)-amine,
(R) (1-Aza-bicyclo[2,2,2]oct-3-ylmethyl)-(1H-indazol-7-yl)-amine,
(1-Aza-bicyclo[2,2,2]oct-3-ylmethyl)-(benzothiazol-4-yl)-amine,
(S) (1-Aza-bicyclo[2,2,2]oct-3-ylmethyl)-(benzothiazol-4-yl)-amine,
(R) (1-Aza-bicyclo[2,2,2]oct-3-ylmethyl)-(benzothiazol-4-yl)-amine,
(1-Aza-bicyclo[2,2,2]oct-3-ylmethyl)-(benzothiazol-5-yl)-amine,
(S) (1-Aza-bicyclo[2,2,2]oct-3-ylmethyl)-(benzothiazol-5-yl)-amine,
(R) (1-Aza-bicyclo[2,2,2]oct-3-ylmethyl)-(benzothiazol-5-yl)-amine,
(1-Aza-bicyclo[2,2,2]oct-3-ylmethyl)-(benzothiazol-6-yl)-amine,
(S) (1-Aza-bicyclo[2,2,2]oct-3-ylmethyl)-(benzothiazol-6-yl)-amine,
(R) (1-Aza-bicyclo[2,2,2]oct-3-ylmethyl)-(benzothiazol-6-yl)-amine,
(1-Aza-bicyclo[2,2,2]oct-3-ylmethyl)-(benzothiazol-7-yl)-amine,
(S) (1-Aza-bicyclo[2,2,2]oct-3-ylmethyl)-(benzothiazol-7-yl)-amine,
(R) (1-Aza-bicyclo[2,2,2]oct-3-ylmethyl)-(benzothiazol-7-yl)-amine,
and physiological salts thereof.

According to another preferred compound aspect of the invention, the compound of formulas I-IV is selected from:
N-((3R)-1-Azabicyclo[2.2.2]oct-3-yl)benzo[d]isothiazole-3-carboxamide,
N-((3R)-1-Azabicyclo[2.2.2]oct-3-yl)benzo[d]isothiazole-3-carboxamide hydrochloride,
N-((3S)-1-Azabicyclo[2.2.2]oct-3-yl)benzo[d]isothiazole-3-carboxamide, N-((3S)-1-Azabicyclo[2.2.2]oct-3-yl)benzo[d]isothiazole-3-carboxamide hydrochloride,
N-(1-Azabicyclo[2.2.2]oct-3-yl)-1H-indazole-3-carboxamide,
N-(-1-Azabicyclo[2.2.2]oct-3-yl)-1H-indazole-3-carboxamide hydrochloride,
N-((3R)-1-Azabicyclo[2.2.2]oct-3-yl)-1H-indazole-3-carboxamide,
N-((3R)-1-Azabicyclo[2.2.2]oct-3-yl)-1H-indazole-3-carboxamide hydrochloride,
N-((3S)-1-Azabicyclo[2.2.2]oct-3-yl)-1H-indazole-3-carboxamide,
N-((3S)-1-Azabicyclo[2.2.2]oct-3-yl)-1H-indazole-3-carboxamide hydrochloride,
1-Methyl-1H-Indazole-3-carboxamide, N-1-aza-bicyclo[2,2,2]oct-3-yl,
(R) 1-Methyl-1H-Indazole-3-carboxamide, N-1-aza-bicyclo[2,2,2]oct-3-yl,
(S) 1-Methyl-1H-Indazole-3-carboxamide, N-1-aza-bicyclo[2,2,2]oct-3-yl,
N-((3R)-1-Azabicyclo[2.2.2]oct-3-yl)-5-(bromo)benzo[d]isothiazole-3-carboxamide,
N-((3R)-1-Azabicyclo[2.2.2]oct-3-yl)-5-(methoxy)benzo[d]isothiazole-3-carboxamide hydroformate,
N-((3R)-1-Azabicyclo[2.2.2]oct-3-yl)-5-(bromo)-1H-indazole-3-carboxamide,
N-((3R)-1-Azabicyclo[2.2.2]oct-3-yl)-5-(cyclopropyl)-1H-indazole-3-carboxamide hydroformate,
N-((3R)-1-Azabicyclo[2.2.2]oct-3-yl)-5-(furan-3-yl)-1H-indazole-3-carboxamide hydroformate,
N-((3R)-1-Azabicyclo[2.2.2]oct-3-yl)-5-(phenyl)-1H-indazole-3-carboxamide hydroformate,
N-((3R)-1-Azabicyclo[2.2.2]oct-3-yl)-5-(thiophen-2-yl)-1H-indazole-3-carboxamide,
N-((3R)-1-Azabicyclo[2.2.2]oct-3-yl)-5-(thiophen-2-yl)-1H-indazole-3-carboxamide hydroformate,
N-((3R)-1-Azabicyclo[2.2.2]oct-3-yl)-5-(thiophen-3-yl)-1H-indazole-3-carboxamide hydroformate,
N-((3S)-1-Azabicyclo[2.2.2]oct-3-yl)-5-(bromo)benzo[d]isothiazole-3-carboxamide,
N-((3S)-1-Azabicyclo[2.2.2]oct-3-yl)-5-methoxybenzo[d]isothiazole-3-carboxamide hydroformate,
N-((3S)-1-Azabicyclo[2.2.2]oct-3-yl)-5-(bromo)-1H-indazole-3-carboxamide,
N-((3S)-1-Azabicyclo[2.2.2]oct-3-yl)-5-(furan-3-yl)-1H-indazole-3-carboxamide hydroformate,
N-((3S)-1-Azabicyclo[2.2.2]oct-3-yl)-5-(phenyl)-1H-indazole-3-carboxamide hydroformate,
N-((3S)-1-Azabicyclo[2.2.2]oct-3-yl)-5-(thiophen-2-yl)-1H-indazole-3-carboxamide hydroformate,
N-((3S)-1-Azabicyclo[2.2.2]oct-3-yl)-5-(thiophen-3-yl)-1H-indazole-3-carboxamide hydroformate,
N-((3R)-1-Azabicyclo[2.2.2]oct-3-yl)-6-bromobenzo[d]isothiazole-3-carboxamide,
N-((3R)-1-Azabicyclo[2.2.2]oct-3-yl)-6-cyclopropylbenzo[d]isothiazole-3-carboxamide,
N-((3R)-1-Azabicyclo[2.2.2]oct-3-yl)-6-(2-fluorophenyl)benzo[d]isothiazole-3-carboxamide,
N-((3R)-1-Azabicyclo[2.2.2]oct-3-yl)-6-(2-fluorophenyl)benzo[d]isothiazole-3-carboxamide hydroformate,
N-((3R)-1-Azabicyclo[2.2.2]oct-3-yl)-6-(3-fluorophenyl)benzo[d]isothiazole-3-carboxamide,
N-((3R)-1-Azabicyclo[2.2.2]oct-3-yl)-6-(3-fluorophenyl)benzo[d]isothiazole-3-carboxamide hydroformate,
N-((3R)-1-Azabicyclo[2.2.2]oct-3-yl)-6-(4-fluorophenyl)benzo[d]isothiazole-3-carboxamide,
N-((3R)-1-Azabicyclo[2.2.2]oct-3-yl)-6-(4-fluorophenyl)benzo[d]isothiazole-3-carboxamide hydroformate,
N-((3R)-1-Azabicyclo[2.2.2]oct-3-yl)-6-(3-furan-3-yl)benzo[d]isothiazole-3-carboxamide,
N-((3R)-1-Azabicyclo[2.2.2]oct-3-yl)-6-(3-furan-3-yl)benzo[d]isothiazole-3-carboxamide hydroformate,
N-((3R)-1-Azabicyclo[2.2.2]oct-3-yl)-6-methoxybenzo[d]isothiazole-3-carboxamide,
N-((3R)-1-Azabicyclo[2.2.2]oct-3-yl)-6-(morpholin-4-yl)benzo[d]isothiazole-3-carboxamide hydroformate,
N-((3R)-1-Azabicyclo[2.2.2]-3-yl)-6-phenylbenzo[d]isothiazole-3-carboxamide,
N-((3R)-1-Azabicyclo[2.2.2]oct-3-yl)-6-phenylbenzo[d]isothiazole-3-carboxamide hydroformate,
N-((3R)-1-Azabicyclo[2.2.2]oct-3-yl)-6-(pyridin-3-yl)benzo[d]isothiazole-3-carboxamide,
N-((3R)-1-Azabicyclo[2.2.2]oct-3-yl)-6-(pyridin-3-yl)benzo[d]isothiazole-3-carboxamide hydroformate,
N-((3R)-1-Azabicyclo[2.2.2]oct-3-yl)-6-(pyridin-4-yl)benzo[d]isothiazole-3-carboxamide,
N-((3R)-1-Azabicyclo[2.2.2]oct-3-yl)-6-(pyridin-4-yl)benzo[d]isothiazole-3-carboxamide hydroformate,
N-((3R)-1-Azabicyclo[2.2.2]oct-3-yl)-6-(thiophen-2-yl)benzo[d]isothiazole-3-carboxamide,
N-((3R)-1-Azabicyclo[2.2.2]oct-3-yl)-6-(thiophen-3-yl)benzo[d]isothiazole-3-carboxamide,
N-((3R)-1-Azabicyclo[2.2.2]oct-3-yl)-6-(bromo)-1H-indazole-3-carboxamide,
N-((3R)-1-Azabicyclo[2.2.2]oct-3-yl)-6-(furan-3-yl)-1H-indazole-3-carboxamide hydroformate,
N-((3R)-1-Azabicyclo[2.2.2]oct-3-yl)-6-(phenyl)-1H-indazole-3-carboxamide hydroformate,
N-((3R)-1-Azabicyclo[2.2.2]oct-3-yl)-6-(thiophen-2-yl)-1H-indazole-3-carboxamide hydroformate,
N-((3R)-1-Azabicyclo[2.2.2]oct-3-yl)-6-(thiophen-3-yl)-1H-indazole-3-carboxamide hydroformate,
N-((3S)-1-Azabicyclo[2.2.2]oct-3-yl)-6-bromobenzo[d]isothiazole-3-carboxamide,
N-((3S)-1-Azabicyclo[2.2.2]oct-3-yl)-6-cyclopropylbenzo[d]isothiazole-3-carboxamide,
N-((3S)-1-Azabicyclo[2.2.2]oct-3-yl)-6-(2-fluorophenyl)benzo[d]isothiazole-3-carboxamide hydroformate,
N-((3S)-1-Azabicyclo[2.2.2]oct-3-yl)-6-(3-fluorophenyl)benzo[d]isothiazole-3-carboxamide hydroformate,
N-((3S)-1-Azabicyclo[2.2.2]oct-3-yl)-6-(4-fluorophenyl)benzo[d]isothiazole-3-carboxamide hydroformate,
N-((3S)-1-Azabicyclo[2.2.2]oct-3-yl)-6-(furan-3-yl)benzo[d]isothiazole-3-carboxamide hydroformate,
N-((3S)-1-Azabicyclo[2.2.2]oct-3-yl)-6-methoxybenzo[d]isothiazole-3-carboxamide,
N-((3S)-1-Azabicyclo[2.2.2]oct-3-yl)-6-(morpholin-4-yl)benzo[d]isothiazole-3-carboxamide hydroformate,
N-((3S)-1-Azabicyclo[2.2.2]oct-3-yl)-6-phenylbenzo[d]isothiazole-3-carboxamide hydroformate,
N-((3S)-1-Azabicyclo[2.2.2]oct-3-yl)-6-(pyridin-3-yl)benzo[d]isothiazole-3-carboxamide hydroformate,
N-((3S)-1-Azabicyclo[2.2.2]oct-3-yl)-6-(pyridin-4-yl)benzo[d]isothiazole-3-carboxamide hydroformate,
N-((3S)-1-Azabicyclo[2.2.2]oct-3-yl)-6-(thiophen-2-yl)benzo[d]isothiazole-3-carboxamide hydroformate,
N-((3S)-1-Azabicyclo[2.2.2]oct-3-yl)-6-(thiophen-3-yl)benzo[d]isothiazole-3-carboxamide,
N-((3S)-1-Azabicyclo[2.2.2]oct-3-yl)-6-(bromo)-1H-indazole-3-carboxamide,
N-((3S)-1-Azabicyclo[2.2.2]oct-3-yl)-6-(furan-3-yl)-1H-indazole-3-carboxamide hydroformate, N-((3S)-1-Azabicyclo[2.2.2]oct-3-yl)-6-(phenyl)-1H-indazole-3-carboxamide hydroformate,
N-((3S)-1-Azabicyclo[2.2.2]oct-3-yl)-6-(thiophen-2-yl)-1H-indazole-3-carboxamide hydroformate,
N-((3S)-1-Azabicyclo[2.2.2]oct-3-yl)-6-(thiophen-3-yl)-1H-indazole-3-carboxamide hydroformate,
N-((3R)-1-Azabicyclo[2.2.2]oct-3-yl)-7-methoxybenzo[d]isothiazole-3-carboxamide,
N-((3S)-1-Azabicyclo[2.2.2]oct-3-yl)-7-methoxybenzo[d]isothiazole-3-carboxamide,
N-((3R)-1-Azabicyclo[2,2,2]oct-3-yl)-N-(1H-indazol-3-ylmethyl)amine,
N-((3S)-1-Aza-bicyclo[2,2,2]oct-3-yl)-N-(1H-indazol-3-ylmethyl)amine,
N-((3R)-1-Aza-bicyclo[2.2.2]oct-3-yl)benzothiazole-4-carboxamide dihydrochloride,
N-((3S)-1-Aza-bicyclo[2.2.2]oct-3-yl)benzothiazole-4-carboxamide dihydrochloride,
N-((3R)-1-Azabicyclo[2.2.2]oct-3-yl)-1H-indazole-4-carboxamide,
N-((3S)-1-Azabicyclo[2.2.2]oct-3-yl)-1H-indazole-4-carboxamide,
N-(1H-Indazol-4-yl)-1-azabicyclo[2,2,2]oct-3-ylcarboxamide,
N-(1-Azabicyclo[2,2,2]oct-3-yl)-N-(1H-indazol-4-ylmethyl)amine,
N-((3R)-1-Azabicyclo[2,2,2]oct-3-yl)benzothiazole-7-carboxamide hydrochloride,
N-((3S)-1-Azabicyclo[2,2,2]oct-3-yl)benzothiazole-7-carboxamide hydrochloride,
N-((3R)-1-Azabicyclo[2.2.2]oct-3-yl)-1H-indazole-7-carboxamide,
N-((3R)-1-Azabicyclo[2.2.2]oct-3-yl)-1H-indazole-7-carboxamide hydrochloride,
N-((3S)-1-Azabicyclo[2.2.2]oct-3-yl)-1H-indazole-7-carboxamide,
N-((3S)-1-Azabicyclo[2.2.2]oct-3-yl)-1H-indazole-7-carboxamide hydrochloride,
Benzothiazole-4-carboxamide, N-1-aza-bicyclo[2,2,2]oct-3-yl,
(R) Benzothiazole-4-carboxamide, N-1-aza-bicyclo[2,2,2]oct-3-yl,
(S) Benzothiazole-4-carboxamide, N-1-aza-bicyclo[2,2,2]oct-3-yl,
1-Aza-bicyclo[2,2,2]oct-3-ylcarboxamide, N-1H-indazol-3-yl,
(S) 1-Aza-bicyclo[2,2,2]oct-3-ylcarboxamide, N-1H-indazol-3-yl,
(R) 1-Aza-bicyclo[2,2,2]oct-3-ylcarboxamide, N-1H-indazol-3-yl,
(S) 1-Aza-bicyclo[2,2,2]oct-3-ylcarboxamide, N-1H-indazol-4-yl,
(R) 1-Aza-bicyclo[2,2,2]oct-3-ylcarboxamide, N-1H-indazol-4-yl,
1-Aza-bicyclo[2,2,2]oct-3-ylcarboxamide, N-1H-indazol-7-yl,
(S) 1-Aza-bicyclo[2,2,2]oct-3-ylcarboxamide, N-1H-indazol-7-yl,
(R) 1-Aza-bicyclo[2,2,2]oct-3-ylcarboxamide, N-1H-indazol-7-yl,
1-Aza-bicyclo[2,2,2]oct-3-ylcarboxamide, benzothiazol-4-yl,
(S) 1-Aza-bicyclo[2,2,2]oct-3-ylcarboxamide, benzothiazol-4-yl,
(R) 1-Aza-bicyclo[2,2,2]oct-3-ylcarboxamide, benzothiazol-4-yl,
1-Aza-bicyclo[2,2,2]oct-3-ylcarboxamide, benzothiazol-7-yl,
(S) 1-Aza-bicyclo[2,2,2]oct-3-ylcarboxamide, benzothiazol-7-yl,
(R) 1-Aza-bicyclo[2,2,2]oct-3-ylcarboxamide, benzothiazol-7-yl,
(S) (1-Aza-bicyclo[2,2,2]oct-3-yl)-(1H-indazol-3-ylmethyl)-amine,
(R) (1-Aza-bicyclo[2,2,2]oct-3-yl)-(1H-indazol-3-ylmethyl)-amine,
(S) (1-Aza-bicyclo[2,2,2]oct-3-yl)-(1H-indazol-4-ylmethyl)-amine,
(R) (1-Aza-bicyclo[2,2,2]oct-3-yl)-(1H-indazol-4-ylmethyl)-amine,
(1-Aza-bicyclo[2,2,2]oct-3-yl)-(1H-indazol-5-ylmethyl)-amine,
(S) (1-Aza-bicyclo[2,2,2]oct-3-yl)-(1H-indazol-5-ylmethyl)-amine,
(R) (1-Aza-bicyclo[2,2,2]oct-3-yl)-(1H-indazol-5-ylmethyl)-amine,
(1-Aza-bicyclo[2,2,2]oct-3-yl)-(1H-indazol-6-ylmethyl)-amine,
(S) (1-Aza-bicyclo[2,2,2]oct-3-yl)-(1H-indazol-6-ylmethyl)-amine,
(R) (1-Aza-bicyclo[2,2,2]oct-3-yl)-(1H-indazol-6-ylmethyl)-amine,
(1-Aza-bicyclo[2,2,2]oct-3-yl)-(1H-indazol-7-ylmethyl)-amine,
(S) (1-Aza-bicyclo[2,2,2]oct-3-yl)-(1H-indazol-7-ylmethyl)-amine,
(R) (1-Aza-bicyclo[2,2,2]oct-3-yl)-(1H-indazol-7-ylmethyl)-amine,
(1-Aza-bicyclo[2,2,2]oct-3-yl)-(benzothiazol-4-ylmethyl)-amine,
(S) (1-Aza-bicyclo[2,2,2]oct-3-yl)-(benzothiazol-4-ylmethyl)-amine,
(R) (1-Aza-bicyclo[2,2,2]oct-3-yl)-(benzothiazol-4-ylmethyl)-amine,
(1-Aza-bicyclo[2,2,2]oct-3-yl)-(benzothiazol-5-ylmethyl)-amine,
(S) (1-Aza-bicyclo[2,2,2]oct-3-yl)-(benzothiazol-5-ylmethyl)-amine,
(R) (1-Aza-bicyclo[2,2,2]oct-3-yl)-(benzothiazol-5-ylmethyl)-amine,
(1-Aza-bicyclo[2,2,2]oct-3-yl)-(benzothiazol-6-ylmethyl)-amine,
(S) (1-Aza-bicyclo[2,2,2]oct-3-yl)-(benzothiazol-6-ylmethyl)-amine,
(R) (1-Aza-bicyclo[2,2,2]oct-3-yl)-(benzothiazol-6-ylmethyl)-amine,
(1-Aza-bicyclo[2,2,2]oct-3-yl)-(benzothiazol-7-ylmethyl)-amine,
(S) (1-Aza-bicyclo[2,2,2]oct-3-yl)-(benzothiazol-7-ylmethyl)-amine,
(R) (1-Aza-bicyclo[2,2,2]oct-3-yl)-(benzothiazol-7-ylmethyl)-amine,
(1-Aza-bicyclo[2,2,2]oct-3-ylmethyl)-(1H-indazol-3-yl)-amine,
(S) (1-Aza-bicyclo[2,2,2]oct-3-ylmethyl)-(1H-indazol-3-yl)-amine,
(R) (1-Aza-bicyclo[2,2,2]oct-3-ylmethyl)-(1H-indazol-3-yl)-amine,
(1-Aza-bicyclo[2,2,2]oct-3-ylmethyl)-(1H-indazol-4-yl)-amine,
(S) (1-Aza-bicyclo[2,2,2]oct-3-ylmethyl)-(1H-indazol-4-yl)-amine, (R) (1-Aza-bicyclo[2,2,2]oct-3-ylmethyl)-(1H-indazol-4-yl)-amine,
(1-Aza-bicyclo[2,2,2]oct-3-ylmethyl)-(1H-indazol-5-yl)-amine,
(S) (1-Aza-bicyclo[2,2,2]oct-3-ylmethyl)-(1H-indazol-5-yl)-amine,
(R) (1-Aza-bicyclo[2,2,2]oct-3-ylmethyl)-(1H-indazol-5-yl)-amine,
(1-Aza-bicyclo[2,2,2]oct-3-ylmethyl)-(1H-indazol-6-yl)-amine,
(S) (1-Aza-bicyclo[2,2,2]oct-3-ylmethyl)-(1H-indazol-6-yl)-amine,
(R) (1-Aza-bicyclo[2,2,2]oct-3-ylmethyl)-(1H-indazol-6-yl)-amine,
(1-Aza-bicyclo[2,2,2]oct-3-ylmethyl)-(1H-indazol-7-yl)-amine,
(S) (1-Aza-bicyclo[2,2,2]oct-3-ylmethyl)-(1H-indazol-7-yl)-amine,
(R) (1-Aza-bicyclo[2,2,2]oct-3-ylmethyl)-(1H-indazol-7-yl)-amine,
(1-Aza-bicyclo[2,2,2]oct-3-ylmethyl)-(benzothiazol-4-yl)-amine,
(S) (1-Aza-bicyclo[2,2,2]oct-3-ylmethyl)-(benzothiazol-4-yl)-amine,
(R) (1-Aza-bicyclo[2,2,2]oct-3-ylmethyl)-(benzothiazol-4-yl)-amine,
(1-Aza-bicyclo[2,2,2]oct-3-ylmethyl)-(benzothiazol-5-yl)-amine,
(S) (1-Aza-bicyclo[2,2,2]oct-3-ylmethyl)-(benzothiazol-5-yl)-amine,
(R) (1-Aza-bicyclo[2,2,2]oct-3-ylmethyl)-(benzothiazol-5-yl)-amine,
(1-Aza-bicyclo[2,2,2]oct-3-ylmethyl)-(benzothiazol-6-yl)-amine,
(S) (1-Aza-bicyclo[2,2,2]oct-3-ylmethyl)-(benzothiazol-6-yl)-amine,
(R) (1-Aza-bicyclo[2,2,2]oct-3-ylmethyl)-(benzothiazol-6-yl)-amine,
(1-Aza-bicyclo[2,2,2]oct-3-ylmethyl)-(benzothiazol-7-yl)-amine,
(S) (1-Aza-bicyclo[2,2,2]oct-3-ylmethyl)-(benzothiazol-7-yl)-amine,
(R) (1-Aza-bicyclo[2,2,2]oct-3-ylmethyl)-(benzothiazol-7-yl)-amine,
and physiological salts thereof.

Preferred aspects include pharmaceutical compositions comprising a compound of this invention and a pharmaceutically acceptable carrier and, optionally, another active agent as discussed below; a method of stimulating or activating inhibiting alpha-7 nicotinic receptors, e.g., as determined by a conventional assay or one described herein, either in vitro or in vivo (in an animal, e.g., in an animal model, or in a mammal or in a human); a method of treating a neurological syndrome, e.g., loss of memory, especially long-term memory, cognitive impairment or decline, memory impairment, etc. method of treating a disease state modulated by nicotinic alpha-7 activity, in a mammal, e.g., a human, e.g., those mentioned herein.

The compounds of the present invention may be prepared conventionally. Some of the known processes that can be used are described below. All starting materials are known or can be conventionally prepared from known starting materials.

Acids that can be used in the preparation of the quinuclidine amide are commercially available, can be prepared by known procedures described in the literature, or as described below. For example, indazolecarboxylic acids can be prepared from bromo-2-methylaniline by diazotization followed by metal-halogen exchange and trapping with $CO_2$, to give the corresponding indazolecarboxylic acid (See, e.g., DeLucca, G. V. Substituted 2H-1,3-Diazapin-2-one Useful as an HIV Protease Inhibitor, U.S. Pat. No. 6,313,110 B1, Nov. 6, 2001; and Sun, J. H.; Teleha, C. A.; Yan, J. S.; Rodgers, J. D.; Nugiel, D. A. *Efficient Synthesis of 5-(Bromomethyl)-and 5-(Aminomethyl)-1-THP-Indazole. J. Org. Chem.* 1997, 62, 5627-5629). 4-Benzothiazolecarboxylic acid can be prepared from 2-amino-4-chloro-benzothiazole by reaction with isoamyl nitrite followed by metal-halogen exchange and trapping with $CO_2$. 5-Benzothiazolecarboxylic acid can be prepared from 4-chloro-3-nitrobenzoic acid by reaction with $Na_2S$ and NaOH followed by reduction with Zn in formic acid. 3-Aminoquinuclidine and the R— and S— enantiomers thereof are commercially available. The quinuclidine amide can be prepared by the coupling reaction of acids with 3-aminoquinuclidine and HBTU or HOBt and EDCI in DMF, or by converting the acids to the corresponding acid chloride and then reacting with 3-aminoquinuclidine (Macor, J. E.; Gurley, D.; Lanthorn, T.; Loch, J.; Mack, R. A.; Mullen, G.; Tran, O.; Wright, N.; and J. E. Macor et al., *The 5-HT3-Antagonist Tropisetron (ICS 205-930) is a Potent and Selective α-7 Nicotinic Receptor Partial Agonist. Bioorg. Med. Chem. Lett.* 2001, 9, 319-321). The couplings are generally performed at room temperatures for 4-8 hours. Thioamide analogs can be prepared from the amides by reaction with Lawesson's reagent (Wipf P.; Kim, Y.; Goldstein, D. M., *J. Am. Chem. Soc.,* 1995, 117, 11106). The resultant adducts can be isolated and purified by standard techniques, such as chromatography or recrystallization, practiced by those skilled in the art.

Quinuclidine amines may be prepared from quinuclidine amides by standard reduction procedures as described, for example, below.

One of ordinary skill in the art will recognize that compounds of Formulas I-IV and I'-IV' can exist in different tautomeric and geometrical isomeric forms. All of these compounds, including cis isomers, trans isomers, diastereomic mixtures, racemates, nonracemic mixtures of enantiomers, substantially pure, and pure enantiomers, are within the scope of the present invention. Substantially pure enantiomers contain no more than 5% w/w of the corresponding opposite enantiomer, preferably no more than 2%, most preferably no more than 1%.

The optical isomers can be obtained by resolution of the racemic mixtures according to conventional processes, for example, by the formation of diastereoisomeric salts using an optically active acid or base or formation of covalent diastereomers. Examples of appropriate acids are tartaric, diacetyltartaric, dibenzoyltartaric, ditoluoyltartaric and camphorsulfonic acid. Mixtures of diastereoisomers can be separated into their individual diastereomers on the basis of their physical and/or chemical differences by methods known to those skilled in the art, for example, by chromatography or fractional crystallization. The optically active bases or acids are then liberated from the separated diastereomeric salts. A different process for separation of optical isomers involves the use of chiral chromatography (e.g., chiral HPLC columns), with or without conventional derivation, optimally chosen to maximize the separation of the enantiomers. Suitable chiral HPLC columns are manufactured by Diacel, e.g., Chiracel OD and Chiracel OJ among many others, all routinely selectable. Enzymatic separations, with or without derivitization, are also useful. The optically active compounds of Formulas I-IV and I'-IV' can likewise be obtained by utilizing optically active starting materials in chiral synthesis processes under reaction conditions which do not cause racemization.

In addition, one of ordinary skill in the art will recognize that the compounds can be used in different enriched isotopic forms, e.g., enriched in the content of $^2H$, $^3H$, $^{11}C$, $^{13}C$ and/or $^{14}C$. In one particular embodiment, the compounds are deuterated. Such deuterated forms can be made the procedure described in U.S. Pat. Nos. 5,846,514 and 6,334,997. As described in U.S. Pat. Nos. 5,846,514 and 6,334,997, deuteration can improve the efficacy and increase the duration of action of drugs.

Deuterium substituted compounds can be synthesized using various methods such as described in: Dean, Dennis C.; Editor. Recent Advances in the Synthesis and Applications of Radiolabeled Compounds for Drug Discovery and Development. [In: Curr., Pharm. Des., 2000; 6(10)] (2000), 110 pp. CAN 133:68895 AN 2000:473538 CAPLUS; Kabalka, George W.; Varma, Rajender S. The synthesis of radiolabeled compounds via organometallic intermediates. Tetrahedron (1989), 45(21), 6601-21, CODEN: TETRAB ISSN:0040-4020. CAN 112:20527 AN 1990:20527 CAPLUS; and Evans, E. Anthony. Synthesis of radiolabeled compounds, J. Radioanal. Chem. (1981), 64(1-2), 9-32. CODEN: JRACBN ISSN:0022-4081, CAN 95:76229 AN 1981:476229 CAPLUS.

Where applicable, the present invention also relates to useful forms of the compounds as disclosed herein, such as pharmaceutically acceptable salts or prodrugs of all the compounds of the present invention for which salts or prodrugs can be prepared. Pharmaceutically acceptable salts include those obtained by reacting the main compound, functioning as a base, with an inorganic or organic acid to form a salt, for example, salts of hydrochloric acid, sulfuric acid, phosphoric acid, methane sulfonic acid, camphor sulfonic acid, oxalic acid, maleic acid, succinic acid, citric acid, formic acid, hydrobromic acid, benzoic acid, tartaric acid, fumaric acid, salicylic acid, mandelic acid, and carbonic acid. Pharmaceutically acceptable salts also include those in which the main compound functions as an acid and is reacted with an appropriate base to form, e,g., sodium, potassium, calcium, magnesium, ammonium, and choline salts. Those skilled in the art will further recognize that acid addition salts of the claimed compounds may be prepared by reaction of the compounds with the appropriate inorganic or organic acid via any of a number of known methods; Alternatively, alkali and alkaline earth metal salts can be prepared by reacting the compounds of the invention with the appropriate base via a variety of known methods.

The following are further examples of acid salts that can be obtained by reaction with inorganic or organic acids: acetates, adipates, alginates, citrates, aspartates, benzoates, benzenesulfonates, bisulfates, butyrates, camphorates, digluconates, cyclopentanepropionates, dodecylsulfates, ethanesulfonates, glucoheptanoates, glycerophosphates, hemisulfates, heptanoates, hexanoates, fumarates, hydrobromides, hydroiodides, 2-hydroxy-ethanesulfonates, lactates, maleates, methanesulfonates, nicotinates, 2-naphthalenesulfonates, oxalates, palmoates, pectinates, persulfates, 3-phenylpropionates, picrates, pivalates, propionates, succinates, tartrates, thiocyanates, tosylates, mesylates and undecanoates.

Preferably, the salts formed are pharmaceutically acceptable for administration to mammals. However, pharmaceutically unacceptable salts of the compounds are suitable as intermediates, for example, for isolating the compound as a salt and then converting the salt back to the free base compound by treatment with an alkaline reagent. The free base can then, if desired, be converted to a pharmaceutically acceptable acid addition salt.

The compounds of the invention can be administered alone or as an active ingredient of a formulation. Thus, the present invention also includes pharmaceutical compositions of compounds of Formulas I-IV and I'-IV', containing, for example, one or more pharmaceutically acceptable carriers.

Numerous standard references are available that describe procedures for preparing various formulations suitable for administering the compounds according to the invention. Examples of potential formulations and preparations are contained, for example, in the Handbook of Pharmaceutical Excipients, American Pharmaceutical Association (current edition); Pharmaceutical Dosage Forms: Tablets (Lieberman, Lachman and Schwartz, editors) current edition, published by Marcel Dekker, Inc., as well as Remington's Pharmaceutical Sciences (Arthur Osol, editor), 1553-1593 (current edition).

In view of their alpha-7 stimulating activity and, preferably their high degree of selectivity, the compounds of the present invention can be administered to anyone needing stimulation of alpha-7 receptors. Administration may be accomplished according to patient needs, for example, orally, nasally, parenterally (subcutaneously, intraveneously, intramuscularly, intrasternally and by infusion) by inhalation, rectally, vaginally, topically and by ocular administration.

Various solid oral dosage forms can be used for administering compounds of the invention including such solid forms as tablets, gelcaps, capsules, caplets, granules, lozenges and bulk powders. The compounds of the present invention can be administered alone or combined with various pharmaceutically acceptable carriers, diluents (such as sucrose, mannitol, lactose, starches) and excipients known in the art, including but not limited to suspending agents, solubilizers, buffering agents, binders, disintegrants, preservatives, colorants, flavorants, lubricants and the like. Time release capsules, tablets and gels are also advantageous in administering the compounds of the present invention.

Various liquid oral dosage forms can also be used for administering compounds of the inventions, including aqueous and non-aqueous solutions, emulsions, suspensions, syrups, and elixirs. Such dosage forms can also contain suitable inert diluents known in the art such as water and suitable excipients known in the art such as preservatives, wetting agents, sweeteners, flavorants, as well as agents for emulsifying and/or suspending the compounds of the invention. The compounds of the present invention may be injected, for example, intravenously, in the form of an isotonic sterile solution. Other preparations are also possible.

Suppositories for rectal administration of the compounds of the present invention can be prepared by mixing the compound with a suitable excipient such as cocoa butter, salicylates and polyethylene glycols. Formulations for vaginal administration can be in the form of a pessary, tampon, cream, gel, paste, foam, or spray formula containing, in addition to the active ingredient, such suitable carriers as are known in the art.

For topical administration the pharmaceutical composition can be in the form of creams, ointments, liniments, lotions, emulsions, suspensions, gels, solutions, pastes, powders, sprays, and drops suitable for administration to the skin, eye, ear or nose. Topical administration may also involve transdermal administration via means such as transdermal patches.

Aerosol formulations suitable for administering via inhalation also can be made. For example, for treatment of disorders of the respiratory tract, the compounds according to the invention can be administered by inhalation in the form of a powder (e.g., micronized) or in the form of atomized solutions or suspensions. The aerosol formulation can be placed into a pressurized acceptable propellant.

The compounds can be administered as the sole active agent or in combination with other pharmaceutical agents such as other agents used in the treatment of cognitive impairment and/or memory loss, e.g., other α-7 agonists, PDE4 inhibitors, calcium channel blockers, muscarinic m1 and m2 modulators, adenosine receptor modulators, amphakines NMDA-R modulators, mGluR modulators, dopamine modulators, serotonin modulators, canabinoid modulators, and cholinesterase inhibitors (e.g., donepezil, rivastigimine, and glanthanamine). In such combinations, each active ingredient can be administered either in accordance with their usual dosage range or a dose below their usual dosage range.

The compounds of the invention can be used in conjunction with "positive modulators" which enhance the efficacy of nicotinic receptor agonists. See, e.g., the positive modulators disclosed in WO 99/56745, WO 01/32619, and WO 01/32622. Such combinational therapy can be used in treating conditions/diseases associated with reduced nicotinic transmission.

Further the compounds may be used in conjunction with compounds that bind to Aβ peptides and thereby inhibit the binding of the peptides to α7nAChr subtypes. See, e.g., WO 99/62505.

The present invention further includes methods of treatment that involve activation of α-7 nicotinic receptors. Thus, the present invention includes methods of selectively activating/stimulating α-7 nicotinic receptors in animals, e.g., mammals, especially humans, wherein such activation/stimulation has a therapeutic effect, such as where such activation may relieve conditions involving neurological syndromes, such as the loss of memory, especially long-term memory. Such methods comprise administering to an animal in need thereof, especially a mammal, most especially a human, an effective amount of a compound of Formulas I-IV or I'-IV', alone or as part of a formulation, as disclosed herein.

Agents that bind to nicotinic acetylcholine receptors have been indicated as useful in the treatment and/or prophylaxis of various diseases and conditions, particularly psychotic diseases, neurodegenerative diseases involving a dysfunction of the cholinergic system, and conditions of memory and/or cognition impairment, including, for example, schizophrenia, anxiety, mania, depression, manic depression [examples of psychotic disorders], Tourettes syndrome, Parkinson's disease, Huntington's disease [examples of neurodegenerative diseases], cognitive disorders (such as Alzheimer's disease, Lewy Body Dementia, Amyotrophic Lateral Sclerosis, memory impairment, memory loss, cognition deficit, attention deficit, Attention Deficit Hyperactivity Disorder), and other uses such as treatment of nicotine addiction, inducing smoking cessation, treating pain (i.e., analgesic use), providing neuroprotection, and treating jetlag. See, e.g., WO 97/30998; WO 99/03850; WO 00/42044; WO 01/36417; Holladay et al., J. Med. Chem., 40:26, 4169-94 (1997); Schmitt et al., Annual Reports Med. Chem., Chapter 5, 41-51 (2000); Stevens et al., Psychopharmatology, (1998) 136: 320-27 (1998); and Shytle et al., Molecular Psychiatry, (2002), 7, pp. 525-535.

Thus, in accordance with the invention, there is provided a method of treating a patient, especially a human, suffering from psychotic diseases, neurodegenerative diseases involving a dysfunction of the cholinergic system, and conditions of memory and/or cognition impairment, including, for example, schizophrenia, anxiety, mania, depression, manic depression [examples of psychotic disorders], Tourette's syndrome, Parkinson's disease, Huntington's disease [examples of neurodegenerative diseases], and/or cognitive disorders (such as Alzheimer's disease, Lewy Body Dementia, Amyotrophic Lateral Sclerosis, memory impairment, memory loss, cognition deficit, attention deficit, Attention Deficit Hyperactivity Disorder) comprising administering to the patient an effective amount of a compound according to Formulas I-IV or I'-IV'.

Neurodegenerative disorders included within the methods of the present invention include, but are not limited to, treatment and/or prophylaxis of Alzheimer's diseases, Pick's disease, diffuse Lewy Body disease, progressive supranuclear palsy (Steel-Richardson syndrome), multisystem degeneration (Shy-Drager syndrome), motor neuron diseases including amyotrophic lateral sclerosis, degenerative ataxias, cortical basal degeneration, ALS-Parkinson's-Dementia complex of Guam, subacute sclerosing panencephalitis, Huntington's disease, Parkinson's disease, synucleinopathies, primary progressive aphasia, striatonigral degeneration, Machado-Joseph disease/spinocerebellar ataxia type 3, olivopontocerebellar degenerations, Gilles De La Tourette's disease, bulbar, pseudobulbar palsy, spinal muscular atrophy, spinobulbar muscular atrophy (Kennedy's disease), primary lateral sclerosis, familial spastic paraplegia, Werdnig-Hoffmann disease, Kugelberg-Welander disease, Tay-Sach's disease, Sandhoff disease, familial spastic disease, Wohlfart-Kugelberg-Welander disease, spastic paraparesis, progressive multifocal leukoencephalopathy, prion diseases (such as Creutzfeldt-Jakob, Gerstmann-Sträussler-Scheinker disease, Kuru and fatal familial insomnia), and neurodegenerative disorders resulting from cerebral ischemia or infarction including embolic occlusion and thrombotic occlusion as well as intracranial hemorrhage of any type (including, but not limited to, epidural, subdural, subarachnoid and intracerebral), and intracranial and intravertebral lesions (including, but not limited to, contusion, penetration, shear, compression and laceration).

In addition, α-7nAChRs agonists, such as the compounds of the present invention can be used to treat age-related dementia and other dementias and conditions with memory loss including age-related memory loss, senility, vascular dementia, diffuse white matter disease (Binswanger's disease), dementia of endocrine or metabolic origin, dementia of head trauma and diffuse brain damage, dementia pugilistica and frontal lobe dementia. See, e.g., WO 99/62505. Thus, in accordance with the invention, there is provided a method of treating a patient, especially a human, suffering from age-related dementia and other dementias and conditions with memory loss comprising administering to the patient an effective amount of a compound according to Formulas I-IV or I'-IV'.

Thus, in accordance with a further embodiment, the present invention includes methods of treating patients suffering from memory impairment due to, for example, mild cognitive impairment due to aging, Alzheimer's disease, schizophrenia, Parkinson's disease, Huntington's disease, Pick's disease, Creutzfeld-Jakob disease, depression, aging, head trauma, stroke, CNS hypoxia, cerebral senility, multiinfarct dementia and other neurological conditions, as well as HIV and cardiovascular diseases, comprising administering an effective amount of a compound according to Formulas I-IV or I'-IV'.

Amyloid precursor protein (APP) and Aβ peptides derived therefrom, e.g., $A\beta_{1-40}$, $A\beta_{1-42}$, and other fragments, are known to be involved in the pathology of Alzheimer's disease. The $A\beta_{1-42}$ peptides are not only implicated in neurotoxicity but also are known to inhibit cholinergic transmitter function. Further, it has been determined that Aβ peptides bind to α-7 nAChRs. Thus, agents which block the binding of the Aβ peptides to α-7 nAChRs are useful for treating neurodegenerative diseases. See, e.g., WO 99/62505. In addition, stimulation α-7 nAChRs can protect neurons against cytotoxicity associated with Aβ peptides. See, e.g., Kihara, T. et al., Ann. Neurol., 1997, 42, 159.

Thus, in accordance with an embodiment of the invention there is provided a method of treating and/or preventing dementia in an Alzheimer's patient which comprises administering to the subject a therapeutically effective amount of a compound according to Formulas I-IV or I'-IV' to inhibit the binding of an amyloid beta peptide (preferably, $A\beta_{1-42}$) with nAChRs, preferable α-7 nAChRs, most preferably, human α-7 nAChRs (as well as a method for treating and/or preventing other clinical manifestations of Alzheimer's disease that include, but are not limited to, cognitive and language deficits, apraxias, depression, delusions and other neuropsychiatric symptoms and signs, and movement and gait abnormalities).

The present invention also provides methods for treating other amyloidosis diseases, for example, hereditary cerebral angiopathy, nonneuropathic hereditary amyloid, Down's syndrome, macroglobulinemia, secondary familial Mediterranean fever, Muckle-Wells syndrome, multiple myeloma, pancreatic- and cardiac-related amyloidosis, chronic hemodialysis anthropathy, and Finnish and Iowa amyloidosis.

In addition, nicotinic receptors have been implicated as playing a role in the body's response to alcohol ingestion. Thus, agonists for α-7nAChR's can be used in the treatment of alcohol withdrawal and in anti-intoxication therapy. Thus, in accordance with an embodiment of the invention there is provided a method of treating a patient for alcohol withdrawal or treating a patient with anti-intoxication therapy comprising administering to the patient an effective amount of a compound according to Formulas I-IV or I'-IV'.

Agonists for the α-7nAChR subtypes can also be used for neuroprotection against damage associated with strokes and ischemia and glutamate-induced excitotoxicity. Thus, in accordance with an embodiment of the invention there is provided a method of treating a patient to provide for neuroprotection against damage associated with strokes and ischemia and glutamate-induced excitotoxicity comprising administering to the patient an effective amount of a compound according to Formulas I-IV or I'-IV'.

As noted above, agonists for the α-7nAChR subtypes can also be used in the treatment of nicotine addiction, inducing smoking cessation, treating pain, and treating jetlag, obesity, diabetes, and inflammation. Thus, in accordance with an embodiment of the invention there is provided a method of treating a patient suffering from nicotine addiction, pain, jetlag, obesity and/or diabetes, or a method of inducing smoking cessation in a patient comprising administering to the patient an effective amount of a compound according to Formulas I-IV or I'-IV'.

In addition, due to their affinity to α-7nAChR's, labeled derivatives of the compounds of Formulas I-IV and I'-IV' (e.g., $C^{11}$ or $F^{18}$ labelled derivatives), can be used in neuroimaging of the receptors within, e.g., the brain. Thus, using such labeled agents in vivo imaging of the receptors can be performed using, e.g., PET imaging.

The condition of memory impairment is manifested by impairment of the ability to learn new information and/or the inability to recall previously learned information. Memory impairment is a primary symptom of dementia and can also be a symptom associated with such diseases as Alzheimer's disease, schizophrenia, Parkinson's disease, Huntington's disease, Pick's disease, Creutzfeld-Jakob disease, HIV, cardiovascular disease, and head trauma as well as age-related cognitive decline.

Thus, in accordance with an embodiment of the invention there is provided a method of treating a patient suffering from, for example, mild cognitive impairment (MCI), vascular dementia (VaD), age-associated cognitive decline (AACD), amnesia associated w/open-heart-surgery, cardiac arrest, and/or general anesthesia, memory deficits from early exposure of anesthetic agents, sleep deprivation induced cognitive impairment, chronic fatigue syndrome, narcolepsy, AIDS-related dementia, epilepsy-related cognitive impairment, Down's syndrome, Alcoholism related dementia, drug/substance induced memory impairments, Dementia Puglistica (Boxer Syndrome), and animal dementia (e.g., dogs, cats, horses, etc.) patient comprising administering to the patient an effective amount of a compound according to Formulas I-IV or I'-IV'.

The dosages of the compounds of the present invention depend upon a variety of factors including the particular syndrome to be treated, the severity of the symptoms, the route of administration, the frequency of the dosage interval, the particular compound utilized, the efficacy, toxicology profile, pharmacokinetic profile of the compound, and the presence of any deleterious side-effects, among other considerations.

The compounds of the invention can be administered to mammals, particularly humans, at typical dosage levels customary for α-7 nicotinic receptor agonists such as the known α-7 nicotinic receptor agonist compounds mentioned above. For example, the compounds can be administered, in single or multiple doses, by oral administration at a dosage level of, for example, 0.0001-10 mg/kg/day, e.g., 0.01-10 mg/kg/day. Unit dosage forms can contain, for example, 1-200 mg of active compound. For intravenous administration, the compounds can be administered, in single or multiple dosages.

In carrying out the procedures of the present invention it is of course to be understood that reference to particular buffers, media, reagents, cells, culture conditions and the like are not intended to be limiting, but are to be read so as to include all related materials that one of ordinary skill in the art would recognize as being of interest or value in the particular context in which that discussion is presented. For example, it is often possible to substitute one buffer system or culture medium for another and still achieve similar, if not identical, results. Those of skill in the art will have sufficient knowledge of such systems and methodologies so as to be able, without undue experimentation, to make such substitutions as will optimally serve their purposes in using the methods and procedures disclosed herein.

The present invention will now be further described by way of the following non-limiting examples. In applying the disclosure of these examples, it should be kept clearly in mind that other and different embodiments of the methods disclosed according to the present invention will no doubt suggest themselves to those of skill in the relevant art.

In the foregoing and in the following examples, all temperatures are set forth uncorrected in degrees Celsius; and, unless otherwise indicated, all parts and percentages are by weight.

The entire disclosures of all applications, patents and publications, cited above and below, including U.S. provisional patent application Ser. No. 60/413,151, filed Sep. 25, 2002, and U.S. Provisional application Ser. No. 60/448,469, filed Feb. 21, 2003, are hereby incorporated by reference.

EXAMPLES

All spectra were recorded at 300 MHz on a Bruker Instruments NMR unless otherwise stated. Coupling constants (J)

are in Hertz (Hz) and peaks are listed relative to TMS (δ 0.00 ppm). Microwave reactions were performed using a Personal Chemistry Optimizer™ microwave reactor in 2.5 mL or 5 mL Personal Chemistry microwave reactor vials. All reactions were performed at 200° C. for 600 s with the fixed hold time ON unless otherwise stated. Sulfonic acid ion exchange resins (SCX) were purchased from Varian Technologies. Analytical HPLC was performed on 4.6 mm×100 mm Xterra RP18 3.5μ columns using a gradient of 20/80 to 80/20 water (0.1% formic acid)/acetonitrile (0.1% formic acid) over 6 min.

Representative Procedures

Procedure A

Procedure A provides a method for the coupling between 3-aminoquinuclidine and carboxylic acids to form carboxamide derivatives.

To a solution of the carboxylic acid (16.1 mmol) in N,N-dimethylformamide (65 mL) was added HBTU (16.1 mmol), catalytic amount of dimethylaminopyridine, N,N-diisopropylethylamine (96.6 mmol) and 4 Å activated molecular sieves (2.6 g). The reaction mixture was maintained at room temperature for 2 h under nitrogen and then 3-aminoquinuclidine dihydrochloride (16.1 mmol) was added. After 18 h, the solvent was removed under reduced pressure. The oily residue was partitioned between saturated, aqueous sodium bicarbonate (25 mL) and dichloromethane (100 mL). The aqueous layer was further extracted with 9/1 dichloromethane/methanol (5×100 mL) and the combined organic layers were concentrated. The residue was purified by chromatography using either a mixture of 90/10/1 dichloromethane/methanol/ammonium hydroxide or 70/30/1 ethyl acetate/methanol/ammonium hydroxide as the eluent to provide the product in 30%-70% yield. Alternatively, the products were purified by preparative HPLC using an 8 min gradient of 95/5 to 20/80 water (0.1% formic acid)/acetonitrile (0.1% formic acid).

Procedure B

Procedure B provides a method for the coupling between 3-aminoquinuclidine and benzisothiazole carboxylic acids to form carboxamide derivatives.

To a solution of 6-methoxybenzisothiazole-3-carboxylic acid (61 mg, 0.30 mmol) in a 5/1 mixture of terahydrofuran/N,N-dimethylformamide (12 mL) was added diisopropylethylamine (0.2 mL, 1.1 mmol) and (115 mg, 0.6 mmol) 3-(R)-aminoquinuclidine dihydrochloride. The mixture was cooled to 0° C., and HATU (115 mg, 0.3 mmol) was added in one portion. The reaction mixture was allowed to warm to rt and was maintained overnight. The mixture was partitioned between saturated aqueous potassium carbonate solution and a 95/5 mixture of dichloromethane/methanol. The aqueous layer was extracted with 95/5 dichloromethane/methanol (2×), and the combined organic layers were washed with brine and dried over sodium sulfate. The crude product was purified by chromatography (90/10/1 dichloromethane/methanol/ammonium hydroxide) to provide 72 mg (75%) of the amide as a colorless solid.

Procedure C

Procedure C provides a method for the coupling between 3-aminoquinuclidine and carboxylic acids to form carboxamide derivatives.

The coupling reaction and purification was performed according to procedure A (indazoles, benzthiazoles) or according to procedure B (benzisothiazoles). The free base was dissolved in methanol (3.5 mL/mmol starting acid) and treated with 1N hydrochloric acid in ether (3.5 mL/mmol starting acid). The resulting suspension was diluted with ether (7 mL/mmol starting acid) and was maintained at room temperature for 2 h. The solids were collected by filtration, rinsed with ether, and dried under vacuum to yield (40-60%) of the salt.

Procedure D

Procedure D provides a method for the coupling between 3-aminoquinuclidine and carboxylic acids to form carboxamide derivatives.

To a solution of the carboxylic acid (4.77 mmol) in N,N-dimethylformamide (14 mL) was added N,N-diisopropylethylamine (19 mmol) and 3-aminoquinuclidine dihydrochloride (4.29 mmol). The reaction mixture was maintained at room temperature for 30 min under nitrogen and then HATU (4.76 mol) was added. After 18 h, the reaction mixture was filtered through Celite (methanol rinse) and was divided equally amongst 3 SCX columns. The columns were washed with methanol (100 mL each) and the basic components were eluted with 2 M ammonia in methanol (100 mL each) and concentrated. The residue was purified by chromatography [1/1 to 0/1 ethyl acetate/(70/30/1 ethyl acetate/methanol/ammonium hydroxide)] thus providing the product in 15%-50% yield.

Procedure E

Procedure E provides a method for the formation of carboxamide derivatives from methyl 3-quinuclidinecarboxylic acid ester.

To a solution of the amine in toluene was added 1.0 M solution of trimethylaluminum in toluene (1.1 eq) at 0° C. After 30 min, an additional 1.1 eq of trimethylaluminum was added followed by a solution of methyl 3-quinuclidinecarboxylic acid ester hydrochloride salt (1.1 eq) in dioxane (5 mL). The reaction mixture was heated at 70° C. for 10 h, allowed to cool to rt, and was poured onto a cold, (0° C.) aqueous solution of sodium bicarbonate. The aqueous layer was extracted with 5% methanol in methylene chloride (2×30 mL) and the combined organic layers were washed with brine and concentrated. The residue was purified by preparative HPLC using an 8 min gradient of 95/5 to 20/80 water (0.1% formic acid)/acetonitrile (0.1% formic acid).

Procedure F

Procedure F provides a method for the reduction of the carboxamide to form secondary amie derivatives.

To a solution of the amide (50 mg) in tetrahydrofuran (4 mL) was added lithium aluminum hydride (4.0 eq). The reaction mixture was heated at reflux for 4 h, was cooled to 0° C., and was cautiously quenched with ethanol. The resultant slurry was poured onto ice water and extracted with 5% methanol in dichloromethane (3×) and the combined organic layers were concentrated. The residue was purified by preparative HPLC using an 8 min gradient of 95/5 to 20/80 water (0.1% formic acid)/acetonitrile (0.1% formic acid).

Procedure G

Procedure G provides a method for the coupling between 3-aminoquinuclidine and carboxaldehydes to form secondary amine derivatives.

The suspension of 1H-indazole-4-carboxaldehyde (100 mg), 3-aminoquinuclidine dihydrochloride salt (1.0 eq), and 4 Å molecular sieves in dioxane (4 mL) was heated at reflux for 4 h. The reaction mixture was allowed to cool to rt and was treated with sodium triacetoxyborohydride (3 eq). The reaction mixture was maintained at rt for 2 h and was poured into water, extracted with 5% methanol in dichloromethane (2×30 mL), and the combined extracts were concentrated. The residue was purified by preparative HPLC using an 8 min gradient of 95/5 to 20/80 water (0.1% formic acid)/acetonitrile (0.1% formic acid).

Procedure H

Procedure H provides a method for the coupling between brominated and iodinated aminoquinuclidinecarboxamides and boronic acids to form aryl-substituted derivatives.

In a 5 mL microwave reaction vessel was added the bromide (0.286 mmol), the boronic acid (0.588 mmol), tris(dibenzylideneacetone)dipalladium (0) (0.0289 mmol), tri-tert-butylphosphine tetrafluoroborate (0.0579 mmol), and potassium carbonate (0.810 mmol). The vessel was evacuated, back-filled with argon gas, and the contents diluted with N,N-dimethylformamide (5.0 mL). The vessel was sealed and subjected to microwave irradiation at 200° C. for 600 s. The contents of the reaction were filtered through Celite (methanol wash) and loaded on a 5 g SCX column. The column was washed with methanol (50 mL) and the product was eluted with 2 M ammonia in methanol and concentrated. The residue was purified by preparative HPLC using an 8 min gradient of 95/5 to 20/80 water (0.1% formic acid)/acetonitrile (0.1% formic acid) to give 15-40% of the product Procedure I Procedure I provides a method for the coupling between brominated 3-aminoquinuclidinecarboxamides and amines to form amino-substituted derivatives.

In a 5 mL microwave reaction vessel was added N-((3R)-1-azabicyclo[2.2.2]oct-3-yl)-5-(bromo)benzo[d]isothiazole-3-carboxamide (133 mg, 0.37 mmol), tris(dibenzylideneacetone)dipalladium (0) (34 mg, 0.04 mmol), caesium bicarbonate (213 mg, 1.1 mmol), and (2'-dicyclohexylphosphanylbiphenyl-2-yl)dimethylamine (30 mg, 0.07 mmol). The vial was then evacuated and back-filled with argon gas. The mixture of solids was then diluted with morpholine (0.7 mL), dioxane (1 mL), and triethylamine (0.5 mL) and the reaction vessel was sealed. The reaction mixture was subjected to microwave irradiation at 120° C. for 1800 s. The reaction mixture was filtered through a plug of celite and concentrated in vacuo. The crude product was purified by chromatography (90/10/1 dichloromethane/methanol/ammonium hydroxide) to provide 47 mg (34%) of 6-morpholin-4-ylbenzo[d]isothiazole-3-carboxylic acid ((3R)-1-azabicyclo[2.2.2]oct-3-yl)amide as a colorless solid.

Procedure J

Procedure J provides a method for the coupling between brominated 3-aminoquinuclidinecarboxamides and Grignard reagents to form alkyl-substituted derivatives.

A 5 mL microwave reaction vessel was charged with bis(triphenylphosphine)palladium (II) chloride (0.030 mmol, 0.1 eq) and the bromide (0.30 mmol). The vessel was evacuated and back-filled with argon gas. In a separate reaction vessel, solution of the Grignard (1.2 mmol, 4 eq) was added to a 0.5 M solution of zinc chloride (1.2 mmol, 4 eq) in tetahydrofuran at rt. The suspension was maintained for 30 min and the entire contents were transferred to the reaction vessel via cannula. The vessel was sealed and subjected to microwave irradiation at 100° C. for 600 sec with a pre-stir time of 60 s. The reaction was quenched with acetic acid (0.5 mL), diluted with methanol, and was transferred to a SCX column. The column was washed with methanol (50 mL) and the product was eluted with 2 M ammonia in methanol (50 mL) and concentrated. The residue was purified by chromatography [1/1 to 0/1 ethyl acetate/(70/30/1 ethyl acetate/methanol/ammonium hydroxide)] followed by preparative HPLC using a 5/95 to 80/20 gradient of acetonitrile (0.1% formic acid)/water (0.1% formic acid) over 6 min to provide the product (20-50%). Alternatively, the residue was purified by chromatography (90/10/1 dichloromethane/methanol/ammonium hydroxide).

Procedure K

Procedure K provides a method for the preparation of bromoindazoles from bromomethylanilines. (See, George V. DeLucca, U.S. Pat. No. 6,313,110.)

Acetic anhydride (2.27 eqiv) was added to a cooled (0° C.) solution of bromomethylaniline (1.00 eqiv) in chloroform (1.5 mL/mol) while maintaining the temperature below 40° C. The reaction mixture was allowed to warm to room temperature and was maintained for 1 h. Potassium acetate (0.29 eq) and isoamyl nitrite (2.15 eqiv) was added and the reaction mixture was heated at reflux for 18 h. The volatiles were removed under reduced pressure. Water (0.65 L/mol) was added to the residue and the mixture was concentrated. Concentrated hydrochloric acid (1 L/mol) was added to the residue and the mixture was heated at 50° C. for 2 h. The mixture was allowed to cool to room temperature and the pH was adjusted to 10 by the slow addition of a 50% aqueous sodium hydroxide solution. The mixture was diluted with water (0.65 L/mol) and was extracted with ethyl acetate (2×1.2 L/mol). The combined extracts were washed with brine (1 L/mol) and dried over anhydrous sodium sulfate. The organic solution was filtered through a plug of silica gel (ethyl acetate wash), concentrated, and the residue was triturated with heptane (1 L/mol). The solids were collected by filtration, rinsed with heptane, and dried in a vacuum oven.

Procedure L

Procedure L provides a method for the preparation of indazole carboxylic acid from bromoindazole.

To a solution of bromoindazole (1.00 eqiv) in anhydrous tetrahydrofuran (7 L/mol) at room temperature was added sodium hydride (60% in mineral oil, 1.11 eqiv) in several portions. The resulting solution was maintained for 30 min at room temperature and was then cooled to −60° C. A 1.3 M solution of sec-butyllithium in cyclohexane (2.1 eqiv) was added to the reaction mixture while maintaining the internal temperature below −50° C. The mixture was maintained for an additional 2 h at −50° C. A steady stream of anhydrous carbon dioxide was bubbled through the reaction mixture for 1 h. The flow was continued while the reaction mixture was allowed to warm to room temperature. Brine (6 L/mol) was added and the pH of the mixture was adjusted to 5 with concentrated hydrochloric acid. The mixture was extracted with warm ethyl acetate (3×8 L/mol) and the combined extracts were washed with small volume of brine, dried over anhydrous sodium sulfate, and concentrated. The product was purified by chromatography on silica gel or by crystallization.

Procedure M

Procedure M provides a preparation of 1H-indazole-7-carboxylic acid from 2-amino-3-methylbenzoic acid.

To a solution of 2-amino-3-methylbenzoic acid (10.1 g, 66.9 mmol) in N,N-dimethylformamide (200 mL) was added cesium carbonate (33.2 g, 102 mmol, 1.5 eq). The mixture was stirred for 30 min. A solution of methyl iodide (4.17 mL, 67.0 mmol, 1.0 eq) in N,N-dimethylformamide (50 mL) was added dropwise and the reaction mixture was maintained for 18 h at rt. The reaction mixture was partitioned between water (1 L) and ether (200 mL) and the water layer was extracted with an additional volume of ether (100 mL). The combined extracts were washed with brine (500 mL), dried over anhydrous potassium carbonate, and concentrated to provide 10.2 g (92%) of methyl 2-amino-3-methylbenzoate. $^1$H NMR (400 MHz, CDCl$_3$) δ 7.77 (d, 1H), 7.19 (d, 1H), 6.59 (t, 1H), 5.82 (bs, 2H), 3.86 (s, 3H), 2.17 (s, 3H).

To a solution of the ester (17.5 g, 106 mmol) in chloroform (300 mL) was added acetic anhydride (22.6 mL, 239 mmol, 2.3 eq) while maintaining the temperature below 40° C. The reaction mixture was maintained at room temperature for 1 h when potassium acetate (3.00 g, 30.6 mmol, 0.3 eq) and isoamyl nitrite (30.6 mL, 228 mmol, 2.2 eqiv) was added. The reaction mixture was heated at reflux for 24 h and was allowed to cool to room temperature. The reaction mixture was washed with a saturated, aqueous solution of sodium bicarbonate, dried over sodium sulfate, and concentrated. Methanol (100 mL) and 6 N hydrochloric acid (100 mL) were added to the residue and the mixture was maintained for 18 h at rt. The volatiles were removed under reduced pressure and the residue was triturated with ethyl acetate (100 mL). The product was isolated by filtration, washed with ethyl acetate (20 mL), and dried to provide 15.3 g (68%) of methyl 1H-indazole-7-carboxylate hydrochloride. $^1$H NMR (500 MHz, DMSO-d$_6$) δ 13.3 (bs, 1H), 8.26 (d, 1H), 8.12 (d, 1H), 8.25 (dd, 1H), 7.27 (t, 1H), 3.97 (s, 3H); MS (APCI) m/z 177 (M$^+$+1).

A solution of the indazole (8.30 g, 33.0 mmol) in methanol (100 mL) at 0° C. was treated with an 29% aqueous solution of potassium hydroxide (20 mL). The reaction mixture was allowed to warm to rt and was maintained for 18 h. The pH of the solution was adjusted to 5.5 by the addition of concentrated hydrochloric acid and the volatiles were removed under reduced pressure. The residue was partitioned between brine (100 mL) and ethyl acetate (200 mL) and the aqueous layer was extracted with additional warm ethyl acetate (200 mL). The combined organic extracts were dried over anhydrous sodium sulfate and concentrated. The residue was triturated with ethyl acetate (30 mL) and the solids were isolated by filtration, thus providing 5.86 g (94%) of the acid.

Procedure N

Procedure N provides a preparation of substituted benzisothiazole-3-carboxylic acids from the corresponding thiophenols.

To a solution of 3-methoxythiophenol (3.75 g, 26.7 mmol) in ether (20 mL) was added oxalyl chloride (3.7 mL, 43 mmol) dropwise. The mixture was heated at reflux for 1.5 h, cooled to rt, and concentrated in vacuo. The resulting yellow oil was dissolved in dichloromethane (50 mL), cooled to 0° C., and was treated with aluminum chloride (4.30 g, 32.0 mmol) in portions. The mixture was heated at reflux for 30 min, cooled to rt, and poured onto ice water with stirring. The organic layer was separated and successively washed with saturated, aqueous sodium bicarbonate, water, and brine. The organic layer was dried over magnesium sulfate, filtered and concentrated in vacuo. The residue was purified by chromatography (4/1 ethyl acetate/hexane) which provided 2.46 g (47%) of 6-methoxy-1-benzothiophene-2,3-dione as an orange solid.

To a mixture of the dione (86 mg, 0.44 mmol) in 30% aqueous solution of ammonium hydroxide (2.0 mL) was added 35% aqueous solution hydrogen peroxide (0.2 mL) and the reaction mixture was maintained for 12 h. The precipitated pink solids were isolated by filtration, washed with water, and dried under high vacuum to afford 39 mg (42%) of 6-methoxybenzisothiazole-3-carboxamide.

To a solution of the amide (1.14 g, 5.46 mmol) in methanol (100 mL) was added 10 N sodium hydroxide (12 mL). The mixture was heated at reflux for 12 h, cooled to rt, and was acidified to pH<2 by the slow addition of conc. hydrochloric acid. The organic layer was extracted with dichloromethane (2×) and was dried over sodium sulfate. The crude product was purified by chromatography (300/50/1 dichloromethane/methanol/formic acid) to provide 1.02 g (89%) of 6-methoxy-benzisothiazole-3-carboxylic acid as a pink solid. LC/MS (EI) t$_R$ 6.17 min, m/z 210 (M$^+$+1).

The following acids were prepared by this method:

Benzisothiazole-3-carboxylic acid. $^1$H NMR (CDCl$_3$) δ 8.86 (dd, J=7.1, 2.5, 1H), 8.03 (dd, J=6.3, 1.4, 1H), 7.66-7.61 (m, 2H); LC/MS (EI) t$_R$ 6.75 min, m/z 180 (M$^+$+1).

6-Bromobenzisothiazole-3-carboxylic acid. LC/MS (EI) t$_R$ 9.95 min, m/z 258/260 (M$^+$/M$^+$+2).

5-Methoxybenzisothiazole-3-carboxylic acid. LC/MS (EI) t$_R$ 6.09 min, m/z 210 (M$^+$+1).

5-Bromobenzisothiazole-3-carboxylic acid. LC/MS (EI) t$_R$ 9.88 min, m/z 258/260 (M$^+$/M$^+$+2).

7-Methoxybenzisothiazole-3-carboxylic acid. LC/MS (EI) t$_R$ 6.49 min, m/z 210 (M$^+$+1).

Procedure O

Procedure O provides a method of preparation of 1,3-benzothiazole-5-carboxylic acid from 4-chloro-3-nitrobenzoic acid.

To a solution of 4-chloro-3-nitrobenzoic acid (20.0 g, 99.2 mmol) in N,N-dimethylformamide (400 mL) was added potassium carbonate (35.0 g, 254 mmol, 2.6 eqiv). After 30 min, ethyl iodide (18.6 g, 119 mmol, 1.2 eqiv) was added and the reaction mixture was heated at 50° C. for 4 h. Water (3 L) was added and the mixture was extracted with diethyl ether (2×500 mL). The organic extracts were combined, washed with brine (1 L), dried over anhydrous sodium sulfate and concentrated on vacuum rotary evaporator. The residue was crystallized from hexanes to provide 19.7 g (86%) of the ester. $^1$H NMR (500 MHz, CDCl$_3$) δ 8.51 (d, 1H), 8.17 (dd, 1H), 7.65 (d, 1H), 4.43 (q, 2H), 1.42 (t, 3H).

Sulfur (1.6 g, 49.91 mmol, 0.58 eqiv) was dissolved in a solution of sodium sulfide nonahydrate (12.0 g, 49.96 mmol, 0.58 eqiv) in water (60 mL). This solution was combined with a solution of ethyl 4-chloro-3-nitrobenzoate (19.6 g, 85.36 mmol, 1.00 eqiv) in ethanol (100 mL) and the resulting mixture was heated at reflux for 3 h. The hot reaction mixture was poured into water (600 mL) and maintained for 15 min. The product was isolated by filtration and recrystallized from ethanol to provide 16.5 g (77%) of the disulfide. $^1$H NMR (500 MHz, CDCl$_3$) δ 8.96 (d, 1H), 8.19 (dd, 1H), 7.88 (d, 1H), 4.43 (q, 2H), 1.41 (t, 3H).

A mixture of diethyl 4,4'-dithiobis(3-nitrobenzoate) (11.2 g, 24.8 mmol) and zinc granules (15.0 g, 234 mmol, 9.5 eq) in formic acid (600 mL) was heated to reflux for 48 h. The mixture was allowed to cool to room temperature and concentrated to dryness. The residue was partitioned between ethyl acetate (500 mL) and saturated aqueous sodium bicarbonate (500 mL). The organic layer was separated, dried over anhydrous sodium sulfate and concentrated. The residue was chromatographed on neutral Alumina (1/1 to 0/1 hexanes/dichloromethane) to provide 5.30 g (51%) of the benzthiazole. $^1$H NMR (500 MHz, CDCl$_3$) δ 9.08 (s, 1H), 8.83 (d, 1H), 8.14 (dd, 1H), 8.02 (d, 1H), 4.45 (q, 2H), 1.44 (t, 3H); MS (EI) m/z 208 (M$^+$+1).

To a solution of ethyl 1,3-benzothiazole-5-carboxylate (5.30 g, 25.6 mmol) in a mixture of methanol (150 mL), tetrahydrofuran (40 mL) and water (5 mL) was added a 50% aqueous solution of sodium hydroxide (10 mL). The mixture was maintained at rt for 18 h and was concentrated. The residue was partitioned between water (300 mL) and diethyl ether (200 mL) and the organic layer was removed, Concentrated hydrochloric acid was added to the aqueous layer to adjust the pH to 4 and the mixture was extracted with ethyl acetate (3×300 mL). The combined extracts were washed with brine (200 mL), dried over anhydrous sodium sulfate, and concentrated to yield 4.30 g (94%) the acid.

Procedure P

Procedure P provides a method for the preparation of 1,3-benzothiazole-7-carboxylic acid from ethyl 3-aminobenzoate. (See, Kunz et. al. U.S. Pat. No. 5,770,758)

A solution of ethyl 3-aminobenzoate (14.9 g, 90 mmol) in chlorobenzene (100 mL) was cooled to −10° C. and treated with sulfuric acid (97%, 2.5 mL, 45 mmol, 0.50 eq), dropwise. After 15 min, solid potassium thiocyanate (9.2 g, 95 mmol, 1.05 eq) was added in several portions over 30 min followed by 18-crown-6 (250 mg). The mixture was heated at 100° C. for 10 h, allowed to cool to rt, and was maintained for an additional 4 h. The precipitated solids were isolated by filtration and were washed successively with chlorobenzene (25 mL) and hexanes (3×100 mL). The solid was suspended in water (300 mL) and the suspension was maintained 30 min. The product was isolated by filtration and washed with water (2×100 mL). The product was dried in a vacuum oven (55° C.) overnight to yield 13.4 g (69%) of the thiocarbamate. $^1$H NMR (500 MHz, DMSO-$d_6$) δ 1.32 (t, J=7.5, 3H), 4.32 (q, J=7, 2H), 7.44,-7.47 (m, 2H), 7.68-7.76 (m, 3H), 8.05 (s, 1H), 9.86 (s, 1H); MS (APCI) m/z 225 (M$^+$+1).

A solution of thiocarbamate (1.95 g, 12.2 mmol, 2.11 eqiv) in chloroform (10 mL) was added dropwise over a period of 40 min to a vigorously maintained mixture of ethyl 3-[(aminocarbonothioyl)amino]benzoate (1.30 g, 5.78 mmol, 1.00 eqiv), glacial acetic acid (10 mL) and chloroform (10 mL). The mixture was maintained 30 min at rt and then was heated at 70° C. for 4 h. The mixture was allowed to cool to room temperature and maintained for an additional 13 h. The volatiles were removed under reduced pressure and the solid residue was suspended in a mixture of chloroform (10 mL) and acetone (10 mL). The product was isolated by filtration, washed successively with acetone (5 mL) and hexanes (10 mL), and dried in a vacuum oven to provide 1.65 g (95%) of product as a mixture of ethyl 2-amino-1,3-benzothiazole-7-carboxylate hydrobromide and ethyl 2-amino-1,3-benzothiazole-5-carboxylate hydrobromide in a ratio of 95/5, respectively. This product was partitioned between saturated aqueous solution of sodium bicarbonate (25 mL) and a mixture of ethyl acetate (70 mL) and tetrahydrofuran (30 mL). The organic layer was separated, dried over anhydrous sodium sulfate and concentrated. The residue was crystallized form ethyl acetate to provide pure ethyl 2-amino-1,3-benzothiazole-7-carboxylate. $^1$H NMR (500 MHz, DMSO-$d_6$) δ 1.35 (t, J=7.5, 3H), 4.36 (q, J=7, 2H), 7.35 (t, J=7.5, 1H), 7.57 (d, 1=7, 1H), 7.61 (bs, 2H), 7.65 (d, J=8, 1H); MS (EI) m/z 223 (M$^+$+1).

iso-Amylnitrite (7.4 mL, 53 mmol, 2.2 eqiv) was added to a solution of ethyl 2-amino-1,3-benzothiazole-7-carboxylate (5.40 g, 24.3 mmol) in tetrahydrofuran (70 mL) and the mixture was heated at reflux for 4 h. The volatiles were removed under reduced pressure and the residue was purified by chromatography (0/100 to 5/95 methanol/dichloromethane) to provide 3.56 g (71%) of the ester. $^1$H NMR (500 MHz, CDCl$_3$) δ 1.47 (t, J=7.5, 3H), 4.49 (q, J=7, 2H), 7.62 (t, J=8, 1H), 8.20 (d, J=6.5, 1H), 8.33 (d, J=8, 1H), 9.12 (s, 1H); MS (EI) m/z 208 (M$^+$+1). Aqueous sodium hydroxide (50%, 10 mL) was added to a 0° C. solution of ethyl 1,3-benzothiazole-7-carboxylate (3.5 g, 16.89 mmol) in a mixture of methanol (65 mL), tetrahydrofuran (20 mL) and water (5 mL). The mixture was maintained at room temperature for 4 h and the volatiles were removed under reduced pressure. The residue was dissolved in water (100 mL) and concentrated hydrochloric acid was added to adjust pH of the solution to 5. The mixture was cooled to 0° C. and maintained for 30 min. The product was isolated by filtration, washed with water (10 mL), and dried in vacuum oven (70° C.) overnight to yield 2.75 g (91%) of the acid. $^1$H NMR (500 MHz, DMSO-$d_6$) δ 7.71 (t, J=7.5, 1H), 8.15 (d, J=7, 1H), 8.38 (d, J=8, 1H), 9.51 (s, 1H), 13.74 (bs, 1H); MS (APCI) m/z 178 (M$^+$−1).

Procedure Q

Procedure Q provides a method for the conversion of brominated isatins to the corresponding indazole-3-carboxylic acids.

The conversion of the substituted isatins to the corresponding indazole-3-carboxylic acids is essentially the same method as described for indazole-3-carboxylic acid: Snyder, H. R., et. al. *J. Am. Chem. Soc.* 1952, 74, 2009. The substituted isatin (22.1 mmol) was diluted with 1 N sodium hydroxide (24 mL) and was heated at 50° C. for 30 min. The burgundy solution was allowed to cool to rt and was maintained for 1 h. The reaction mixture was cooled to 0° C. and was treated with a 0° C. solution of sodium nitrite (22.0 mmol) in water (5.5 mL). This solution was added through a pipet submerged below the surface of a vigorously stirred solution of sulfuric acid (2.3 mL) in water (45 mL) at 0° C. The addition took 15 min and the reaction was maintained for an additional 30 min. A cold (0° C.) solution of tin (II) chloride dihydrate (52.7 mmol) in concentrated hydrochloric acid (20 mL) was added to the reaction mixture over 10 min and the reaction mixture was maintained for 60 min. The precipitated solids were isolated by filtration, washed with water, and dried to give a quantitative mass balance. This material was of sufficient purity ($^1$H NMR and LC/MS) to use in the next step without further purification.

Using the above Procedures and further procedures described below, the following compounds in Examples 1-94 were prepared:

Example 1

N-((3R)-1-Azabicyclo[2.2.2]oct-3-yl)benzo[d]isothiazole-3-carboxamide

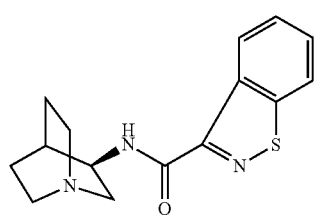

Prepared from benzo[d]isothiazole-3-carboxylic acid using Procedure B. Yield 42%. $^1$H NMR (CD$_3$OD) δ 8.73 (d, J=8.0, 1H), 8.05 (d, J=8.1, 1H), 7.59-7.47 (m, 2H), 4.19-4.16 (m, 1H), 3.37-3.28 (m, 1H), 3.05-2.96 (m, 1H), 2.86-2.79 (m, 2H), 2.07-2.04 (m, 1H), 2.02-1.80 (m, 1H), 1.78-1.74 (in, 1H), 1.56-1.52 (m, 1H); LC/MS (EI) $t_R$ 3.61 min, m/z 288 (M$^+$+1).

Example 2

N-((3R)-1-Azabicyclo[2.2.2]oct-3-yl)benzo[d]isothiazole-3-carboxamide hydrochloride

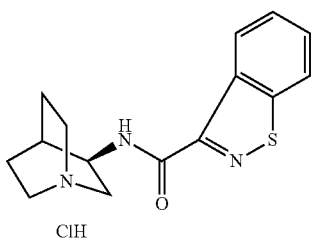

Prepared from benzo[d]isothiazole-3-carboxylic acid using Procedure C. Yield 95%. LC/MS (EI) $t_R$ 3.55 min, m/z 288 (M$^+$+1).

Example 3

N-((3S)-1-Azabicyclo[2.2.2]oct-3-yl)benzo[d]isothiazole-3-carboxamide

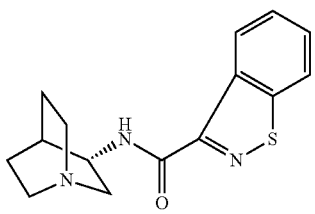

Prepared from benzo[d]isothiazole-3-carboxylic acid using Procedure B. Yield 44%. LC/MS (EI) $t_R$ 3.71 min, m/z 288 (M$^+$+1).

Example 4

N-((3S)-1-Azabicyclo[2.2.2]oct-3-yl)benzo[d]isothiazole-3-carboxamide hydrochloride

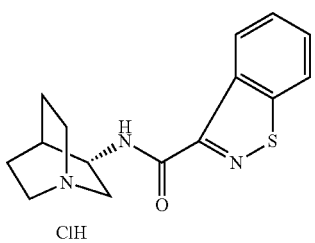

Prepared from benzo[d]isothiazole-3-carboxylic acid using Procedure C. Yield 95%. LC/MS (EI) $t_R$ 3.71 min, m/z 288 (M$^+$+1).

Example 5

N-(1-Azabicyclo[2.2.2]oct-3-yl)-1H-indazole-3-carboxamide

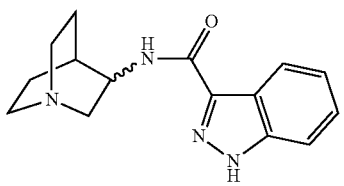

Prepared from 1H-indazole-3-carboxylic acid using Procedure A. Yield 50%. $^1$H NMR (CD$_3$OD) δ 8.21 (m, 1H), 7.56 (m, 1H), 7.42 (m, 1H), 7.24 (m, 1H), 4.19 (m, 1H), 3.32 (m, 1H), 2.96 (m, 5H), 1.95 (m, 5H); MS (EI) m/z 271 (M$^+$+1).

Example 6

N-((3R)-1-Azabicyclo[2.2.2]oct-3-yl)-1H-indazole-3-carboxamide hydrochloride

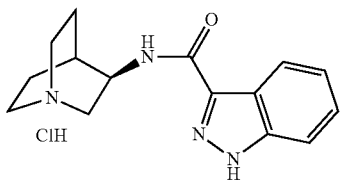

Prepared from 1H-indazole-3-carboxylic acid using Procedure C. Yield 76%. $^1$H NMR (400 MHz CD$_3$OD) δ 8.19 (d, J=8.4, 1H), 7.60 (d, J=8.4, 1H), 7.43 (m, 1H), 7.26 (m, 1H), 4.55 (m, 1H), 3.85 (m, 1H), 3.50 (m, 1H), 3.34 (m, 4H), 2.39 (m, 1H), 2.28 (m, 1H), 2.11 (m, 2H), 1.95 (m, 1H); MS (APCI) m/z 271 (M$^+$+1); m.p. 295° C. (dec.).

Example 7

N-((3S)-1-Azabicyclo[2.2.2]oct-3-yl)-1H-indazole-3-carboxamide hydrochloride

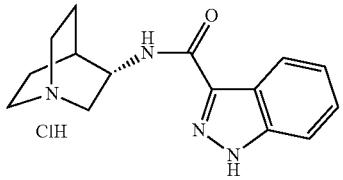

Prepared from 1H-indazole-3-carboxylic acid using Procedure C. Yield 53%. $^1$H NMR (500 MHz, CD$_3$OD) δ 8.19 (d, J=8.0, 1H), 7.60 (d, J=8.5, 1H), 7.43 (m, 1H), 7.26 (m, 1H), 4.55 (m, 1H), 3.85 (m, 1H), 3.50 (m, 1H), 3.34 (m, 4H), 2.39

(m, 1H), 2.28 (m, 1H), 2.11 (m, 2H), 1.95 (m, 1H); MS (APCI) m/z 271 (M⁺+1); m.p. dec. 305° C.

Example 8

N-((3R)-1-Azabicyclo[2.2.2]oct-3-yl)-5-(bromo)benzo[d]isothiazole-3-carboxamide

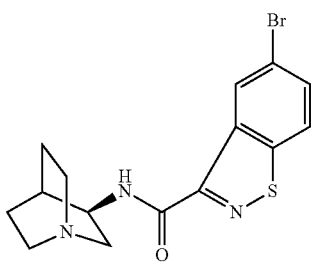

Prepared from 5-bromobenzo[d]isothiazole-3-carboxylic acid using Procedure B. Yield 5%. LC/MS (EI) $t_R$ 4.7 min, m/z 365 (M⁺+1).

Example 9

N-((3R)-1-Azabicyclo[2.2.2]oct-3-yl)-5-(methoxy)benzo[d]isothiazole-3-carboxamide hydroformate

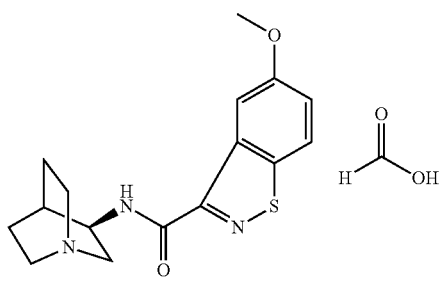

Prepared from 5-methoxybenzo[d]isothiazole-3-carboxylic acid using Procedure B. Yield 5%. LC/MS (EI) $t_R$ 3.14 min, m/z 318 (M⁺+1).

Example 10

N-((3R)-1-Azabicyclo[2.2.2]oct-3-yl)-5-(bromo)-1H-indazole-3-carboxamide

5-Bromo-1H-indazole-3-carboxylic Acid

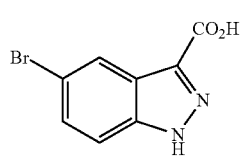

Prepared from 5-bromoisatin using Procedure Q. ¹H NMR (DMSO-d₆) δ 13.9 (broad s, 1H), 8.23 (d, J=1.3, 1H), 7.67 (d, J=8.9, 1H), 7.57 (dd, J=8.9, 1.8, 1H).

N-((3R)-1-Azabicyclo[2.2.2]oct-3-yl)-5-(bromo)-1H-indazole-3-carboxamide

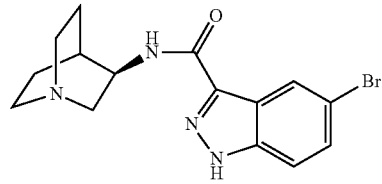

Prepared from 5-bromo-1H-indazole-3-carboxylic acid using Procedure D. Yield 32%. ¹H NMR (DMSO-d₆) δ 8.35 (d, J=7.2, 1H), 8.28 (d, J=1.4, 1H), 7.62 (d, J=8.8, 1 H), 7.52 (dd, J=8.8, 1.8, 1H), 4.00 (m, 1H), 3.11 (m, 2H), 2.90 (m, 1H), 2.67 (m, 4H), 1.82 (m, 2H), 1.59 (t, J=5.6, 2H), 1.30 (m, 1H); ¹H NMR (CD₃OD) δ 8.37 (t, J=1.2, 1H), 7.53 (d, J=1.2, 2H), 4.22 (m, 1H), 3.33 (m, 1H), 3.02 (m, 1H), 2.84 (m, 4H), 2.06 (m, 1H), 1.94 (m, 2H), 1.80 (m, 2H), 1.58 (m, 1H); MS (EI) m/z 349/351 (M⁺/M⁺+2).

Example 11

N-((3R)-1-Azabicyclo[2.2.2]oct-3-yl)-5-(cyclopropyl)-1H-indazole-3-carboxamide hydroformate

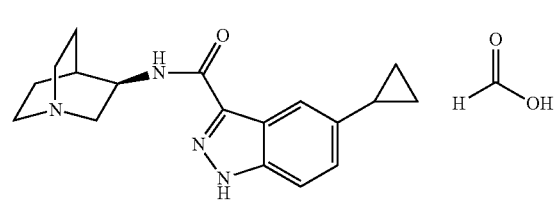

Prepared from N-((3R)-1-azabicyclo[2.2.2]oct-3-yl)-5-bromo-1H-indazole-3-carboxamide using Procedure J. Yield 20% ¹H NMR (CD₃OD) δ 7.89 (s, 1H), 7.48 (d, J=8.7, 1H), 7.21 (dd, J=8.7, 1.6, 1H), 4.54 (m, 1H), 3.82 (m, 1H), 3.42 (m, 1H), 3.35 (m, 4H), 2.38 (m, 1H), 2.28 (m, 1H), 2.11 (m, 3H), 1.92 (m, 1H), 0.98 (m, 2 H), 0.73 (m, 2H); MS (EI) m/z 311 (M⁺+1).

Example 12

N-((3R)-1-Azabicyclo[2.2.2]oct-3-yl)-5-(furan-3-yl)-1H-indazole-3-carboxamide hydroformate

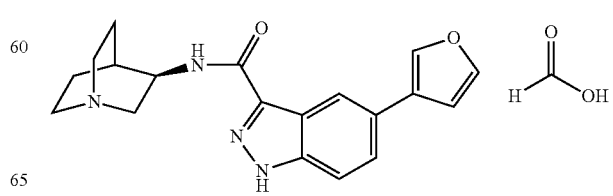

Prepared from N-((3R)-1-azabicyclo[2.2.2]oct-3-yl)-5-bromo-1H-indazole-3-carboxamide using Procedure H. Yield 3%. ¹H NMR (CD₃OD) δ 8.47 (s, 1H), 7.93 (d, J=0.9, 1H), 7.68 (dd, J=8.8, 1.6, 1H), 7.59 (dd, J=8.9, 1.7, 2H), 6.87 (m, 1H), 4.54 (m, 1H), 3.82 (m, 1H), 3.42 (m, 1H), 3.34 (m, 4H), 2.38 (m, 1H), 2.27 (m, 1H), 2.11 (m, 2H), 1.93 (m, 1H); MS (EI) m/z 337 (M⁺+1).

Example 13

N-((3R)-1-Azabicyclo[2.2.2]oct-3-yl)-5-(phenyl)-1H-indazole-3-carboxamide hydroformate

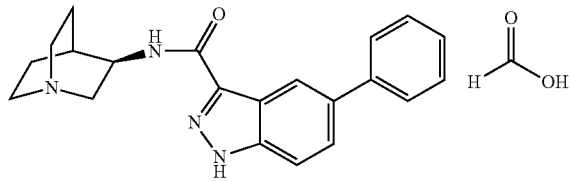

Prepared from N-((3R)-1-azabicyclo[2.2.2]oct-3-yl)-5-bromo-1H-indazole-3-carboxamide using Procedure H. Yield 5%. ¹H NMR (CD₃OD) δ 8.48 (s, 1H), 8.42 (s, 1H), 7.74 (dd, J=8.7, 1.6, 1H), 7.67 (d, J=7.2, 2H), 7.46 (t, J=7.3, 2H), 7.34 (t, J=7.4, 1H), 4.52 (m, 1H), 3.83 (m, 1H), 3.42 (m, 1H), 3.31 (m, 4H), 2.39 (m, 1H), 2.28 (m, 1H), 2.11 (m, 2H), 1.92 (m, 1H); MS (EI) m/z 347 (M⁺+1).

Example 14

N-((3R)-1-Azabicyclo[2.2.2]oct-3-yl)-5-(thiophen-2-yl)-1H-indazole-3-carboxamide

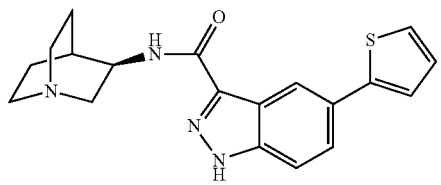

Prepared from N-((3R)-1-azabicyclo[2.2.2]oct-3-yl)-5-bromo-1H-indazole-3-carboxamide using Procedure H. Yield 85%. ¹H NMR (CD₃OD) δ 8.46 (t, J=0.8, 1H), 7.75 (dd, J=8.8, 1.7, 1H), 7.61 (dd, J=8.8, 0.7, 1H), 7.42 (dd, J=3.6, 1.1, 1H), 7.37 (dd, J=5.1, 1.0, 1H), 7.11 (dd, J=5.1, 1.0, 1H), 7.10 (dd, J=5.1, 3.6, 1H), 4.27 (m, 1H), 3.42 (m, 1H), 3.12 (m, 1H), 2.93 (m, 4H), 2.11 (m, 1H), 1.93 (m, 1H), 1.84 (m, 2H), 1.62 (m, 1H); MS (EI) m/z 353 (M⁺+1).

Example 15

N-((3R)-1-Azabicyclo[2.2.2]oct-3-yl)-5-(thiophen-2-yl)-1H-indazole-3-carboxamide hydroformate

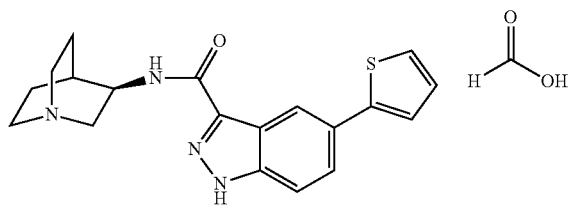

Prepared from N-((3R)-1-azabicyclo[2.2.2]oct-3-yl)-5-bromo-1H-indazole-3-carboxamide using Procedure H. Yield 20%. ¹H NMR (CD₃OD) δ 8.45 (t, J=0.8, 1H), 8.39 (broad s, 1H), 7.78 (dd, J=8.8, 1.7, 1H), 7.62 (dd, J=8.8, 0.8, 1H), 7.42 (dd, J=3.6, 1.1, 1H), 7.38 (dd, J=5.1, 1.0, 1H), 7.11 (dd, J=5.1, 3.6, 1H), 4.55 (m, 1H), 3.83 (m, 1H), 3.46 (m, 1H), 3.37 (m, 4H), 2.40 (m, 1H), 2.25 (m, 1H), 2.10 (m, 2 H), 1.93 (m, 1H); MS (EI) m/z 353 (M⁺+1).

Example 16

N-((3R)-1-Azabicyclo[2.2.2]oct-3-yl)-5-(thiophen-3-yl)-1H-indazole-3-carboxamide hydroformate

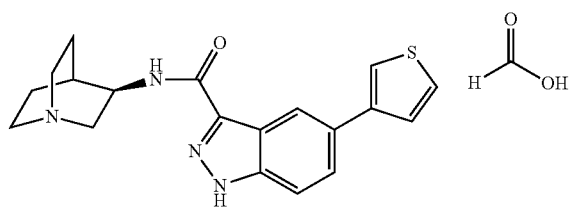

Prepared from N-((3R)-1-azabicyclo[2.2.2]oct-3-yl)-5-bromo-1H-indazole-3-carboxamide using Procedure H. Yield 5%. ¹H NMR (CD₃OD) δ 8.55 (broad s, 1H), 8.45 (d, J=0.7, 1H), 7.78 (dd, J=8.8, 1.6, 1H), 7.62 (m, 1H), 7.51 (m, 2H), 4.52 (m, 1H), 3.78 (m, 1H), 3.42 (m, 1H), 3.35 (m, 4H), 2.37 (m, 1H), 2.25 (m, 1H), 2.06 (m, 2H), 1.90 (m, 1H); MS (EI) m/z 353 (M⁺+1).

Example 17

N-((3S)-1-Azabicyclo[2.2.2]oct-3-yl)-5-(bromo)benzo[d]isothiazole-3-carboxamide

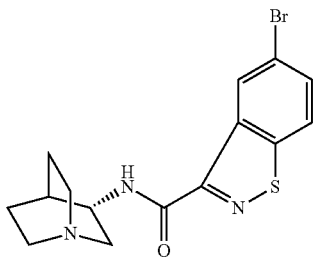

Prepared from 5-bromobenzo[d]isothiazole-3-carboxylic acid using Procedure B. Yield 5%. LC/MS (EI) t_R 5.36 min, m/z 365 (M⁺+1).

Example 18

N-((3S)-1-Azabicyclo[2.2.2]oct-3-yl)-5-methoxybenzo[d]isothiazole-3-carboxamide hydroformate

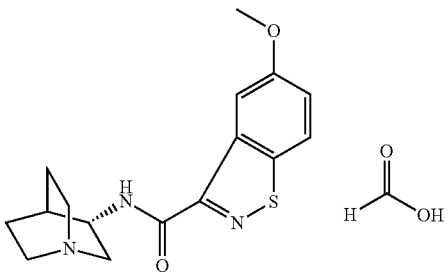

Prepared from 5-methoxybenzo[d]isothiazole-3-carboxylic acid using Procedure B. Yield 7%. LC/MS (EI) t_R 3.38 min, m/z 318 (M⁺+1).

Example 19

N-((3S)-1-Azabicyclo[2.2.2]oct-3-yl)-5-(bromo)-1H-indazole-3-carboxamide

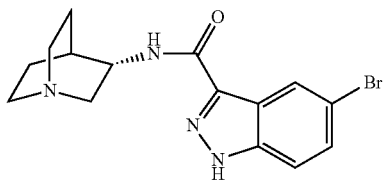

Prepared from 5-bromo-1H-indazole-3-carboxylic acid using Procedure D. Yield 31%. $^1$H NMR (DMSO-d$_6$) δ 8.35 (d, J=7.2, 1H), 8.28 (d, J=1.4, 1H), 7.62 (d, J=8.8, 1 H), 7.52 (dd, J=8.8, 1.8, 1H), 4.00 (m, 1H), 3.11 (m, 2H), 2.90 (m, 1H), 2.67 (m, 4 H), 1.82 (m, 2H), 1.59 (t, J=5.6, 2H), 1.30 (m, 1H); $^1$H NMR (CD$_3$OD) δ 8.37 (t, J=1.2, 1H), 7.53 (d, J=1.2, 2H), 4.22 (m, 1H), 3.33 (m, 1H), 3.02 (m, 1H), 2.84 (m, 4H), 2.06 (m, 1H), 1.94 (m, 2H), 1.80 (m, 2H), 1.58 (m, 1H); MS (EI) m/z 349/351 (M$^+$/M$^+$+2).

Example 20

N-((3S)-1-Azabicyclo[2.2.2]oct-3-yl)-5-(furan-3-yl)-1H-indazole-3-carboxamide hydroformate

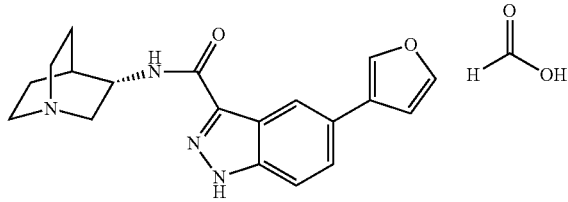

Prepared from N-((3S)-1-azabicyclo[2.2.2]oct-3-yl)-5-bromo-1H-indazole-3-carboxamide using Procedure H. Yield 11%. $^1$H NMR (CD$_3$OD) δ 8.47 (s, 1H), 7.93 (d, J=0.9, 1H), 7.68 (dd, J=8.8, 1.6, 1H), 7.59 (dd, J=8.9, 1.7, 2H), 6.87 (m, 1H), 4.54 (m, 1H), 3.82 (m, 1H), 3.42 (m, 1H), 3.34 (m, 4H), 2.38 (m, 1H), 2.27 (m, 1 H), 2.11 (m, 2H), 1.93 (m, 1H); MS (EI) m/z 337 (M$^+$+1).

Example 21

N-((3S)-1-Azabicyclo[2.2.2]oct-3-yl)-5-(phenyl)-1H-indazole-3-carboxamide hydroformate

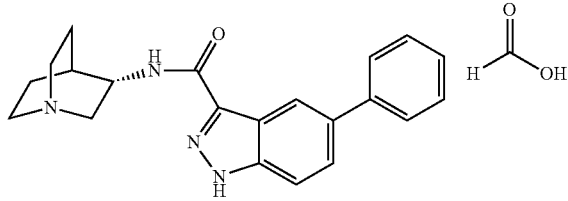

Prepared from N-((3S)-1-azabicyclo[2.2.2]oct-3-yl)-5-bromo-1H-indazole-3-carboxamide using Procedure H. Yield 12%. $^1$H NMR (CD$_3$OD) δ 8.48 (s, 1H), 8.42 (s, 1H), 7.74 (dd, J=8.7, 1.6, 1H), 7.67 (d, J=7.2, 2H), 7.46 (t, J=7.3, 2H), 7.34 (t, J=7.4, 1H), 4.52 (m, 1H), 3.83 (m, 1H), 3.42 (m, 1H), 3.31 (m, 4H), 2.39 (m, 1 H), 2.28 (m, 1H), 2.11 (m, 2H), 1.92 (m, 1H); MS (EI) m/z 347 (M$^+$+1).

Example 22

N-((3S)-1-Azabicyclo[2.2.2]oct-3-yl)-5-(thiophen-2-yl)-1H-indazole-3-carboxamide hydroformate

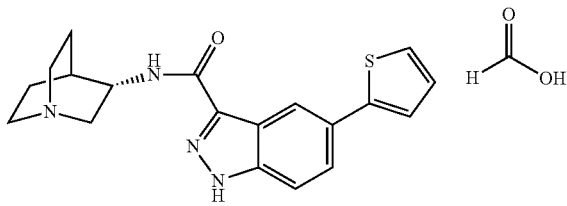

Prepared from N-((3S)-1-azabicyclo[2.2.2]oct-3-yl)-5-bromo-1H-indazole-3-carboxamide using Procedure H. Yield 45%. $^1$H NMR (CD$_3$OD) δ 8.45 (t, J=0.8, 1H), 8.39 (broad s, 1H), 7.78 (dd, J=8.8, 1.7, 1H), 7.62 (dd, J=8.8, 0.8, 1H), 7.42 (dd, J=3.6, 1.1, 1H), 7.38 (dd, J=5.1, 1.0, 1H), 7.11 (dd, J=5.1, 3.6, 1H), 4.55 (m, 1H), 3.83 (m, 1H), 3.46 (m, 1H), 3.37 (m, 4H), 2.40 (m, 1H), 2.25 (m, 1H), 2.10 (m, 2 H), 1.93 (m, 1H); MS (EI) m/z 353 (M$^+$+1).

Example 23

N-((3S)-1-Azabicyclo[2.2.2]oct-3-yl)-5-(thiophen-3-yl)-1H-indazole-3-carboxamide hydroformate

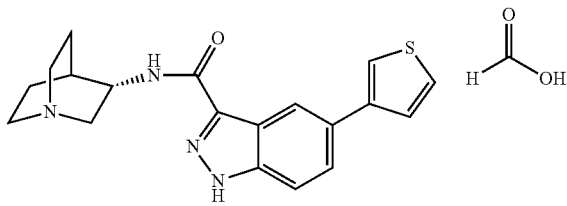

Prepared from N-((3S)-1-azabicyclo[2.2.2]oct-3-yl)-5-bromo-1H-indazole-3-carboxamide using Procedure H. Yield 20%. $^1$H NMR (CD$_3$OD) δ 8.55 (broad s, 1H), 8.45 (d, J=0.7, 1H), 7.78 (dd, J=8.8, 1.6, 1H), 7.62 (m, 1H), 7.51 (m, 2H), 4.52 (m, 1H), 3.78 (m, 1H), 3.42 (m, 1H), 3.35 (m, 4H), 2.37 (m, 1H), 2.25 (m, 1 H), 2.06 (m, 2H), 1.90 (m, 1H); MS (EI) m/z 353 (M$^+$+1).

Example 24

N-((3R)-1-Azabicyclo[2.2.2]oct-3-yl)-6-bromobenzo[d]isothiazole-3-carboxamide

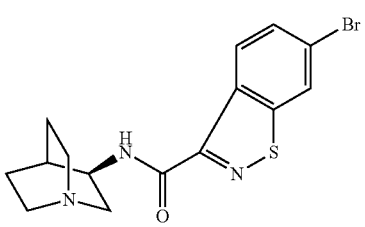

Prepared from 6-bromobenzo[d]isothiazole-3-carboxylic acid using Procedure B. Yield 39%. LC/MS (EI) $t_R$ 4.75 min, m/z 365 (M$^+$+1).

Example 25

N-((3R)-1-Azabicyclo[2.2.2]oct-3-yl)-6-cyclopropylbenzo[d]isothiazole-3-carboxamide

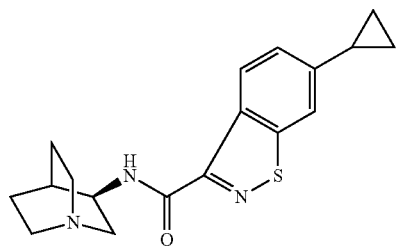

Prepared from N-((3R)-1-azabicyclo[2.2.2]oct-3-yl)-6-bromobenzo[d]isothiazole-3-carboxamide using Procedure J. Yield 45%. LC/MS (EI) $t_R$ 4.25 min, m/z 328 (M$^+$+1).

Example 26

N-((3R)-1-Azabicyclo[2.2.2]oct-3-yl)-6-(2-fluorophenyl)benzo[d]isothiazole-3-carboxamide

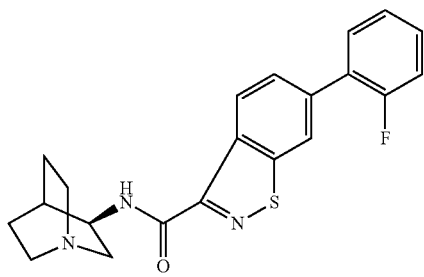

Prepared from N-((3R)-1-azabicyclo[2.2.2]oct-3-yl)-6-bromobenzo[d]isothiazole-3-carboxamide using Procedure H. Yield 37%. LC/MS (EI) $t_R$ 5.95 min, m/z 382 (M$^+$+1).

Example 27

N-((3R)-1-Azabicyclo[2.2.2]oct-3-yl)-6-(2-fluorophenyl)benzo[d]isothiazole-3-carboxamide hydroformate

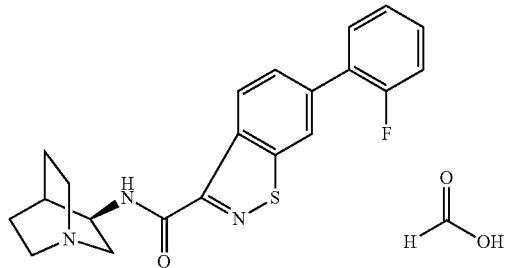

Prepared from N-((3R)-1-azabicyclo[2.2.2]oct-3-yl)-6-bromobenzo[d]isothiazole-3-carboxamide using Procedure H. Yield 8%. LC/MS (EI) $t_R$ 4.52 min, m/z 382 (M$^+$+1).

Example 28

N-((3R)-1-Azabicyclo[2.2.2]oct-3-yl)-6-(3-fluorophenyl)benzo[d]isothiazole-3-carboxamide

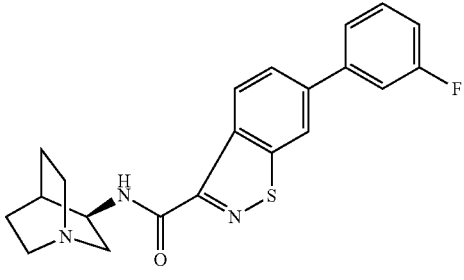

Prepared from N-((3R)-1-azabicyclo[2.2.2]oct-3-yl)-6-bromobenzo[d]isothiazole-3-carboxamide using Procedure H. Yield 38%. LC/MS (EI) $t_R$ 5.92 min, m/z 382 (M$^+$+1).

Example 29

N-((3R)-1-Azabicyclo[2.2.2]oct-3-yl)-6-(3-fluorophenyl)benzo[d]isothiazole-3-carboxamide hydroformate

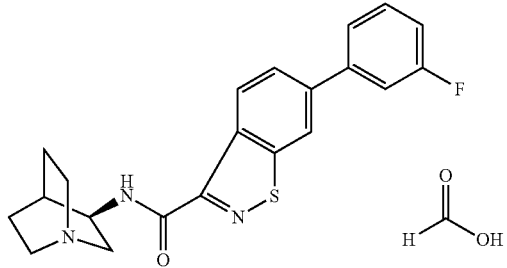

Prepared from N-((3R)-1-azabicyclo[2.2.2]oct-3-yl)-6-bromobenzo[d]isothiazole-3-carboxamide using Procedure H. Yield 10%. LC/MS (EI) $t_R$ 4.56 min, m/z 382 (M$^+$+1).

Example 30

N-((3R)-1-Azabicyclo[2.2.2]oct-3-yl)-6-(4-fluorophenyl)benzo[d]isothiazole-3-carboxamide

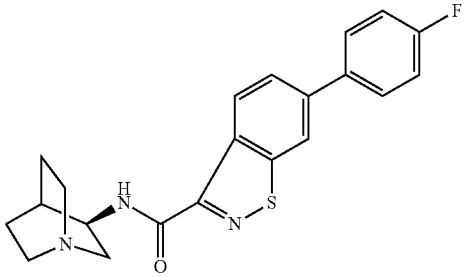

Prepared from N-((3R)-1-azabicyclo[2.2.2]oct-3-yl)-6-bromobenzo[d]isothiazole-3-carboxamide using Procedure H. Yield 34%. LC/MS (EI) $t_R$ 5.92 min, m/z 382 (M$^+$+1).

Example 31

N-((3R)-1-Azabicyclo[2.2.2]oct-3-yl)-6-(4-fluorophenyl)benzo[d]isothiazole-3-carboxamide hydroformate

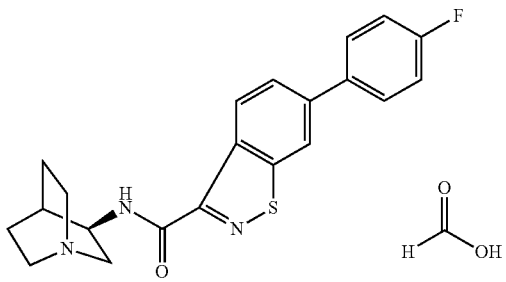

Prepared from N-((3R)-1-azabicyclo[2.2.2]oct-3-yl)-6-bromobenzo[d]isothiazole-3-carboxamide using Procedure H. Yield 9%. LC/MS (EI) $t_R$ 4.57 min, m/z 382 (M$^+$+1).

Example 32

N-((3R)-1-Azabicyclo[2.2.2]oct-3-yl)-6-(3-furan-3-yl)benzo[d]isothiazole-3-carboxamide

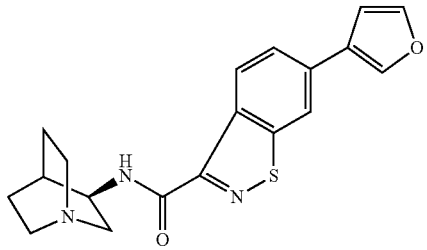

Prepared from N-((3R)-1-azabicyclo[2.2.2]oct-3-yl)-6-bromobenzo[d]isothiazole-3-carboxamide using Procedure H. Yield 14%. LC/MS (EI) $t_R$ 4.32 min, m/z 354 (M$^+$+1).

Example 33

N-((3R)-1-Azabicyclo[2.2.2]oct-3-yl)-6-(3-furan-3-yl)benzo[d]isothiazole-3-carboxamide hydroformate

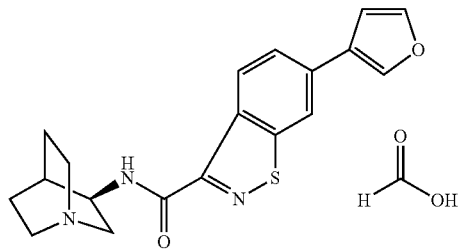

Prepared from N-((3R)-1-azabicyclo[2.2.2]oct-3-yl)-6-bromobenzo[d]isothiazole-3-carboxamide using Procedure H. Yield 11%. LC/MS (EI) $t_R$ 4.32 min, m/z 354 (M$^+$+1).

Example 34

N-((3R)-1-Azabicyclo[2.2.2]oct-3-yl)-6-methoxybenzo[d]isothiazole-3-carboxamide

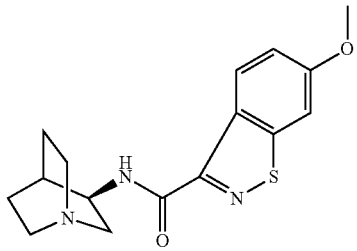

Prepared from 5-methoxybenzo[d]isothiazole-3-carboxylic acid using Procedure B. Yield 73%. $^1$H NMR (CD$_3$OD) δ 8.59 (d, J=9.1, 1H), 7.59 (d, J=2.2, 1H), 7.14 (dd, J=9.1, 2.3, 1H), 4.20 (m, 1H), 3.93 (s, 3H), 3.37-3.28 (m, 1H), 3.05-2.96 (m, 1H), 2.86-2.79 (m, 2H), 2.07-2.04 (m, 1H), 2.02-1.80 (m, 1H), 1.78-1.74 (m, 1H), 1.56-1.52 (m, 1H); LC/MS (EI) $t_R$ 4.92 min, m/z 318 m/z (M$^+$+1).

Example 35

N-((3R)-1-Azabicyclo[2.2.2]oct-3-yl)-6-(morpholin-4-yl)benzo[d]isothiazole-3-carboxamide hydroformate

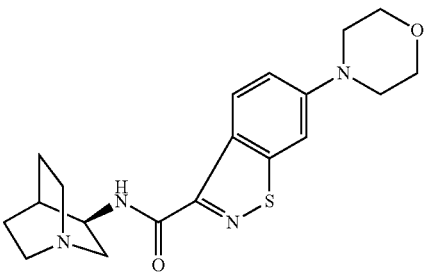

Prepared from N-((3R)-1-azabicyclo[2.2.2]oct-3-yl)-6-bromobenzo[d]isothiazole-3-carboxamide using Procedure I. Yield 34%. $^1$H NMR (CD$_3$OD) δ 8.54 (d, J=9.2, 1H), 7.45 (d, J=2.1, 1H), 7.29 (dd, J=9.2, 2.2, 1H), 4.22-4.19 (m, 1H), 3.88-3.85 (m, 2H), 3.68-3.65 (m, 2H), 3.38-3.30 (m, 5H), 3.09-3.01 (m, 2H), 2.95-2.81 (m, 4H), 2.09-2.06 (m, 1H), 1.97-1.84 (m, 1H), 1.82-1.79 (m, 2H), 1.62-1.54 (m, 1H); LC/MS (EI) $t_R$ 4.77 min, m/z 373 (M$^+$+1).

Example 36

N-((3R)-1-Azabicyclo[2.2.2]oct-3-yl)-6-phenyl-benzo[d]isothiazole-3-carboxamide

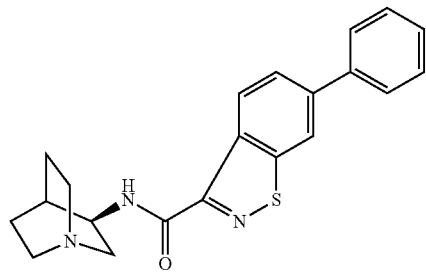

Prepared from N-((3R)-1-azabicyclo[2.2.2]oct-3-yl)-6-bromobenzo[d]isothiazole-3-carboxamide using Procedure H. Yield 37%. LC/MS (EI) $t_R$ 5.99 min, m/z 364 (M$^+$+1).

Example 37

N-((3R)-1-Azabicyclo[2.2.2]oct-3-yl)-6-phenyl-benzo[d]isothiazole-3-carboxamide hydroformate

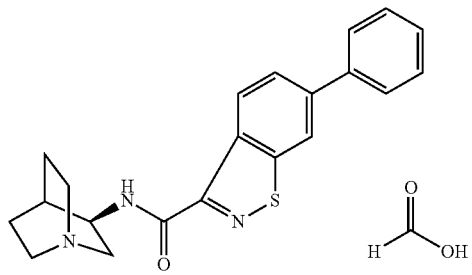

Prepared from N-((3R)-1-azabicyclo[2.2.2]oct-3-yl)-6-bromobenzo[d]isothiazole-3-carboxamide using Procedure H. Yield 3%. LC/MS (EI) $t_R$ 5.99 min, m/z 364 (M$^+$+1).

Example 38

N-((3R)-1-Azabicyclo[2.2.2]oct-3-yl)-6-(pyridin-3-yl)benzo[d]isothiazole-3-carboxamide

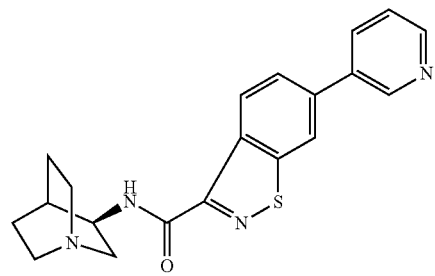

Prepared from N-((3R)-1-azabicyclo[2.2.2]oct-3-yl)-6-bromobenzo[d]isothiazole-3-carboxamide using Procedure H. Yield 19%. LC/MS (EI) $t_R$ 2.94 min, m/z 365 (M$^+$+1).

Example 39

N-((3R)-1-Azabicyclo[2.2.2]oct-3-yl)-6-(pyridin-3-yl)benzo[d]isothiazole-3-carboxamide hydroformate

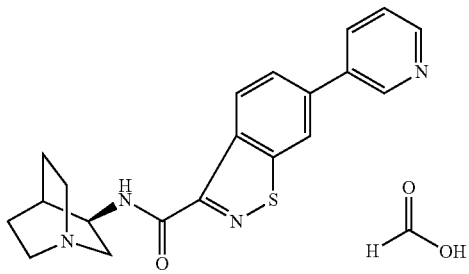

Prepared from N-((3R)-1-azabicyclo[2.2.2]oct-3-yl)-6-bromobenzo[d]isothiazole-3-carboxamide using Procedure H. Yield 5%. LC/MS (EI) $t_R$ 2.94 min, m/z 365 (M$^+$+1).

Example 40

N-((3R)-1-Azabicyclo[2.2.2]oct-3-yl)-6-(pyridin-4-yl)benzo[d]isothiazole-3-carboxamide

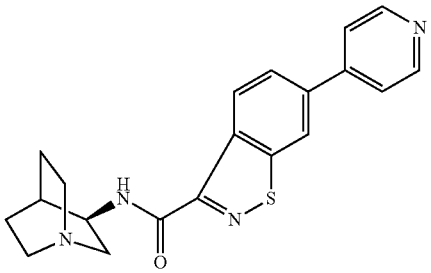

Prepared from N-((3R)-1-azabicyclo[2.2.2]oct-3-yl)-6-bromobenzo[d]isothiazole-3-carboxamide using Procedure H. Yield 15%. LC/MS (EI) $t_R$ 2.96 min, m/z 365 (M$^+$+1).

Example 41

N-((3R)-1-Azabicyclo[2.2.2]oct-3-yl)-6-(pyridin-4-yl)benzo[d]isothiazole-3-carboxamide hydroformate

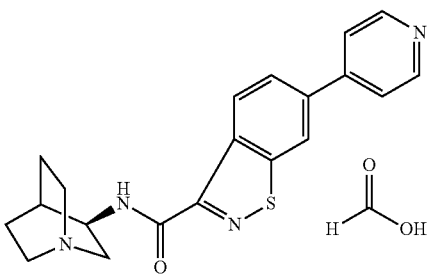

Prepared from N-((3R)-1-azabicyclo[2.2.2]oct-3-yl)-6-bromobenzo[d]isothiazole-3-carboxamide using Procedure H. Yield 2%. LC/MS (EI) $t_R$ 1.56 min, m/z 365 (M$^+$+1).

Example 42

N-((3R)-1-Azabicyclo[2.2.2]oct-3-yl)-6-(thiophen-2-yl)benzo[d]isothiazole-3-carboxamide

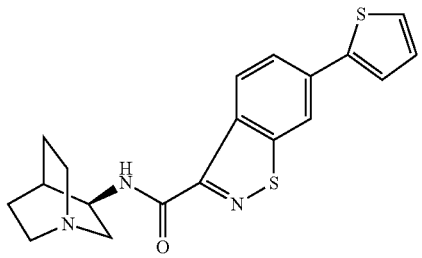

Prepared from N-((3R)-1-azabicyclo[2.2.2]oct-3-yl)-6-bromobenzo[d]isothiazole-3-carboxamide using Procedure H. Yield 16%. LC/MS (EI) $t_R$ 4.52 min, m/z 370 (M$^+$+1).

Example 43

N-((3R)-1-Azabicyclo[2.2.2]oct-3-yl)-6-(thiophen-3-yl)benzo[d]isothiazole-3-carboxamide

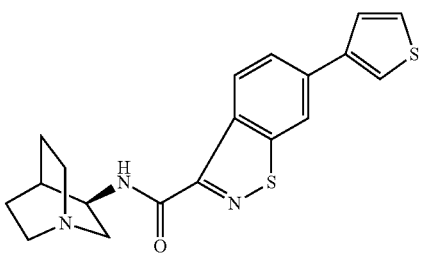

Prepared from N-((3R)-1-azabicyclo[2.2.2]oct-3-yl)-6-bromobenzo[d]isothiazole-3-carboxamide using Procedure H. Yield 61%. $^1$H NMR (CD$_3$OD) δ 8.74 (d, J=8.6, 1H), 8.36 (s, 1H), 7.85 (dd, J=8.6, 1.4, 1H), 7.62 (d, J=3.5, 1H), 7.51 (m, 1H), 7.17 (dd, J=5.0, 3.7, 1H), 4.52 (M, 1H), 3.87-3.79 (m, 1H), 3.75-3.70 (m, 1H), 3.47-3.19 (m, 4H), 2.40 (m, 1H), 2.26 (m, 1H), 2.11 (m, 1H), 1.93 (m, 1H); LC/MS (EI) $t_R$ 4.42 min, m/z 370 (M$^+$+1).

Example 44

N-((3R)-1-Azabicyclo[2.2.2]oct-3-yl)-6-(bromo)-1H-indazole-3-carboxamide

6-Bromo-1H-indazole-3-carboxylic acid

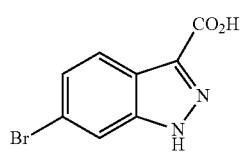

Prepared from 6-bromoisatin using Procedure Q. $^1$H NMR (DMSO-d$_6$) δ 13.7 (broad s, 1H), 8.02 (d, J=8.5, 1H), 7.60 (d, J=1.3, 1H), 7.43 (dd, J=8.7, 1.3, 1H).

N-((3R)-1-Azabicyclo[2.2.2]oct-3-yl)-6-(bromo)-1H-indazole-3-carboxamide

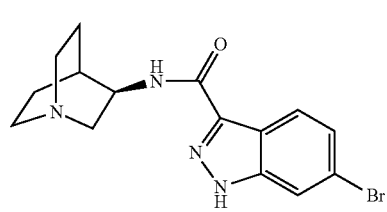

Prepared from 6-bromo-1H-indazole-3-carboxylic acid using Procedure D. Yield 23%. $^1$H NMR (CD$_3$OD) δ 8.10 (d, J=8.7, 1H), 7.78 (s, 1H), 7.37 (d, J=8.7, 1H), 4.20 (m, 1H), 3.30 (m, 6H), 2.08 (m, 1H), 1.95 (m, 1H), 1.83 (m, 2H), 1.80 (m, 1 H); MS (EI) m/z 349/351 (M$^+$/M$^+$+2).

Example 45

N-((3R)-1-Azabicyclo[2.2.2]oct-3-yl)-6-(furan-3-yl)-1H-indazole-3-carboxamide hydroformate

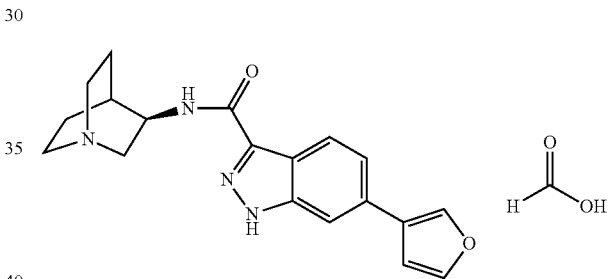

Prepared from N-((3R)-1-azabicyclo[2.2.2]oct-3-yl)-6-bromo-1H-indazole-3-carboxamide using Procedure H. Yield 12%. $^1$H NMR (CD$_3$OD) δ 8.49 (s, 11-1), 8.16 (m, 1H), 8.00 (s, 1H), 7.71 (m, 1H), 7.59 (m, 1H), 7.52 (m, 1H), 7.50 (m, 1 H), 4.53 (m, 1H), 3.35 (m, 1H), 3.28 (m, 5H), 2.37 (m, 1H), 2.30 (m, 1H), 2.10 (m, 2H), 1.85 (m, 1H); MS (EI) m/z 337 (M$^+$+1).

Example 46

N-((3R)-1-Azabicyclo[2.2.2]oct-3-yl)-6-(phenyl)-1H-indazole-3-carboxamide hydroformate

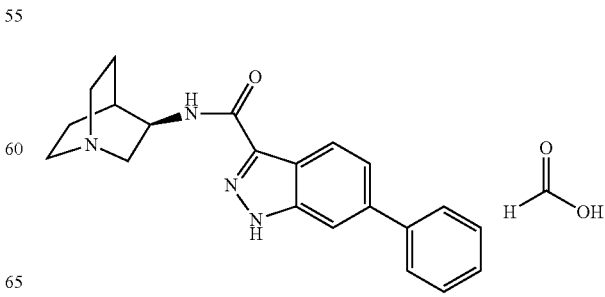

Prepared from N-((3R)-1-azabicyclo[2.2.2]oct-3-yl)-6-bromo-1H-indazole-3-carboxamide using Procedure H. Yield 12%. ¹H NMR (CD₃OD) δ 8.39 (s, 1H), 8.24 (m, 1H), 7.77 (s, 1H), 7.68 (m, 2H), 7.57 (m, 1H), 7.50 (m, 2H), 4.53 (m, 1 H), 3.35 (m, 1H), 3.28 (m, 5H), 2.37 (m, 1H), 2.30 (m, 1H), 2.10 (m, 2H), 1.85 (m, 1 H); MS (EI) m/z 347 (M⁺+1).

Example 47

N-((3R)-1-Azabicyclo[2.2.2]oct-3-yl)-6-(thiophen-2-yl)-1H-indazole-3-carboxamide hydroformate

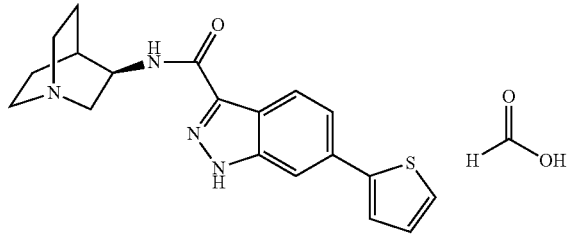

Prepared from N-((3R)-1-azabicyclo[2.2.2]oct-3-yl)-6-bromo-1H-indazole-3-carboxamide using Procedure H. Yield 13%. ¹H NMR (CD₃OD) δ 8.49 (s, 1H), 8.21 (m, 1H), 7.81 (s, 1H), 7.74 (m, 1H), 7.64 (m, 1H), 7.53 (m, 2H), 4.53 (m, 1 H), 3.35 (m, 1H), 3.28 (m, 5H), 2.37 (m, 1H), 2.30 (m, 1H), 2.10 (m, 2H), 1.85 (m, 1 H); MS (EI) m/z 353 (M⁺+1).

Example 48

N-((3R)-1-Azabicyclo[2.2.2]oct-3-yl)-6-(thiophen-3-yl)-1H-indazole-3-carboxamide hydroformate

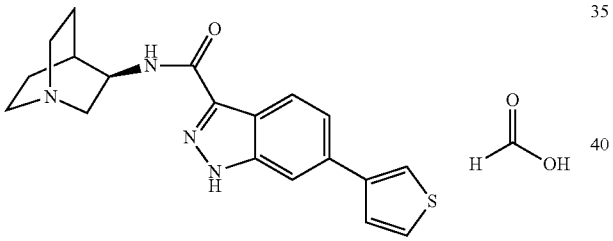

Prepared from N-((3R)-1-azabicyclo[2.2.2]oct-3-yl)-6-bromo-1H-indazole-3-carboxamide using Procedure H. Yield 19%. ¹H NMR (CD₃OD) δ 8.48 (s, 1H), 8.20 (m, 1H), 7.80 (s, 1H), 7.62 (m, 1H), 7.51 (m, 1H), 7.44 (m, 1H), 7.13 (m, 1 H), 4.53 (m, 1H), 3.35 (m, 1H), 3.28 (m, 5H), 2.37 (m, 1H), 2.30 (m, 1H), 2.10 (m, 2H), 1.85 (m, 1H); MS (EI) m/z 353 (M⁺+1).

Example 49

N-((3S)-1-Azabicyclo[2.2.2]oct-3-yl)-6-bromobenzo[d]isothiazole-3-carboxamide

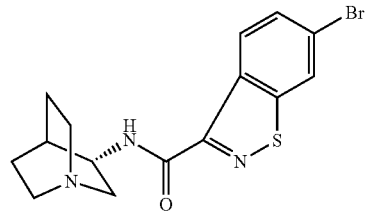

Prepared from 6-bromobenzo[d]isothiazole-3-carboxylic acid using Procedure B. Yield 33%. LC/MS (EI) $t_R$ 5.44 min, m/z 365 (M⁺+1).

Example 50

N-((3S)-1-Azabicyclo[2.2.2]oct-3-yl)-6-cyclopropyl-benzo[d]isothiazole-3-carboxamide

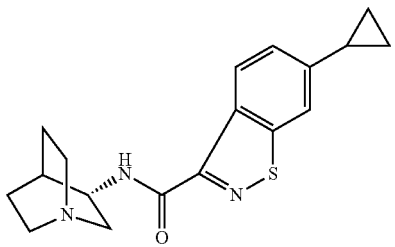

Prepared from N-((3S)-1-azabicyclo[2.2.2]oct-3-yl)-6-bromobenzo[d]isothiazole-3-carboxamide using Procedure J. Yield 40%. LC/MS (EI) $t_R$ 4.23 min, m/z 328 (M⁺+1).

Example 51

N-((3S)-1-Azabicyclo[2.2.2]oct-3-yl)-6-(2-fluorophenyl)benzo[d]isothiazole-3-carboxamide hydroformate

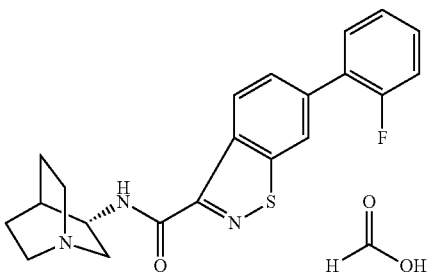

Prepared from N-((3S)-1-azabicyclo[2.2.2]oct-3-yl)-6-bromobenzo[d]isothiazole-3-carboxamide using Procedure H. Yield 13%. LC/MS (EI) $t_R$ 4.52 min, m/z 382 (M⁺+1).

Example 52

N-((3S)-1-Azabicyclo[2.2.2]oct-3-yl)-6-(3-fluorophenyl)benzo[d]isothiazole-3-carboxamide hydroformate

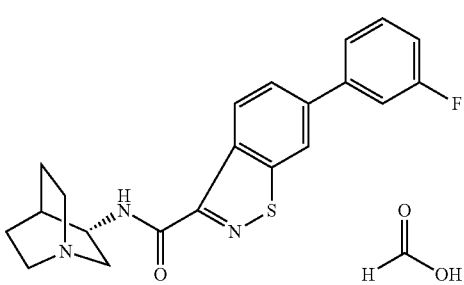

Prepared from N-((3S)-1-azabicyclo[2.2.2]oct-3-yl)-6-bromobenzo[d]isothiazole-3-carboxamide using Procedure H. Yield 8%. LC/MS (EI) $t_R$ 4.56 min, m/z 382 (M$^+$+1).

Example 53

N-((3S)-1-Azabicyclo[2.2.2]oct-3-yl)-6-(4-fluorophenyl)benzo[d]isothiazole-3-carboxamide hydroformate

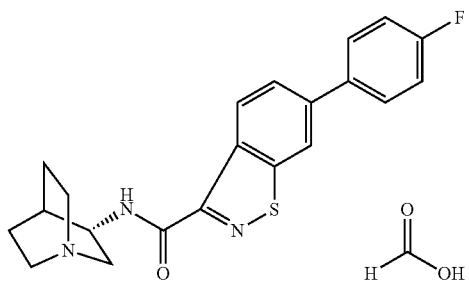

Prepared from N-((3S)-1-azabicyclo[2.2.2]oct-3-yl)-6-bromobenzo[d]isothiazole-3-carboxamide using Procedure H. Yield 15%. LC/MS (EI) $t_R$ 4.56 min, m/z 382 (M$^+$+1).

Example 54

N-((3S)-1-Azabicyclo[2.2.2]oct-3-yl)-6-(furan-3-yl)benzo[d]isothiazole-3-carboxamide hydroformate

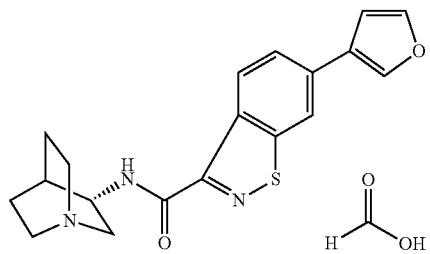

Prepared from N-((3S)-1-azabicyclo[2.2.2]oct-3-yl)-6-bromobenzo[d]isothiazole-3-carboxamide using Procedure H. Yield 24%. LC/MS (EI) $t_R$ 4.29 min, m/z 354 (M$^+$+1).

Example 55

N-((3S)-1-Azabicyclo[2.2.2]oct-3-yl)-6-methoxybenzo[d]isothiazole-3-carboxamide

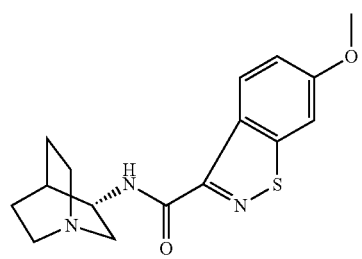

Prepared from 5-methoxybenzo[d]isothiazole-3-carboxylic acid using Procedure B. Yield 73%. LC/MS (EI) $t_R$ 4.93 min, m/z 318 (M$^+$+1).

Example 56

N-((3S)-1-Azabicyclo[2.2.2]oct-3-yl)-6-(morpholin-4-yl)benzo[d]isothiazole-3-carboxamide hydroformate

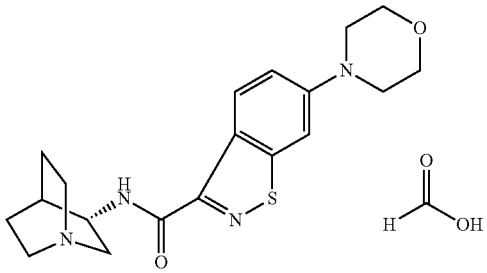

Prepared from N-((3S)-1-azabicyclo[2.2.2]oct-3-yl)-6-bromobenzo[d]isothiazole-3-carboxamide using Procedure I. Yield 5%. LC/MS (EI) $t_R$ 2.93 min, m/z 373 (M$^+$+1).

Example 57

N-((3S)-1-Azabicyclo[2.2.2]oct-3-yl)-6-phenylbenzo[d]isothiazole-3-carboxamide hydroformate

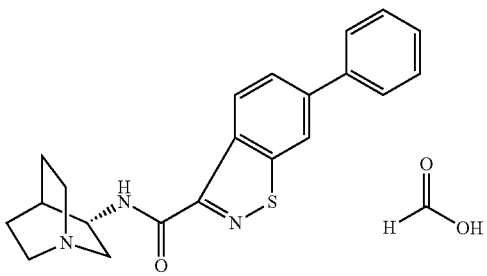

Prepared from N-((3S)-1-azabicyclo[2.2.2]oct-3-yl)-6-bromobenzo[d]isothiazole-3-carboxamide using Procedure H. Yield 9%. LC/MS (EI) $t_R$ 4.53 min, m/z 364 (M$^+$+1).

Example 58

N-((3S)-1-Azabicyclo[2.2.2]oct-3-yl)-6-(pyridin-3-yl)benzo[d]isothiazole-3-carboxamide hydroformate

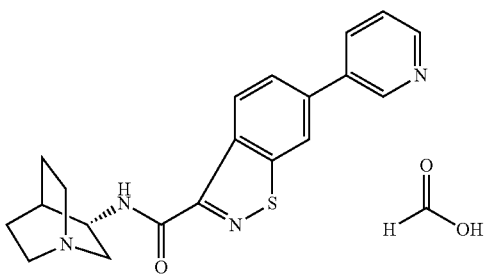

Prepared from N-((3S)-1-azabicyclo[2.2.2]oct-3-yl)-6-bromobenzo[d]isothiazole-3-carboxamide using Procedure H. Yield 8%. LC/MS (EI) $t_R$ 2.72 min, m/z 365 (M$^+$+1).

Example 59

N-((3S)-1-Azabicyclo[2.2.2]oct-3-yl)-6-(pyridin-4-yl)benzo[d]isothiazole-3-carboxamide hydroformate

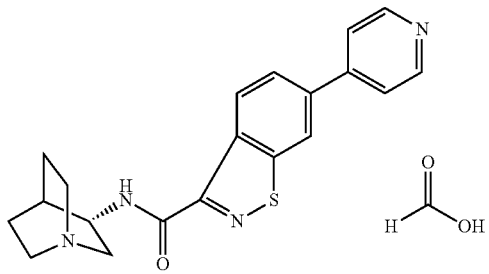

Prepared from N-((3S)-1-azabicyclo[2.2.2]oct-3-yl)-6-bromobenzo[d]isothiazole-3-carboxamide using Procedure H. Yield 5%. LC/MS (EI) $t_R$ 2.63 min, m/z 365 (M$^+$+1).

Example 60

N-((3S)-1-Azabicyclo[2.2.2]oct-3-yl)-6-(thiophen-2-yl)benzo[d]isothiazole-3-carboxamide hydroformate

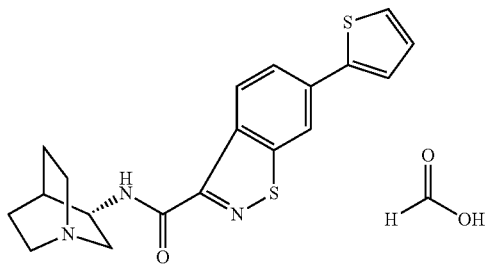

Prepared from N-((3S)-1-azabicyclo[2.2.2]oct-3-yl)-6-bromobenzo[d]isothiazole-3-carboxamide using Procedure H. Yield 27%. LC/MS (EI) $t_R$ 4.48 min, m/z 370 (M$^+$+1).

Example 61

N-((3S)-1-Azabicyclo[2.2.2]oct-3-yl)-6-(thiophen-3-yl)benzo[d]isothiazole-3-carboxamide

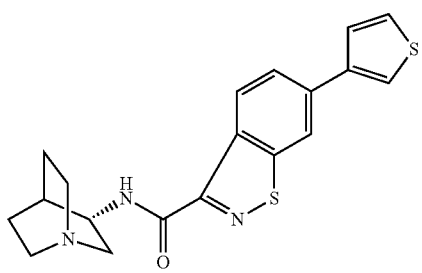

Prepared from N-((3S)-1-azabicyclo[2.2.2]oct-3-yl)-6-bromobenzo[d]isothiazole-3-carboxamide using Procedure H. Yield 61%. LC/MS (EI) $t_R$ 4.41 min, m/z 370 (M$^+$+1).

Example 62

N-((3S)-1-Azabicyclo[2.2.2]oct-3-yl)-6-(bromo)-1H-indazole-3-carboxamide

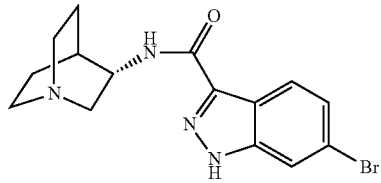

Prepared from 6-bromo-1H-indazole-3-carboxylic acid using Procedure D. Yield 19%. $^1$H NMR (CD$_3$OD) δ 8.10 (d, J=8.7, 1H), 7.78 (s, 1H), 7.37 (d, J=8.7, 1H), 4.20 (m, 1H), 3.30 (m, 6H), 2.08 (m, 1H), 1.95 (m, 1H), 1.83 (m, 2H), 1.80 (m, 1 H); MS (EI) m/z 349/351 (M$^+$/M$^+$+2).

Example 63

N-((3S)-1-Azabicyclo[2.2.2]oct-3-yl)-6-(furan-3-yl)-1H-indazole-3-carboxamide hydroformate

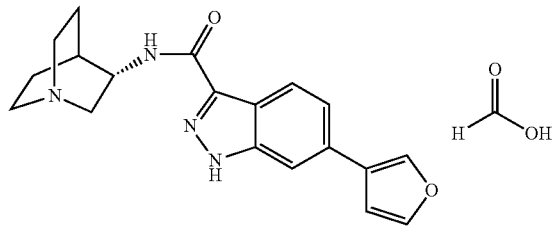

Prepared from N-((3S)-1-azabicyclo[2.2.2]oct-3-yl)-6-bromo-1H-indazole-3-carboxamide using Procedure H. Yield 12%. $^1$H NMR (CD$_3$OD) δ 8.49 (s, 1H), 8.21 (m, 1H), 7.81 (s, 1H), 7.74 (m, 1H), 7.64 (m, 1H), 7.53 (m, 2H), 4.53 (m, 1 H), 3.35 (m, 1H), 3.28 (m, 5H), 2.37 (m, 1H), 2.30 (m, 1H), 2.10 (m, 2H), 1.85 (m, 1 H); MS (EI) m/z 337 (M$^+$+1).

Example 64

N-((3S)-1-Azabicyclo[2.2.2]oct-3-yl)-6-(phenyl)-1H-indazole-3-carboxamide hydroformate

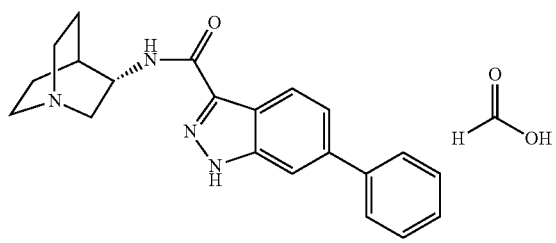

Prepared from N-((3S)-1-azabicyclo[2.2.2]oct-3-yl)-6-bromo-1H-indazole-3-carboxamide using Procedure H. Yield 13%. $^1$H NMR (CD$_3$OD) δ 8.49 (s, 1H), 8.25 (m, 1H), 7.77 (s, 1H), 7.73 (m, 2H), 7.64 (m, 1H), 7.53 (m, 2H), 4.53

(m, 1 H), 3.35 (m, 1H), 3.28 (m, 5H), 2.37 (m, 1H), 2.30 (m, 1H), 2.10 (m, 2H), 1.85 (m, 1 H); MS (EI) m/z 347 (M++1).

Example 65

N-((3S)-1-Azabicyclo[2.2.2]oct-3-yl)-6-(thiophen-2-yl)-1H-indazole-3-carboxamide hydroformate

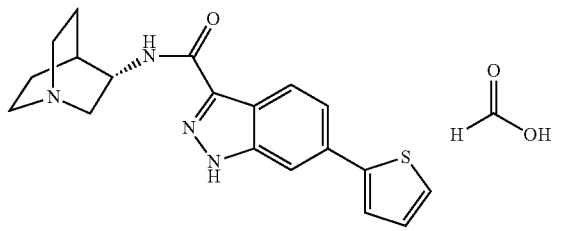

Prepared from N-((3S)-1-azabicyclo[2.2.2]oct-3-yl)-6-bromo-1H-indazole-3-carboxamide using Procedure H. Yield 22%. ¹H NMR (CD₃OD) δ 8.49 (s, 1H), 8.21 (m, 1H), 7.81 (s, 1H), 7.74 (m, 1H), 7.64 (m, 1H), 7.53 (m, 2H), 4.53 (m, 1 H), 3.35 (m, 1H), 3.28 (m, 5H), 2.37 (m, 1H), 2.30 (m, 1H), 2.10 (m, 2H), 1.85 (m, 1 H); MS (EI) m/z 353 (M++1).

Example 66

N-((3S)-1-Azabicyclo[2.2.2]oct-3-yl)-6-(thiophen-3-yl)-1H-indazole-3-carboxamide hydroformate

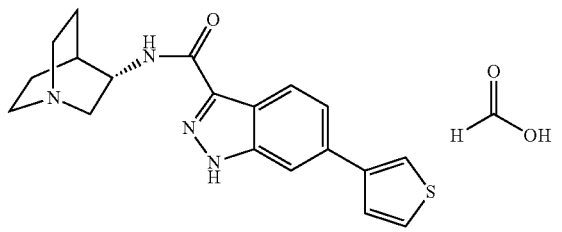

Prepared from N-((3S)-1-azabicyclo[2.2.2]oct-3-yl)-6-bromo-1H-indazole-3-carboxamide using Procedure H. Yield 17%. ¹H NMR (CD₃OD) δ 8.49 (s, 1H), 8.21 (m, 1H), 7.81 (s, 1H), 7.74 (m, 1H), 7.64 (m, 1H), 7.53 (m, 2H), 4.53 (m, 1 H), 3.35 (m, 1H), 3.28 (m, 5H), 2.37 (m, 1H), 2.30 (m, 1H), 2.10 (m, 2H), 1.85 (m, 1 H); MS (EI) m/z 353 (M++1).

Example 67

N-((3R)-1-Azabicyclo[2.2.2]oct-3-yl)-7-methoxybenzo[d]isothiazole-3-carboxamide

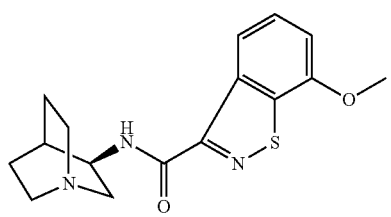

Prepared from 7-methoxybenzo[d]isothiazole-3-carboxylic acid using Procedure B. Yield 7%. LC/MS (EI) $t_R$ 4.00 min, m/z 318 (M++1).

Example 68

N-((3S)-1-Azabicyclo[2.2.2]oct-3-yl)-7-methoxybenzo[d]isothiazole-3-carboxamide

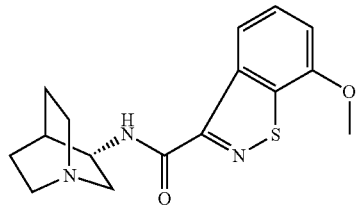

Prepared from 7-methoxybenzo[d]isothiazole-3-carboxylic acid using Procedure B. Yield 4%. LC/MS (EI) $t_R$ 3.76 min, m/z 318 (M++1).

Example 69

N-((3R)-1-Azabicyclo[2,2,2]oct-3-yl)-N-(1H-indazol-3-ylmethyl)amine

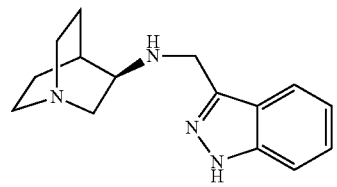

Prepared from 3-[(3R)-1-azabicyclo[2,2,]oct-3-yl]-1H-indazole-3-carboxyamide using Procedure F. Yield 50%. ¹H NMR (CD₃OD) δ 7.85 (m, 1H), 7.48 (d, J=8.4, 1H), 7.37 (dd, J=7.2, 8.4, 1H), 7.14 (dd, J=7.2, 8.4, 1H), 4.12 (m, 2H), 3.02 (m, 1H), 2.88 (m, 5H), 2.50 (m, 1H), 1.95 (m, 5H); MS (EI) m/z 257 (M++1).

Example 70

N-((3S)-1-Azabicyclo[2,2,2]oct-3-yl)-N-(1H-indazol-3-ylmethyl)amine

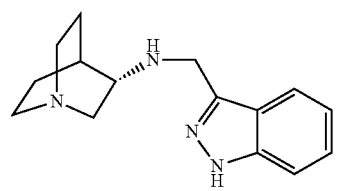

Prepared from 3-[(3S)-1-azabicyclo[2,2,]oct-3-yl]-1H-indazole-3-carboxyamide using Procedure F. Yield 50%. ¹H NMR (CD₃OD) δ 7.85 (m, 1H), 7.56 (m, 1H), 7.37 (m, 1H), 7.11 (m, 1H), 4.12 (m, 2H), 3.02 (m, 1H), 2.88 (m, 5H), 2.50 (m, 1 H), 1.95 (m, 5H); MS (EI) m/z 257 (M++1).

Example 71

N-((3R)-1-Azabicyclo[2.2.2]oct-3-yl)-1H-indazole-4-carboxamide

4-Bromo-1H-indazole

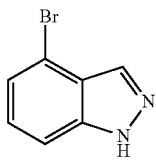

Prepared from 3-bromo-2-methylaniline using Procedure K. Yield 95%. $^1$H NMR (500 MHz, CDCl$_3$) δ 10.55 (bs, 1H); 8.12 (d, 1H), 7.46 (d, 1H), 7.34 (d, 1H), 7.25 (dd, 1H).

1H-Indazole-4-carboxylic acid

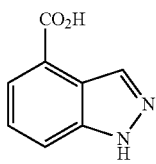

Prepared from 4-bromo-1H-indazole using Procedure L. Yield 55%. $^1$H NMR (500 MHz, DMSO-d$_6$) δ 13.27 (bs, 2H), 7.85 (d, 1H), 7.84 (d, 1H), 7.49 (t, 1 H); MS (EI) m/z 161 (M$^+$−1).

N-((3R)-1-Azabicyclo[2,2,2]oct-3-yl)-1H-indazole-4-carboxamide

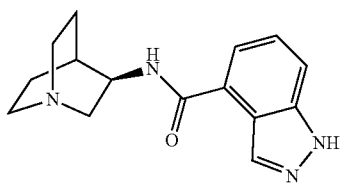

Prepared from 1H-indazole-4-carboxylic acid using Procedure A. Yield 50%. $^1$H NMR (CD$_3$OD) δ 8.38 (d, J=0.9, 1H), 7.74 (d, J=8.4, 1H), 7.62 (d, J=6.9, 1H), 7.46 (dd, J=6.9, 8.4, 1H), 4.39 (m, 1H), 3.62 (m, 1H), 3.12 (m, 5H), 1.95 (m, 5H); MS (EI) m/z 271 (M$^+$+1).

Example 72

N-((3S)-1-Azabicyclo[2.2.2]oct-3-yl)-1H-indazole-4-carboxamide

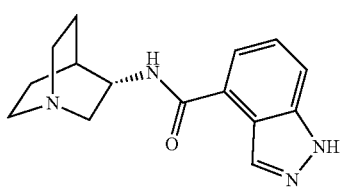

Prepared from 1H-indazole-4-carboxylic acid using Procedure A. Yield 50%. $^1$H NMR (CD$_3$OD) δ 8.40 (d, J=0.6, 1H), 7.75 (d, J=8.4, 1H), 7.67 (d, J=6.6, 1H), 7.45 (dd, J=6.6, 8.4, 1H), 4.49 (m, 1H), 3.77 (m, 1H), 3.30 (m, 5H), 1.95 (m, 5H); MS (EI) m/z 271 (M$^+$+1).

Example 73

N-(1H-Indazol-4-yl)-1-azabicyclo[2,2,2]oct-3-ylcarboxamide

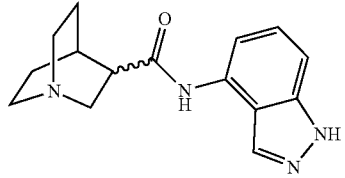

Prepared from indazole-4-ylamine using Procedure E. Yield 30%. $^1$H NMR (CD$_3$OD$_3$) δ 8.20 (s, 1H), 7.55 (m, 1H), 7.36 (m, 2H), 3.92 (m, 1H), 3.46 (m, 5H), 2.56 (m, 1H), 2.06 (m, 5H); MS (EI) m/z 271 (M$^+$+1).

Example 74

N-(1-Azabicyclo[2,2,2]oct-3-yl)-N-(1H-indazol-4-ylmethyl)amine

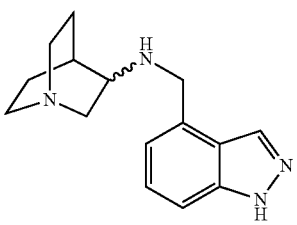

Prepared from indazol-4-carboxaldehyde using Procedure G. Yield 50%. $^1$H NMR (CD$_3$OD) δ 8.27 (s, 1H), 7.48 (m, 1H), 7.37 (m, 1H), 7.17 (m, 1H), 4.18 (m, 2H), 3.52 (m, 1H), 3.30 (m, 5H), 3.00 (m, 1H), 1.95 (m, 5H); MS (EI) m/z 257 (M$^+$+1).

Example 75

N-((3R)-1-Azabicyclo[2,2,2]oct-3-yl)benzothiazole-5-carboxamide hydrochloride 1,3-Benzothiazole-5-carboxylic acid

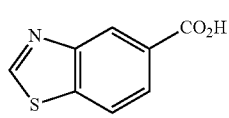

Prepared from 4-chloro-3-nitrobenzoic acid using Procedure O. Yield 4.30 g (94%) of pure product. $^1$H NMR (500 MHz, DMSO-d$_6$) δ 13.2 (bs, 1H), 9.52 (s, 1H), 8.60 (d, 1H), 8.30 (d, 1H), 8.05 (dd, 1H); MS (ACPI) m/z 178 (M$^+$−1).

N-((3R)-1-Azabicyclo[2,2,2]oct-3-yl)benzothiazole-5-carboxamide hydrochloride

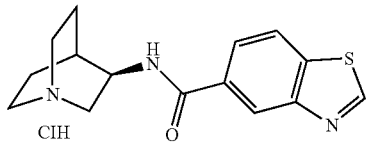

Prepared from 1,3-benzothiazole-5-carboxalic acid using Procedure C. Yield 92%. $^1$H NMR (500 MHz, CD$_3$OD) δ 9.89 (s, 1H), 8.68 (s, 1H), 8.30 (d, J=8.5, 1H), 8.14 (d, J=8.5, 1H), 4.53 (m, 1H), 3.87 (m, 1H), 3.58 (m, 1H), 3.43 (m, 4H), 2.42 (m, 1 H), 2.34 (m, 1H), 2.13 (m, 2H), 1.97 (m, 1H); MS (APCI) m/z 288 (M$^+$+1); m.p. 170-180° C.

Example 76

N-((3S)-1-Azabicyclo[2,2,2]oct-3-yl)benzothiazole-5-carboxamide hydrochloride

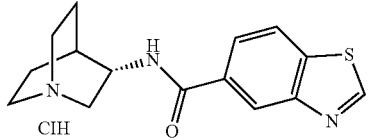

Prepared from 1,3-benzothiazole-5-carboxalic acid using Procedure C. Yield 96%. $^1$H NMR (500 MHz, CD$_3$OD) δ 9.77 (s, 1H), 8.66 (s, 1H), 8.27 (d, J=8.5, 1H), 8.12 (d, J=8.5, 1H), 4.53 (m, 1H), 3.87 (m, 1H), 3.56 (m, 1H), 3.40 (m, 4H), 2.42 (m, 1 H), 2.33 (m, 1H), 2.13 (m, 2H), 1.97 (m, 1H); MS (APCI) m/z 288 (M$^+$+1); m.p. 166-176° C.

Example 77

N-((3R)-1-Azabicyclo[2.2.2]oct-3-yl)-1H-indazole-5-carboxamide

5-Bromo-1H-indazole

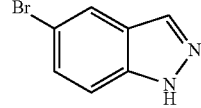

Prepared from 4-bromo-2-methylaniline using Procedure K. Yield 88%. $^1$H NMR (500 MHz, CDCl$_3$) δ 10.4 (bs, 1H), 8.04 (s, 1H), 7.92 (s, 1H), 7.47 (dd, J=1.0, 1 H), 7.39 (d, J=8.5, 1H); MS (EI) m/z 197, 199 (M$^+$+1).

1H-Indazole-5-carboxylic acid

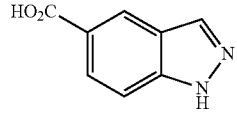

Prepared from 5-bromo-1H-indazole using Procedure L. Yield 54%. $^1$H NMR (500 MHz, DMSO-d$_6$) δ 13.18 (bs, 2H), 8.50 (t, 1H), 8.27 (d, 1H), 7.95 (dd, 1H), 7.63 (dt, 1H); $^{13}$C NMR (125 MHz, DMSO-d$_6$) δ 167.71, 141.64, 135.20, 126.61, 123.79, 123.12, 122.60, 110.04; MS (APCI) m/z 161 (M$^+$−1)

N-((3R)-1-Azabicyclo[2.2.2]oct-3-yl)-1H-indazole-5-carboxamide

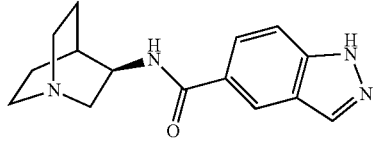

Prepared from 1H-indazole-5-carboxylic acid using Procedure A. Yield 50%. $^1$H NMR (CD$_3$OD) δ 8.34 (s, 1H), 8.15 (s, 1H), 7.88 (d, J=8.7, 1H), 7.59 (d, J=8.7, 1 H), 4.23 (m, 1H), 3.43 (m, 1H), 2.97 (m, 5H), 1.92 (m, 5H); MS (EI) m/z 271 (M$^+$+1).

Example 78

N-((3S)-1-Azabicyclo[2.2.2]oct-3-yl)-1H-indazole-5-carboxamide

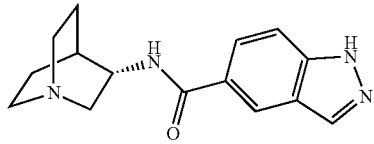

Prepared from 1H-indazole-5-carboxylic acid using Procedure A. Yield 50%. $^1$H NMR (CD$_3$OD) δ 8.34 (s, 1H), 8.16 (s, 1H), 7.90 (d, J=9.0, 1H), 7.60 (d, J=9.0, 1 H), 4.30 (m, 1H), 3.54 (m, 1H), 3.05 (m, 5H), 1.92 (m, 5H); MS (EI) m/z 271 (M$^+$+1).

Example 79

N-(1H-Indazol-5-yl)-1-azabicyclo[2.2.2]oct-3-ylcarboxamide

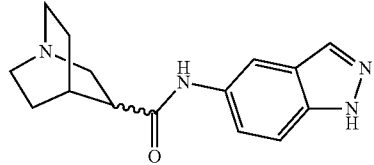

Prepared from 1H-indazol-5-ylamine using Procedure E. Yield 30%. $^1$H NMR (CD$_3$OD) δ 8.04 (m, 2H), 7.45 (m, 2H), 3.40 (m, 1H), 2.90 (m, 5H), 2.16 (m, 1H), 1.90 (m, 5H); MS (EI) m/z 271 (M$^+$+1).

Example 80

N-(1-Azabicyclo[2,2,2]oct-3-yl)benzothiazole-6-carboxamide

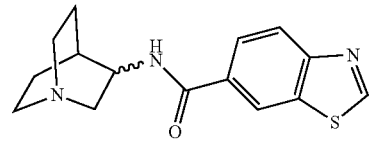

Prepared from benzothiazole-6-carboxylic acid using Procedure A. Yield 60%. ¹H NMR (CDCl₃) δ 9.14 (s, 1H), 8.50 (m, 1H), 8.20 (m, 1H), 7.90 (m, 1H), 6.47 (m, 1H, NH), 4.25 (m, 1H), 3.45 (m, 2H), 2.78 (m, 4H), 1.90 (m, 5H); MS (EI) m/z 288 (M⁺+1).

Example 82

N-((3R)-1-Azabicyclo[2,2,2]oct-3-yl)benzothiazole-6-carboxamide hydrochloride

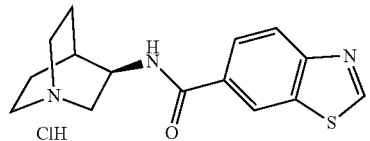

Prepared from 1,3-benzothiazole-6-carboxylic acid using Procedure C. Yield 85%. ¹H NMR (500 MHz, CD₃OD) δ 9.71 (s, 1H), 8.74 (t, J=1.0, 1H), 8.16 (m, 2H), 4.51 (m, 1H), 3.85 (m, 1H), 3.53 (m, 1H), 3.37 (m, 6H), 2.39 (m, 1H), 2.30 (m, 1H), 2.11 (m, 2H), 1.95 (m, 1H); MS (APCI) m/z 288 (M⁺+1); m.p. 285° C. (dec.).

Example 82

N-((3S)-1-Azabicyclo[2,2,2]oct-3-yl)benzothiazole-6-carboxamide hydrochloride

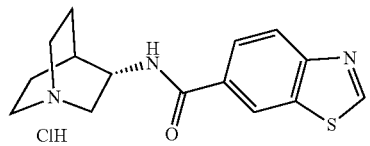

Prepared from 1,3-benzothiazole-6-carboxylic acid using Procedure C. Yield 100%. ¹H NMR (500 MHz, CD₃OD) δ 9.75 (s, 1H), 8.75 (t, J=1.0, 1H), 8.17 (m, 2H), 4.50 (m, 1H) 3.85 (m, 1H), 3.51 (m, 1H), 3.37 (m, 7H), 2.40 (m, 1H), 2.31 (m, 1H), 2.11 (m, 2H), 1.95 (m, 1H); MS (APCI) m/z 288 (M⁺+1); m.p. dec. 287° C.

Example 83

N-((3R)-1-Azabicyclo[2,2,2]oct-3-yl)-2-(pyrrol-1-yl)benzothiazole-6-carboxamide hydroformate

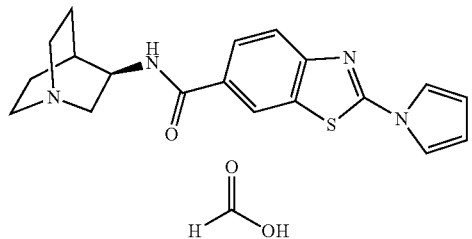

Prepared from 2-(pyrrol-1-yl)1,3-benzothiazole-6-carboxylic acid using Procedure A. Yield 75%. ¹H NMR (CD₃OD) δ 8.45 (s, 1H), 7.99 (d, J=8.4, 1H), 7.90 (d, J=8.4, 1H), 7.56 (d, J=2.1, 1H), 6.44 (d, J=2.1, 1H), 4.47 (m, 1H), 3.87 (m, 1H), 3.40 (m, 4H), 2.39 (m, 1H), 2.28 (m, 1H), 2.11 (m, 2H), 1.96 (m, 1H); MS (EI) m/z 353 (M⁺+1).

Example 84

N-(Benzothiazol-6-yl)-1-azabicyclo[2,2,2]oct-3-ylcarboxamide

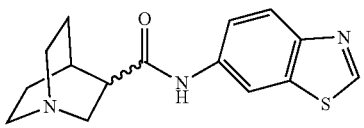

Prepared from benzothiazole-6-yl amine using Procedure E. Yield 30%. ¹H NMR (CD₃OD₃) δ 9.11 (s, 1H), 8.51 (s, 1H), 7.95 (d, J=9.0, 1H), 7.62 (d, J=9.0, 1H), 3.44 (m, 1H), 2.88 (m, 6H), 2.13 (m, 1H), 1.74 (m, 3H), 1.46 (m, 1H); MS (EI) m/z 288 (M⁺+1).

Example 85

N-((3R)-1-Azabicyclo[2.2.2]oct-3-yl)-1H-indazole-6-carboxamide

6-Bromo-1H-indazole

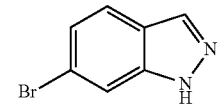

Prepared from 5-bromo-2-methylaniline using Procedure K. Yield 88%. ¹H NMR (400 MHz, CDCl₃) δ 13.20 (bs, 1H), 8.10 (d, 1H), 7.76 (m, 1H), 7.72 (dd, 1H), 7.24 (dd, 1H).

1H-Indazole-6-carboxylic acid

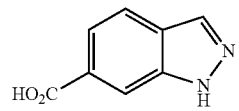

Prepared from 6-bromo-1H-indazole using Procedure L. Yield 46%. ¹H NMR (500 MHz, DMSO-d₆) δ 13.24 (bs, 2H), 8.20 (d, 1H), 8.19 (m, 1H), 7.87 (dd, 1H), 7.70 (dd, 1H); ¹³C NMR (125 MHz, DMSO-d₆) δ 167.53, 139.32, 133.43, 128.23, 125.08, 120.47, 120.45, 112.10; MS (APCI) m/z 161 (M⁺−1).

N-((3R)-1-Azabicyclo[2.2.2]oct-3-yl)-1H-indazole-6-carboxamide

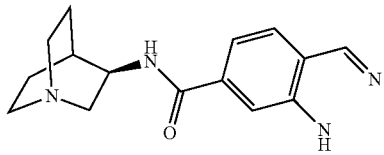

Prepared from 1H-indazole-6-carboxylic acid using Procedure A. Yield 50%. $^1$H NMR (CD$_3$OD) δ 8.11 (s, 1H), 8.06 (s, 1H), 7.83 (d, J=8.4, 1H), 7.60 (d, J=8.4, 1 H), 4.24 (m, 1H), 3.35 (m, 1H), 2.97 (m, 5H), 1.92 (m, 5H); MS (EI) m/z 271 (M$^+$+1).

Example 86

N-((3S)-1-Azabicyclo[2.2.2]oct-3-yl)-1H-indazole-6-carboxamide

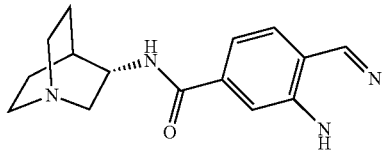

Prepared from 1H-indazole-6-carboxylic acid using Procedure A. Yield 50%. $^1$H NMR (CD$_3$OD) δ 8.11 (s, 1H), 8.06 (s, 1H), 7.84 (d, J=7.8, 1H), 7.60 (d, J=7.8, 1 H), 4.22 (m, 1H), 3.41 (m, 1H), 2.96 (m, 5H), 1.92 (m, 5H); MS (EI) m/z 271 (M$^+$+1).

Example 87

N-((3R)-1-Azabicyclo[2.2.2]oct-3-yl)-3-(thiophen-3-yl)-1H-indazole-6-carboxamide hydroformate

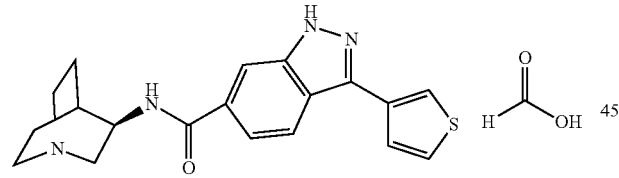

Prepared from N-((3R)-1-azabicyclo[2.2.2]oct-3-yl)-3-(iodo)-1H-indazole-6-carboxamide using Procedure H. Yield 28%. LC/MS (EI) t$_R$ 4.17 min, m/z 353 (M$^+$+1).

Example 88

N-(1H-Indazol-6-yl)-1-azabicyclo[2,2,2]oct-3-ylcarboxamide

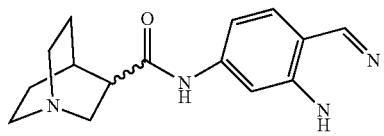

Prepared from indazole-6-yl amine using Procedure E. Yield 30%. $^1$H NMR (CD$_3$OD$_3$) δ 8.18 (s, 1H), 7.92 (s, 1H), 7.62 (m, 1H), 7.62 (m, 1H), 3.64 (m, 1H), 3.30 (m, 5H), 2.40 (m, 1H), 1.90 (m, 5H); MS (EI) m/z 271 (M$^+$+1).

Example 89

N-((3R)-1-Azabicyclo[2,2,2]oct-3-yl)benzothiazole-7-carboxamide hydrochloride 1,3-Benzothiazole-7-carboxylic acid

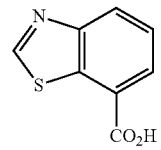

Prepared from ethyl 3-aminobenzoate using Procedure P. Yield 2.75 g (91%). $^1$H NMR (500 MHz, DMSO-d$_6$) δ 7.71 (t, J=7.5, 1H), 8.15 (d, J=7, 1H), 8.38 (d, J=8, 1 H), 9.51 (s, 1H), 13.74 (bs, 1H); MS (APCI) m/z 178 (M$^+$–1).

N-((3R)-1-Azabicyclo[2,2,2]oct-3-yl)benzothiazole-7-carboxamide hydrochloride

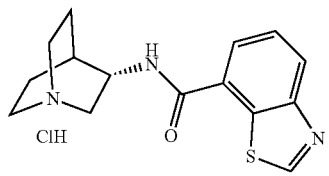

Prepared from 1,3-benzothiazole-7-carboxylic acid using Procedure C. $^1$H NMR (500 MHz, DMSO-d$_6$) δ 1.71-1.75 (m, 1H), 1.92-1.96 (m, 2H), 2.18-2.26 (m, 2H), 3.17-3.25 (m, 3H), 3.45-3.66 (m, 3H), 4.44 (d, J=6, 1H), 7.69 (t, J=8, 1H), 8.28 (d, J=8, 1H), 8.54 (d, J=8, 1H), 9.37 (d, J=6.5, 1H), 9.49 (s, 1H), 10.88 (bs, 1 H); MS (EI) m/z 288 (M$^+$+1).

Example 90

N-((3S)-1-Azabicyclo[2,2,2]oct-3-yl)benzothiazole-7-carboxamide hydrochloride

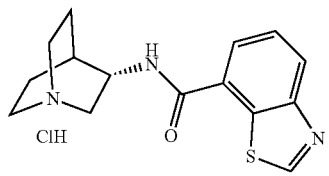

Prepared from 1,3-benzothiazole-7-carboxylic acid using Procedure C. $^1$H NMR (500 MHz, DMSO-d$_6$) δ 1.71-1.75 (m, 1H), 1.92-1.95 (m, 2H), 2.17-2.26 (m, 2H), 3.17-3.24 (m, 3H), 3.44-3.55 (m, 2H), 3.60-3.65 (m, 1H), 4.44 (d, J=6, 1H), 7.69 (t, J=8, 1H), 8.29 (d, J=8, 1H), 8.53 (d, J=8, 1H), 9.36 (d, J=6.5, 1H), 9.48 (s, 1H), 10.87 (bs, 2H); MS (EI) m/z 288 (M$^+$+1).

Example 91

N-((3R)-1-Azabicyclo[2.2.2]oct-3-yl)-1H-indazole-7-carboxamide

1H-Indazole-7-carboxylic acid

Prepared from 2-amino-3-methylbenzoic acid using procedure M. Yield 5.86 g (94%). $^1$H NMR (500 MHz, DMSO-$d_6$) δ 13.20 (bs, 2H), 8.23 (s, 1H), 8.08 (dd, 1H), 8.00 (dd, 1H), 7.25 (dd, 1H); MS (APCI) m/z 161 (M$^+$−1).

N-((3R)-1-Azabicyclo[2.2.2]oct-3-yl)-1H-indazole-7-carboxamide

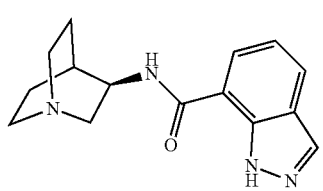

Prepared from 1H-indazole-7-carboxylic acid using Procedure A. Yield 50%. $^1$H NMR (CD$_3$OD) δ 8.15 (s, 1H), 7.97 (dd, J=7.5, 7.8, 2H), 7.21 (dd, J=7.8, 7.5, 1H), 4.30 (m, 1H), 3.43 (m, 1H), 3.06 (m, 1H), 2.85 (m, 4H), 1.95 (m, 5H); MS (EI) m/z 271 (M$^+$+1).

Example 92

N-((3R)-1-Azabicyclo[2.2.2]oct-3-yl)-1H-indazole-7-carboxamide hydrochloride

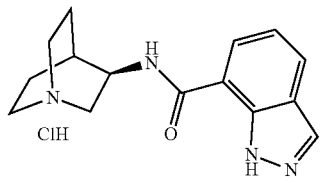

Prepared from 1H-indazole-7-carboxylic acid using Procedure C. Yield 71%. $^1$H NMR (500 MHz, CD$_3$OD) δ 8.61 (s, 1H), 8.32 (d, J=7.5, 1H), 8.14 (d, J=8.0, 1H), 7.44 (dd, J=8.0, 7.5, 1H), 4.59 (m, 1H), 3.89 (m, 1H), 3.55 (m, 1H), 3.40 (m, 4H), 2.44 (m, 1H), 2.30 (m, 1H), 2.12 (m, 2H), 1.96 (m, 1H); MS (APCI) m/z 271 (M$^+$+1).

Example 93

N-((3S)-1-Azabicyclo[2.2.2]oct-3-yl)-1H-indazole-7-carboxamide

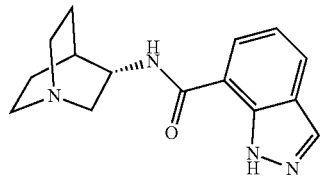

Prepared from 1H-indazole-7-carboxylic acid using Procedure A. Yield 50%. $^1$H NMR (CD$_3$OD) δ 8.16 (s, 1H), 8.05 (dd, J=6.6, 0.9, 1H), 7.21 (dd, J=0.9, 7.5, 1H), 7.21 (dd, J=7.5, 6.6, 1H), 4.48 (m, 1H), 3.62 (m, 1H), 3.20 (m, 1H), 3.10 (m, 4H), 1.95 (m, 5H); MS (EI) m/z 271 (M$^+$+1).

Example 94

N-((3S)-1-Azabicyclo[2.2.2]oct-3-yl)-1H-indazole-7-carboxamide hydrochloride

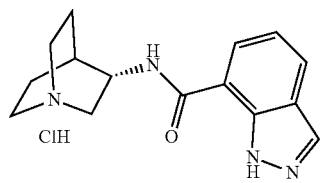

Prepared from 1H-indazole-7-carboxylic acid using Procedure C. Yield 71%. $^1$H NMR (500 MHz, CD$_3$OD) δ 8.61 (s, 1H), 8.32 (d, J=7.5, 1H), 8.14 (d, J=8.0, 1H), 7.44 (t, J=8.0, 1H), 4.59 (m, 1H), 3.89 (m, 1H), 3.55 (m, 1H), 3.40 (m, 4H), 2.44 (m, 1 H), 2.30 (m, 1H), 2.12 (m, 2H), 1.96 (m, 1H); MS (APCI) m/z 271 (M$^+$+1); m.p. 180-188° C.

Example 95

[$^3$H] MLA Binding

Materials:
Rat Brain: Pel-Freez Biologicals, CAT No. 56004-2
Protease inhibitor cocktail tablet: Roche, CAT No. 1697498

Membrane Preparation

Rat brains in 20 vol (w/v) of ice-cold 0.32 M sucrose with protease inhibitors (one tablet per 50 ml,) were homogenized with a polytron for 10 sec at setting 11, then centrifuged 10 min at 1000 g, 4° C. The supernatant was centrifuged again for 20 mM at 20,000 g, 4° C. The pellets were resuspended in binding buffer (200 mM TRIS-HCl, 20 mM HEPES, pH 7.5, 144 mM NaCl, 1.5 mM KCl, 1 mM MgSO$_4$, 2 mM CaCl$_2$, 0.1% (w/v) BSA) and stored membrane prep at −80° C.

For saturation assay, the 200 µl assay mixture in binding buffer contains 200 µg of membrane protein, 0.2 to 44 nM of [$^3$H] MLA. The nonspecific binding was defined using 1 µM MLA. Competition assay was carried out with 2 nM [$^3$H] MLA and a desirable range of compounds. The assay mixture was incubated at 22° C. for 2 hours, then harvested with GF/B filter presoaked with 0.3% PEI in binding buffer using Tomtec harvester. The filter was washed three time with binding buffer and the radioactivity was counted with Trilux.

The preceding examples can be repeated with similar success by substituting the generically or specifically described reactants and/or operating conditions of this invention for those used in the preceding examples.

While the invention has been illustrated with respect to the production and of particular compounds, it is apparent that variations and modifications of the invention can be made without departing from the spirit or scope of the invention.

We claim:

1. A compound of Formulas I, II, III, or IV:

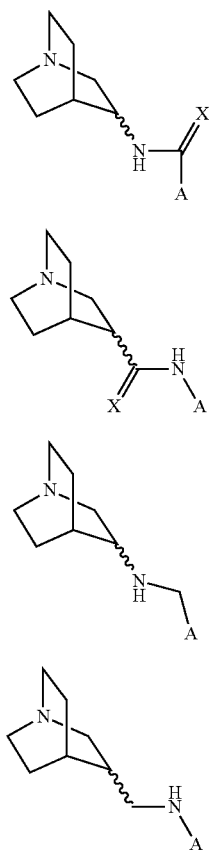

wherein

A is a benzothiazolyl group according to subformula (b)

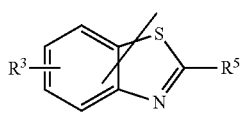

X is O or S;

$R^3$ is H, F, Cl, Br, I, OH, CN, nitro, $NH_2$, alkyl having 1 to 4 carbon atoms, fluorinated alkyl having 1 to 4 carbon atoms, cycloalkyl having 3 to 7 carbon atoms, cycloalkylalkyl having 4 to 7 carbon atoms, alkoxy having 1 to 4 carbon atoms, cycloalkoxy having 3 to 7 carbon atoms, cycloalkylalkoxy having 4 to 7 carbon atoms, alkylthio having 1 to 4 carbon atoms, fluorinated alkoxy having 1 to 4 carbon atoms, hydroxyalkyl having 1 to 4 carbon atoms, hydroxyalkoxy having 2 to 4 carbon atoms, monoalkylamino having 1 to 4 carbon atoms, dialkylamino wherein each alkyl group independently has 1 to 4 carbon atoms, Ar or Het;

$R^5$ is H, F, Cl, Br, I, OH, CN, nitro, $NH_2$, alkyl having 1 to 4 carbon atoms, fluorinated alkyl having 1 to 4 carbon atoms, cycloalkyl having 3 to 7 carbon atoms, cycloalkylalkyl having 4 to 7 carbon atoms, alkoxy having 1 to 4 carbon atoms, cycloalkoxy having 3 to 7 carbon atoms, cycloalkylalkoxy having 4 to 7 carbon atoms, alkylthio having 1 to 4 carbon atoms, fluorinated alkoxy having 1 to 4 carbon atoms, hydroxyalkyl having 1 to 4 carbon atoms, hydroxyalkoxy having 2 to 4 carbon atoms, monoalkylamino having 1 to 4 carbon atoms, dialkylamino wherein each alkyl group independently has 1 to 4 carbon atoms, Ar or Het;

Ar is an aryl group containing 6 to 10 carbon atoms which is unsubstituted or substituted one or more times by alkyl having 1 to 8 carbon atoms, alkoxy having 1 to 8 carbon atoms, halogen, dialkylamino wherein the alkyl portions each have 1 to 8 carbon atoms, amino, cyano, hydroxyl, nitro, halogenated alkyl having 1 to 8 carbon atoms, halogenated alkoxy having 1 to 8 carbon atoms, hydroxyalkyl having 1 to 8 carbon atoms, hydroxyalkoxy having 2 to 8 carbon atoms, alkenyloxy having 3 to 8 carbon atoms, alkylthio having 1 to 8 carbon atoms, alkylsulphinyl having 1 to 8 carbon atoms, alkylsulphonyl having 1 to 8 carbon atoms, monoalkylamino having 1 to 8 carbon atoms, cycloalkylamino wherein the cycloalkyl group has 3 to 7 carbon atoms and is optionally substituted, aryloxy wherein the aryl portion contains 6 to 10 carbon atoms and is optionally substituted, arylthio wherein the aryl portion contains 6 to 10 carbon atoms and is optionally substituted, cycloalkyloxy wherein the cycloalkyl group has 3 to 7 carbon atoms and is optionally substituted, sulfo, sulfonylamino, acylamido, acyloxy or combinations thereof; and Het is a heterocyclic group, which is fully saturated, partially saturated or fully unsaturated, having 5 to 10 ring atoms in which at least 1 ring atom is a N, O or S atom, which is unsubstituted or substituted one or more times by halogen, aryl having 6 to 10 carbon atoms and is optionally substituted, alkyl having 1 to 8 carbon atoms, alkoxy having 1 to 8 carbon atoms, cyano, trifluoromethyl, nitro, oxo, amino, monoalkylamino having 1 to 8 carbon atoms, dialkylamino wherein each alkyl group has 1 to 8 carbon atoms, or combinations thereof; or a pharmaceutically acceptable salt thereof, wherein if the compound exhibits chirality it can be in the form of a mixture of enantiomers such as a racemate or a mixture of diastereomers, or can be in the form of a single enantiomer or a single diastereomer wherein when said compound is of Formula I the benzothiazolyl group of group A is attached via its 4 or 7 position.

2. A compound according to claim 1, wherein said compound is of formulas If or Ii:

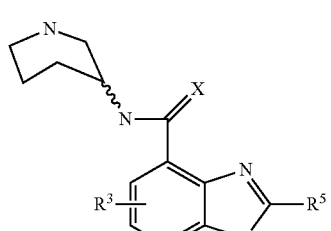
(If)
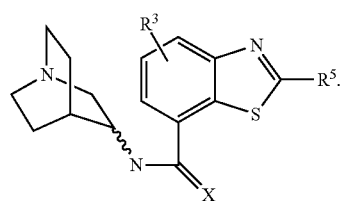
(Ii)
3. A compound according to claim 1, wherein said compound is of formulas IIf to IIi:
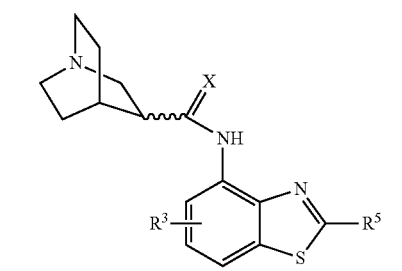
(IIf)
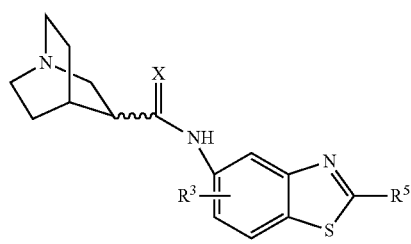
(IIg)
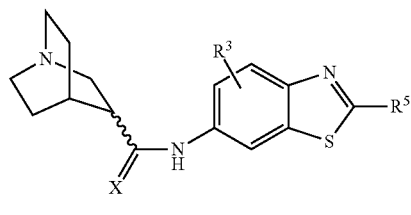
(IIh)
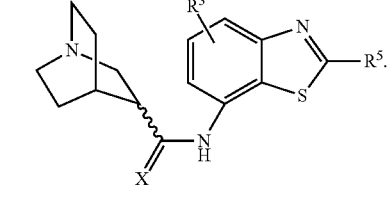
(IIi)
4. A compound according to claim 1, wherein said compound is of formulas IIIf to IIIi:
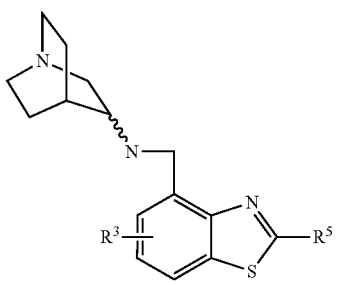
(IIIf)
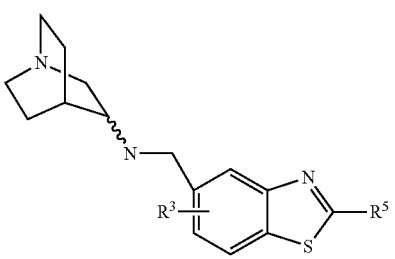
(IIIg)
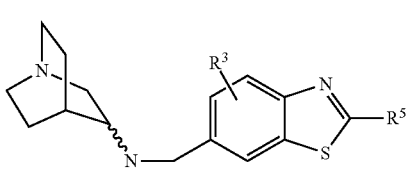
(IIIh)
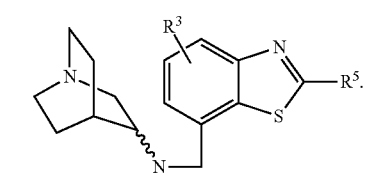
(IIIi)
5. A compound according to claim 1, wherein said compound is of formulas IVf to IVi:
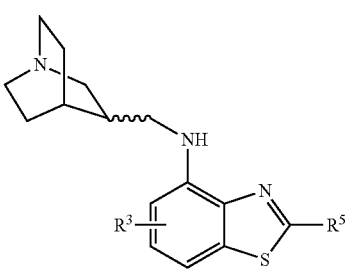
(IVf)
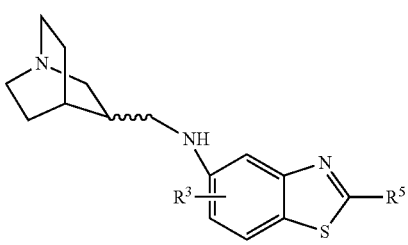
(IVg)

-continued (IVh)
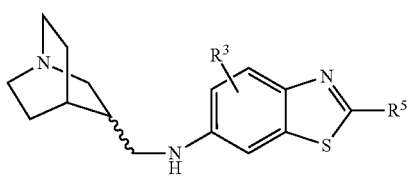

(IVi)
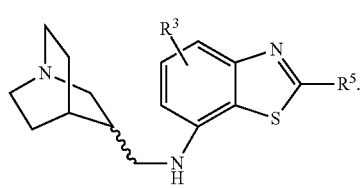

6. A compound according to Formulae I'-IV':

(I')
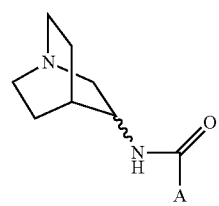

(II')
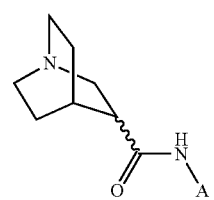

(III')
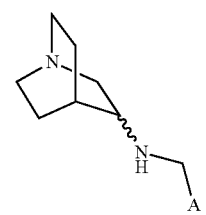

(IV')
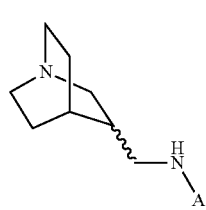

(I')
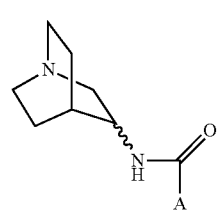

-continued (II')
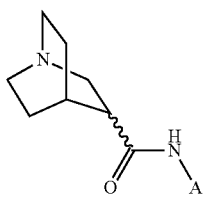

(III')
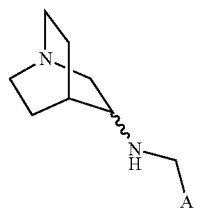

(IV')
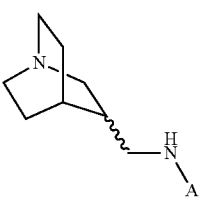

wherein
A is a benzothiazolyl according to subformula (b), (b)
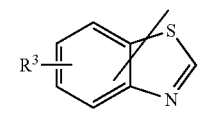

$R^3$ is H, F, Cl, Br, I, OH, CN, nitro, $NH_2$, alkyl having 1 to 4 carbon atoms, fluorinated alkyl having 1 to 4 carbon atoms, cycloalkyl having 3 to 7 carbon atoms, cycloalkylalkyl having 4 to 7 carbon atoms, alkoxy having 1 to 4 carbon atoms, cycloalkoxy having 3 to 7 carbon atoms, alkylthio having 1 to 4 carbon atoms, fluorinated alkoxy having 1 to 4 carbon atoms, hydroxyalkyl having 1 to 4 carbon atoms, hydroxyalkoxy having 2 to 4 carbon atoms, monoalkylamino having 1 to 4 carbon atoms, dialkylamino wherein each alkyl group independently has 1 to 4 carbon atoms, Ar or Het;

Ar is an aryl group containing 6 to 10 carbon atoms which is unsubstituted or substituted one or more times by alkyl having 1 to 8 C atoms, alkoxy having 1 to 8 C atoms, halogen, dialkylamino wherein the alkyl portions each have 1 to 8 C atoms, amino, cyano, hydroxyl, nitro, halogenated alkyl having 1 to 8 C atoms, halogenated alkoxy having 1 to 8 C atoms, hydroxyalkyl having 1 to 8 C atoms, hydroxyalkoxy having 2 to 8 C atoms, alkenyloxy having 3 to 8 C atoms, alkylthio having 1 to 8 C atoms, alkylsulphinyl having 1 to 8 C atoms, alkylsulphonyl having 1 to 8 C atoms, monoalkylamino having 1 to 8 C atoms, cycloalkylamino wherein the cycloalkyl group has 3 to 7 C atoms and is optionally substituted, aryloxy wherein the aryl portion contains 6 to 10 carbon atoms and is optionally substituted, arylthio wherein the aryl portion contains 6 to 10 carbon atoms and is optionally substituted, cycloalkyloxy wherein the cycloalkyl group has 3 to 7 C atoms and is optionally substituted, sulfo, sulfonylamino, acylamido, acyloxy or combinations thereof; and Het is a heterocyclic group, which is fully saturated, partially saturated or fully unsaturated, having 5 to 10 ring atoms in which at least 1 ring atom is a N, O or S atom, which is unsubstituted or substituted one or more times by halogen, aryl having 6 to 10 carbon atoms and is optionally substituted, alkyl having 1 to 8 C atoms, alkoxy having 1 to 8 C atoms, cyano, trifluoromethyl, nitro, oxo, amino, monoalkylamino having 1 to 8 C atoms, dialkylamino wherein each alkyl group has 1 to 8 C atoms, or combinations thereof; or a pharmaceutically acceptable salt thereof.

7. A compound according to claim 6, wherein said compound is of formula I' f or I'i:

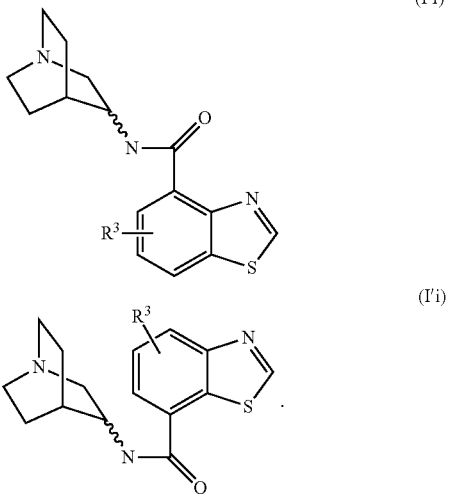

8. A compound according to claim 1, wherein $R^3$ is H, F, Cl, Br, 2-thiophenyl, 3-thiophenyl, 3-furyl, or phenyl.

9. A compound according to claim 1, wherein, and $R^3$ is H, F, Cl, Br, methyl, methoxy, or amino.

10. A compound according to claim 1, wherein $R^5$ is H.

11. A compound according to claim 1, wherein said compound is selected from:
N-((3R)-1-Azabicyclo[2,2,2]oct-3-yl)benzothiazole-7-carboxamide hydrochloride,
N-((3S)-1-Azabicyclo[2,2,2]oct-3-yl)benzothiazole-7-carboxamide hydrochloride,
Benzothiazole-4-carboxamide, N-1-aza-bicyclo[2,2,2]oct-3-yl,
(R) Benzothiazole-4-carboxamide, N-1-aza-bicyclo[2,2,2]oct-3-yl,
(S) Benzothiazole-4-carboxamide, N-1-aza-bicyclo[2,2,2]oct-3-yl,
1-Aza-bicyclo[2,2,2]oct-3-ylcarboxamide, benzothiazol-4-yl,
(S) 1-Aza-bicyclo[2,2,2]oct-3-ylcarboxamide, benzothiazol-4-yl,
(R) 1-Aza-bicyclo[2,2,2]oct-3-ylcarboxamide, benzothiazol-4-yl,
1-Aza-bicyclo[2,2,2]oct-3-ylcarboxamide, benzothiazol-7-yl,
(S) 1-Aza-bicyclo[2,2,2]oct-3-ylcarboxamide, benzothiazol-7-yl,
(R) 1-Aza-bicyclo[2,2,2]oct-3-ylcarboxamide, benzothiazol-7-yl,
(1-Aza-bicyclo[2,2,2]oct-3-yl)-(benzothiazol-4-ylmethyl)-amine,
(S) (1-Aza-bicyclo[2,2,2]oct-3-yl)-(benzothiazol-4-ylmethyl)-amine,
(R) (1-Aza-bicyclo[2,2,2]oct-3-yl)-(benzothiazol-4-ylmethyl)-amine,
(1-Aza-bicyclo[2,2,2]oct-3-yl)-(benzothiazol-5-ylmethyl)-amine,
(S) (1-Aza-bicyclo[2,2,2]oct-3-yl)-(benzothiazol-5-ylmethyl)-amine,
(R) (1-Aza-bicyclo[2,2,2]oct-3-yl)-(benzothiazol-5-ylmethyl)-amine,
(1-Aza-bicyclo[2,2,2]oct-3-yl)-(benzothiazol-6-ylmethyl)-amine,
(S) (1-Aza-bicyclo[2,2,2]oct-3-yl)-(benzothiazol-6-ylmethyl)-amine,
(R) (1-Aza-bicyclo[2,2,2]oct-3-yl)-(benzothiazol-6-ylmethyl)-amine,
(1-Aza-bicyclo[2,2,2]oct-3-yl)-(benzothiazol-7-ylmethyl)-amine,
(S) (1-Aza-bicyclo[2,2,2]oct-3-yl)-(benzothiazol-7-ylmethyl)-amine,
(R) (1-Aza-bicyclo[2,2,2]oct-3-yl)-(benzothiazol-7-ylmethyl)-amine,
(1-Aza-bicyclo[2,2,2]oct-3-ylmethyl)-(benzothiazol-4-yl)-amine,
(S) (1-Aza-bicyclo[2,2,2]oct-3-ylmethyl)-(benzothiazol-4-yl)-amine,
(R) (1-Aza-bicyclo[2,2,2]oct-3-ylmethyl)-(benzothiazol-4-yl)-amine,
(1-Aza-bicyclo[2,2,2]oct-3-ylmethyl)-(benzothiazol-5-yl)-amine,
(S) (1-Aza-bicyclo[2,2,2]oct-3-ylmethyl)-(benzothiazol-5-yl)-amine,
(R) (1-Aza-bicyclo[2,2,2]oct-3-ylmethyl)-(benzothiazol-5-yl)-amine,
(1-Aza-bicyclo[2,2,2]oct-3-ylmethyl)-(benzothiazol-6-yl)-amine,
(S) (1-Aza-bicyclo[2,2,2]oct-3-ylmethyl)-(benzothiazol-6-yl)-amine,
(R) (1-Aza-bicyclo[2,2,2]oct-3-ylmethyl)-(benzothiazol-6-yl)-amine,
(1-Aza-bicyclo[2,2,2]oct-3-ylmethyl)-(benzothiazol-7-yl)-amine,
(S) (1-Aza-bicyclo[2,2,2]oct-3-ylmethyl)-(benzothiazol-7-yl)-amine,
(R) (1-Aza-bicyclo[2,2,2]oct-3-ylmethyl)-(benzothiazol-7-yl)-amine,
and pharmaceutically acceptable salts thereof.

12. A pharmaceutical composition comprising a compound according to claim 1 and a pharmaceutically acceptable carrier.

13. A compound according to claim 1, wherein said compound is in the form of a hydrochloride or hydroformate salt.

14. A compound according to claim 11, wherein said compound is in the form of a hydrochloride or hydroformate salt.

15. A compound according to claim 14, wherein said compound is selected from: N-((3R)-1-Aza-bicyclo[2.2.2]oct-3-yl)benzothiazole-4-carboxamide dihydrochloride,
N-((3S)-1-Aza-bicyclo[2.2.2]oct-3-yl)benzothiazole-4-carboxamide dihydrochloride,
N-((3R)-1-Azabicyclo[2,2,2]oct-3-yl)benzothiazole-7-carboxamide hydrochloride, or
N-((3S)-1-Azabicyclo[2,2,2]oct-3-yl)benzothiazole-7-carboxamide hydrochloride.

16. A compound according to claim 1, wherein

Ar is an aryl group containing 6 to 10 carbon atoms which is unsubstituted or substituted one or more times by alkyl having 1 to 8 carbon atoms, alkoxy having 1 to 8 carbon atoms, halogen, dialkylamino wherein the alkyl portions each have 1 to 8 carbon atoms, amino, cyano, hydroxyl, nitro, halogenated alkyl having 1 to 8 carbon atoms, halogenated alkoxy having 1 to 8 carbon atoms, hydroxyalkyl having 1 to 8 carbon atoms, hydroxyalkoxy having 2 to 8 carbon atoms, alkenyloxy having 3 to 8 carbon atoms, alkylthio having 1 to 8 carbon atoms, alkylsulphinyl having 1 to 8 carbon; atoms, alkylsulphonyl having 1 to 8 carbon atoms, monoalkylamino having 1 to 8 carbon atoms, cycloalkylamino wherein the cycloalkyl group has 3 to 7 carbon atoms and is optionally substituted by $C_{1-4}$-alkyl, $C_{1-4}$-alkoxy, hydroxyl, amino, monoalkylamino having 1 to 4 carbon atoms, and/or dialklyamino in which each alkyl group has 1 to 4 carbon atoms, aryloxy wherein the aryl portion contains 6 to 10 carbon atoms and is optionally substituted by halogen, $C_{1-4}$-alkyl, hydroxy, $C_{1-4}$-alkoxy, nitro, methylenedioxy, ethylenedioxy, amino, $C_{1-4}$-alkylamino, dialkylamino in which each alkyl group has 1 to 4 carbon atoms, $C_{1-4}$-hydroxyalkyl, $C_{1-4}$-hydroxyalkoxy, carboxy, cyano, $C_{1-4}$-alkoxy-carbonyl, $C_{1-4}$-alkylthio, $C_{1-4}$-alkylsulphinyl, $C_{1-4}$-alkylsulphonyl, phenoxy, or acetoxy, arylthio wherein the aryl portion contains 6 to 10 carbon atoms and is optionally substituted by halogen, $C_{1-4}$-alkyl, hydroxy, $C_{1-4}$-alkoxy, nitro, methylenedioxy, ethylenedioxy, amino, $C_{1-4}$-alkylamino, dialkylamino in which each alkyl group has 1 to 4 carbon atoms, $C_{1-4}$-hydroxyalkyl, $C_{1-4}$-hydroxyalkoxy, carboxy, cyano, $C_{1-4}$-alkoxy-carbonyl, alkylthio, $C_{1-4}$-alkylsulphinyl, $C_{1-4}$-alkylsulphonyl, phenoxy, or acetoxy, cycloalkyloxy wherein the cycloalkyl group has 3 to 7 carbon atoms and is optionally substituted by $C_{1-4}$-alkoxy, hydroxyl, amino, monoalkylamino having 1 to 4 carbon atoms, and/or dialklyamino in which each alkyl group has 1 to 4 carbon atoms, sulfo, sulfonylamino, or combinations thereof; and Het is a heterocyclic group, which is fully saturated, partially saturated or fully unsaturated, having 5 to 10 ring atoms in which at least 1 ring atom is a N, O or S atom, which is unsubstituted or substituted one or more times by halogen, aryl having 6 to 10 carbon atoms and is optionally substituted by halogen, $C_{1-4}$-alkyl, hydroxy, $C_{1-4}$-alkoxy, nitro, methylenedioxy, ethylenedioxy, amino, $C_{1-4}$-alkylamino, dialkylamino in which each alkyl group has 1 to 4 carbon atoms, $C_{1-4}$-hydroxyalkyl, $C_{1-4}$-hydroxyalkoxy, carboxy, cyano, $C_{1-4}$-alkoxy-carbonyl, $C_{1-4}$-alkylthio, $C_{1-4}$-alkylsulphinyl, $C_{1-4}$-alkylsulphonyl, phenoxy, or acetoxy, alkyl having 1 to 8 carbon atoms, alkoxy having 1 to 8 carbon atoms, cyano, trifluoromethyl, nitro, oxo, amino, monoalkylamino having 1 to 8 carbon atoms, dialkylamino wherein each alkyl group has 1 to 8 carbon atoms, or combinations thereof.

17. A compound according to claim 16, wherein Ar is substituted or unsubstituted phenyl or naphthyl, and Het is substituted or unsubstituted tetrahydrofuranyl, tetrahydrothienyl, pyrrolidinyl, piperidinyl, piperazinyl, morpholinyl, isoxazolinyl, furyl, thienyl, pyrrolyl, pyrazolyl, imidazolyl, pyridyl, pyrimidinyl, indolyl, quinolinyl, isoquinolinyl, or naphthyridinyl.

18. A compound according to claim 1, wherein $R^3$ is H, F, Cl, Br, I, OH. CN, nitro, $NH_2$, alkyl having 1 to 4 carbon atoms, fluorinated alkyl having 1 to 4 carbon atoms, cycloalkyl having 3 to 7 carbon atoms, cycloalkylalkyl having 4 to 7 carbon atoms, alkoxy having 1 to 4 carbon atoms, cycloalkoxy having 3 to 7 carbon atoms, cycloalkylalkoxy having 4 to 7 carbon atoms, alkylthio having 1 to 4 carbon atoms, fluorinated alkoxy having 1 to 4 carbon atoms, hydroxyalkyl having 1 to 4 carbon atoms, hydroxyalkoxy having 2 to 4 carbon atoms, monoalkylamino having 1 to 4 carbon atoms, or dialkylamino wherein each alkyl group independently has 1 to 4 carbon atoms.

* * * * *

UNITED STATES PATENT AND TRADEMARK OFFICE
CERTIFICATE OF CORRECTION

| | | |
|---|---|---|
| PATENT NO. | : 8,134,003 B2 | Page 1 of 1 |
| APPLICATION NO. | : 13/103512 | |
| DATED | : March 13, 2012 | |
| INVENTOR(S) | : Xie et al. | |

It is certified that error appears in the above-identified patent and that said Letters Patent is hereby corrected as shown below:

Column 90, line 8 reads, "$R^5$ is II, F, Cl, Br, I, OH, CN nitro, $NH_2$, alkyl having 1 to," SHOULD READ --$R^5$ is H, F, Cl, Br, I, OH, CN nitro, $NH_2$, alkyl having 1 to--

Column 93, line 58, Delete "(I') - (IV')"

Column 95, line 39 reads, "A compound according to claim 1, wherein and $R^3$ is II," SHOULD READ --A compound according to claim 1, wherein and $R^3$ is H,--

Signed and Sealed this

Thirteenth Day of November, 2012

David J. Kappos
*Director of the United States Patent and Trademark Office*